US006931277B1

(12) United States Patent
Yuzhakov et al.

(10) Patent No.: US 6,931,277 B1
(45) Date of Patent: *Aug. 16, 2005

(54) INTRACUTANEOUS MICRONEEDLE ARRAY APPARATUS

(75) Inventors: Vadim Vladimirovich Yuzhakov, Cincinnati, OH (US); Faiz Feisal Sherman, West Chester, OH (US); Grover David Owens, Fairfield, OH (US); Vladimir Garstein, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/580,819

(22) Filed: May 26, 2000

Related U.S. Application Data

(63) Continuation-in-part of application No. 09/329,025, filed on Jun. 9, 1999, now Pat. No. 6,256,533.

(51) Int. Cl.[7] .......................... A61M 5/32; A61N 1/30
(52) U.S. Cl. ...................................... 604/21; 604/272
(58) Field of Search ............................. 604/272–274, 604/22, 20, 264, 21

(56) References Cited

U.S. PATENT DOCUMENTS 3,918,449 A    11/1975   Pistor
3,964,482 A *   6/1976   Gerstel et al. ........... 604/890.1

(Continued)

FOREIGN PATENT DOCUMENTS

DE            2319591       11/1974
DE       196 24 578 A1     1/1998

(Continued)

*Primary Examiner*—Nicholas D. Lucchesi
*Assistant Examiner*—Matthew DeSanto
(74) *Attorney, Agent, or Firm*—Larry L. Huston; Leonard W. Lewis

(57) ABSTRACT

Improved microneedle arrays are provided having a sufficiently large separation distance between each of the individual microneedles to ensure penetration of the skin while having a sufficiently small separation distance to provide high transdermal transport rates. A very useful range of separation distances between microneedles is in the range of 100–300 microns, and more preferably in the range of 100–200 microns. The outer diameter and microneedle length is also very important, and in combination with the separation distance will be crucial as to whether or not the microneedles will actually penetrate the stratum corneum of skin. For circular microneedles, a useful outer diameter range is from 20–100 microns, and more preferably in the range of 20–50 microns. For circular microneedles that do not have sharp edges, a useful length for use with interstitial fluids is in the range of 50–200 microns, and more preferably in the range of 100–150 microns; for use with other biological fluids, a useful length is in the range of 200 microns–3 mm, and more preferably in the range of 200–400 microns. For circular microneedles having sharp side edges, a useful length for use with interstitial fluids is in the range of 50–200 microns, and more preferably in the range of 80–150 microns; for use with other biological fluids, a useful length is again in the range of 200 microns–3 mm, and more preferably in the range of 200–400 microns. For solid microneedles having a star-shaped profile with sharp edges for its star-shaped blades, a useful length for use with interstitial fluids is in the range of 50–200 microns, and more preferably in the range of 80–150 microns; for use with other biological fluids, a useful length is again in the range of 200 microns–3 mm, and more preferably in the range of 200–400 microns, while the radius of each of its blades is in the range of 10–50 microns, and more preferably in the range of 10–15 microns.

1 Claim, 37 Drawing Sheets

U.S. PATENT DOCUMENTS

| | | | |
|---|---|---|---|
| 4,055,029 A | 10/1977 | Kalbow | |
| 4,180,232 A | 12/1979 | Hardigg | |
| 4,381,963 A | 5/1983 | Goldstein et al. | 156/245 |
| 4,585,991 A | 4/1986 | Reid et al. | |
| 4,784,737 A | 11/1988 | Ray et al. | 204/180.1 |
| 4,837,049 A | 6/1989 | Byers et al. | 427/96 |
| 5,134,079 A | 7/1992 | Cusack et al. | |
| 5,156,591 A | 10/1992 | Gross et al. | 604/20 |
| 5,158,073 A | 10/1992 | Bukowski | |
| 5,162,043 A | 11/1992 | Lew et al. | |
| 5,198,192 A | 3/1993 | Saito et al. | |
| 5,215,088 A | 6/1993 | Normann | 128/642 |
| 5,250,023 A | 10/1993 | Lee et al. | 604/20 |
| 5,250,067 A | 10/1993 | Gelfer et al. | |
| 5,256,360 A | 10/1993 | Li | 264/219 |
| 5,279,544 A | 1/1994 | Gross et al. | 604/20 |
| 5,318,557 A | 6/1994 | Gross | 604/891.1 |
| 5,362,307 A | 11/1994 | Guy et al. | 604/20 |
| 5,383,512 A | 1/1995 | Jarvis | 164/46 |
| 5,498,235 A | 3/1996 | Flower | 604/20 |
| 5,512,219 A | 4/1996 | Rowland et al. | |
| 5,527,288 A | 6/1996 | Gross et al. | 604/140 |
| 5,551,953 A | 9/1996 | Lattin et al. | 604/20 |
| 5,591,123 A | 1/1997 | Sibalis et al. | |
| 5,591,139 A | 1/1997 | Lin et al. | 604/264 |
| 5,611,806 A | 3/1997 | Jang | 606/167 |
| 5,645,977 A | 7/1997 | Wu et al. | |
| 5,658,515 A | 8/1997 | Lee et al. | 264/219 |
| 5,676,850 A * | 10/1997 | Reed et al. | 216/2 |
| 5,681,580 A | 10/1997 | Jang et al. | 424/449 |
| 5,704,520 A | 1/1998 | Gross | 222/334 |
| 5,711,761 A | 1/1998 | Untereker et al. | 604/20 |
| 5,728,089 A | 3/1998 | Lal et al. | |
| 5,730,714 A | 3/1998 | Guy et al. | 604/20 |
| 5,735,273 A | 4/1998 | Kurnik et al. | 128/635 |
| 5,771,890 A | 6/1998 | Tamada | 128/635 |
| 5,800,420 A | 9/1998 | Gross et al. | 604/890.1 |
| 5,807,375 A | 9/1998 | Gross et al. | 604/890.1 |
| 5,814,020 A | 9/1998 | Gross | 604/41 |
| 5,820,622 A | 10/1998 | Gross et al. | 604/890.1 |
| 5,827,183 A | 10/1998 | Kurnik et al. | 600/345 |
| 5,848,985 A | 12/1998 | Muroki | |
| 5,848,990 A | 12/1998 | Cirelli et al. | 604/136 |
| 5,848,991 A | 12/1998 | Gross et al. | 604/140 |
| 5,855,801 A | 1/1999 | Lin et al. | 216/2 |
| 5,879,326 A | 3/1999 | Godshall et al. | |
| 5,938,684 A | 8/1999 | Lynch et al. | |
| 5,948,488 A | 9/1999 | Marecki et al. | |
| 5,964,729 A | 10/1999 | Choi et al. | |
| 6,023,629 A | 2/2000 | Tamada | |
| 6,036,659 A | 3/2000 | Ray et al. | |
| 6,038,465 A | 3/2000 | Melton, Jr. | |
| 6,047,208 A | 4/2000 | Flower | |
| 6,083,196 A | 7/2000 | Trautman et al. | |
| 6,091,975 A | 7/2000 | Daddona et al. | |
| 6,106,751 A | 8/2000 | Talbot et al. | |
| 6,129,696 A | 10/2000 | Sibalis | |
| 6,132,755 A | 10/2000 | Eicher et al. | |
| 6,219,574 B1 | 4/2001 | Cormier et al. | |
| 6,256,533 B1 | 7/2001 | Yuzhakov et al. | |
| 6,312,612 B1 | 11/2001 | Sherman et al. | |
| 6,334,856 B1 * | 1/2002 | Allen et al. | 604/191 |
| 6,375,627 B1 | 4/2002 | Mauze et al. | |
| 6,379,324 B1 | 4/2002 | Gartstein et al. | |
| 6,440,096 B1 | 8/2002 | Lastovich et al. | |
| 6,451,240 B1 | 9/2002 | Sherman et al. | |
| 6,471,903 B2 | 10/2002 | Sherman et al. | |
| 6,476,288 B1 | 11/2002 | Van Rijswijck et al. | |
| 6,494,830 B1 | 12/2002 | Wessel | |
| 6,533,884 B1 | 3/2003 | Mallik | |
| 6,565,532 B1 | 5/2003 | Yuzhakov et al. | |
| 6,591,124 B2 | 7/2003 | Sherman et al. | |
| 6,652,478 B1 * | 11/2003 | Gartstein et al. | 604/22 |
| 2001/0023324 A1 | 9/2001 | Pronovost et al. | |
| 2002/0006355 A1 | 1/2002 | Whiston | |
| 2002/0045859 A1 | 4/2002 | Garstein et al. | |
| 2002/0045907 A1 | 4/2002 | Sherman et al. | |
| 2002/0133129 A1 | 9/2002 | Arias et al. | |
| 2002/0177858 A1 | 11/2002 | Sherman et al. | |

FOREIGN PATENT DOCUMENTS

| | | | |
|---|---|---|---|
| EP | 0 312 662 A1 | 4/1989 | |
| EP | 0 407 063 A1 | 1/1991 | |
| EP | 0 796 128 B1 | 11/1995 | |
| EP | 1 086 719 A1 | 3/2001 | |
| EP | 1 174 078 A2 | 1/2002 | |
| FR | 2535602 A1 | 11/1984 | |
| GB | 783479 | 9/1957 | |
| GB | 2221394 A | 2/1990 | |
| JP | 09051878 | 8/1995 | A61B 5/00 |
| SU | 1667864 | 8/1991 | A61H 11/00 |
| WO | WO 93/17754 A1 | 9/1993 | |
| WO | WO 94/23777 A1 | 10/1994 | |
| WO | WO 95/33612 A1 | 12/1995 | |
| WO | WO 96/00109 | 1/1996 | A61N 1/30 |
| WO | WO 96/37155 | 11/1996 | A61B 17/20 |
| WO | WO 96/37256 | 11/1996 | A61N 1/30 |
| WO | WO 9703718 * | 2/1997 | |
| WO | WO 97/03718 | 6/1997 | A61M 37/00 |
| WO | WO 97/48440 | 12/1997 | A61N 1/30 |
| WO | WO 97/48441 | 12/1997 | A61N 1/30 |
| WO | WO 97/48442 | 12/1997 | A61N 1/30 |
| WO | WO 98/00193 | 1/1998 | A61M 31/00 |
| WO | WO 99/00155 | 1/1999 | A61M 5/32 |
| WO | WO 99/29298 | 6/1999 | A61K 9/00 |
| WO | WO 99/29364 | 6/1999 | A61M 37/00 |
| WO | WO 99/29365 | 6/1999 | A61M 37/00 |
| WO | WO 99/64580 | 12/1999 | C12N 15/00 |
| WO | WO 00/05166 A1 | 2/2000 | |
| WO | WO 00/35530 A1 | 6/2000 | |
| WO | WO 00/74763 A2 | 12/2000 | |
| WO | WO 00/74765 A1 | 12/2000 | |
| WO | WO 00/74766 A1 | 12/2000 | |
| WO | WO 0136037 * | 5/2001 | |
| WO | WO 02/07813 A1 | 1/2002 | |
| WO | WO 02/32331 A2 | 4/2002 | |
| WO | WO 02/72189 A2 | 9/2002 | |
| WO | WO 03/24290 A1 | 3/2003 | |
| WO | WO 03/24518 A2 | 3/2003 | |

* cited by examiner

CIRCULAR μNEEDLES – SEPARATION = 50 μm
OUTER DIAMETER – μm

|  | 10 | 20 | 30 | 40 | 50 | 60 | 70 | 80 | 90 | 100 |
|---|---|---|---|---|---|---|---|---|---|---|
| 30 | n | n | n | n | n | n | n | n | n | n |
| 60 | n | n | n | n | n | n | n | n | n | n |
| 90 | n | n | n | n | n | n | n | n | n | n |
| 120 | n | n | n | n | n | n | n | n | n | n |
| 150 | n | n | n | n | n | n | n | n | n | n |
| 180 | n | n | n | n | n | n | n | n | n | n |
| 210 | ◇ | n | n | n | n | n | n | n | n | n |
| 240 | Y | n | n | n | n | n | n | n | n | n |
| 270 | Y | ◇ | n | n | n | n | n | n | n | n |
| 300 | Y | Y | n | n | n | n | n | n | n | n |

μNEEDLE LENGTH – μm

CIRCULAR μNEEDLES – SEPARATION = 100 μm
OUTER DIAMETER – μm

|  | 10 | 20 | 30 | 40 | 50 | 60 | 70 | 80 | 90 | 100 |
|---|---|---|---|---|---|---|---|---|---|---|
| 30 | n | n | n | n | n | n | n | n | n | n |
| 60 | n | n | n | n | n | n | n | n | n | n |
| 90 | ◇ | n | n | n | n | n | n | n | n | n |
| 120 | Y | n | n | n | n | n | n | n | n | n |
| 150 | Y | ◇ | n | n | n | n | n | n | n | n |
| 180 | Y | Y | ◇ | n | n | n | n | n | n | n |
| 210 | Y | Y | Y | ◇ | n | n | n | n | n | n |
| 240 | Y | Y | Y | Y | n | n | n | n | n | n |
| 270 | Y | Y | Y | Y | ◇ | ◇ | n | n | n | n |
| 300 | Y | Y | Y | Y | Y | Y | n | n | n | n |

μNEEDLE LENGTH – μm

CIRCULAR μNEEDLES — SEPARATION = 150 μm
OUTER DIAMETER— μm

|  | 10 | 20 | 30 | 40 | 50 | 60 | 70 | 80 | 90 | 100 |
|---|---|---|---|---|---|---|---|---|---|---|
| 30 | n | n | n | n | n | n | n | n | n | n |
| 60 | n | n | n | n | n | n | n | n | n | n |
| 90 | ◇ | n | n | n | n | n | n | n | n | n |
| 120 | Y | ◇ | n | n | n | n | n | n | n | n |
| 150 | Y | ◇ | n | n | n | n | n | n | n | n |
| 180 | Y | Y | ◇ | ◇ | n | n | n | n | n | n |
| 210 | Y | Y | Y | Y | ◇ | n | n | n | n | n |
| 240 | Y | Y | Y | Y | Y | ◇ | n | n | n | n |
| 270 | Y | Y | Y | Y | Y | Y | ◇ | ◇ | n | n |
| 300 | Y | Y | Y | Y | Y | Y | Y | Y | n | n |

μ NEEDLE LENGTH – μm

FIG. 39

CIRCULAR μNEEDLES — SEPARATION = 200 μm
OUTER DIAMETER— μm

|  | 10 | 20 | 30 | 40 | 50 | 60 | 70 | 80 | 90 | 100 |
|---|---|---|---|---|---|---|---|---|---|---|
| 30 | n | n | n | n | n | n | n | n | n | n |
| 60 | ◇ | n | n | n | n | n | n | n | n | n |
| 90 | Y | ◇ | n | n | n | n | n | n | n | n |
| 120 | Y | Y | ◇ | n | n | n | n | n | n | n |
| 150 | Y | Y | Y | ◇ | n | n | n | n | n | n |
| 180 | Y | Y | Y | Y | ◇ | ◇ | n | n | n | n |
| 210 | Y | Y | Y | Y | Y | Y | ◇ | ◇ | n | n |
| 240 | Y | Y | Y | Y | Y | Y | Y | Y | ◇ | n |
| 270 | Y | Y | Y | Y | Y | Y | Y | Y | Y | ◇ |
| 300 | Y | Y | Y | Y | Y | Y | Y | Y | Y | Y |

μ NEEDLE LENGTH – μm

FIG. 40

CIRCULAR μNEEDLES − SEPARATION = 250 μm
OUTER DIAMETER− μm

| | 10 | 20 | 30 | 40 | 50 | 60 | 70 | 80 | 90 | 100 |
|---|---|---|---|---|---|---|---|---|---|---|
| 30 | n | n | n | n | n | n | n | n | n | n |
| 60 | n | n | n | n | n | n | n | n | n | n |
| 90 | ◇ | ◇ | n | n | n | n | n | n | n | n |
| 120 | Y | Y | ◇ | n | n | n | n | n | n | n |
| 150 | Y | Y | Y | ◇ | ◇ | ◇ | ◇ | ◇ | n | n |
| 180 | Y | Y | Y | Y | Y | Y | Y | ✶ | ◇ | n |
| 210 | Y | Y | Y | Y | Y | Y | Y | Y | Y | ◇ |
| 240 | Y | Y | Y | Y | Y | Y | Y | Y | Y | Y |
| 270 | Y | Y | Y | Y | Y | Y | Y | Y | Y | Y |
| 300 | Y | Y | Y | Y | Y | Y | Y | Y | Y | Y |

μNEEDLE LENGTH − μm

FIG. 41

CIRCULAR μNEEDLES − SEPARATION = 300 μm
OUTER DIAMETER− μm

| | 10 | 20 | 30 | 40 | 50 | 60 | 70 | 80 | 90 | 100 |
|---|---|---|---|---|---|---|---|---|---|---|
| 30 | n | n | n | n | n | n | n | n | n | n |
| 60 | n | n | n | n | n | n | n | n | n | n |
| 90 | ◇ | n | n | n | n | n | n | n | n | n |
| 120 | Y | ◇ | ◇ | n | n | n | n | n | n | n |
| 150 | Y | Y | Y | Y | ◇ | ◇ | n | n | n | n |
| 180 | Y | Y | Y | Y | Y | Y | Y | ◇ | ◇ | ◇ |
| 210 | Y | Y | Y | Y | Y | Y | Y | Y | Y | Y |
| 240 | Y | Y | Y | Y | Y | Y | Y | Y | Y | Y |
| 270 | Y | Y | Y | Y | Y | Y | Y | Y | Y | Y |
| 300 | Y | Y | Y | Y | Y | Y | Y | Y | Y | Y |

μ NEEDLE LENGTH − μm

FIG. 42

EDGED μNEEDLES — SEPARATION = 50 μm
OUTER DIAMETER— μm

| | 10 | 20 | 30 | 40 | 50 | 60 | 70 | 80 | 90 | 100 |
|---|---|---|---|---|---|---|---|---|---|---|
| 30  | n | n | n | n | n | n | n | n | n | n |
| 60  | n | n | n | n | n | n | n | n | n | n |
| 90  | n | n | n | n | n | n | n | n | n | n |
| 120 | n | n | n | n | n | n | n | n | n | n |
| 150 | ◇ | n | n | n | n | n | n | n | n | n |
| 180 | Y | n | n | n | n | n | n | n | n | n |
| 210 | Y | n | n | n | n | n | n | n | n | n |
| 240 | Y | ◇ | n | n | n | n | n | n | n | n |
| 270 | Y | Y | n | n | n | n | n | n | n | n |
| 300 | Y | Y | ◇ | n | n | n | n | n | n | n |

μNEEDLE LENGTH — μm

EDGED μNEEDLES — SEPARATION = 100 μm
OUTER DIAMETER— μm

| | 10 | 20 | 30 | 40 | 50 | 60 | 70 | 80 | 90 | 100 |
|---|---|---|---|---|---|---|---|---|---|---|
| 30  | n | n | n | n | n | n | n | n | n | n |
| 60  | ◇ | n | n | n | n | n | n | n | n | n |
| 90  | Y | ◇ | n | n | n | n | n | n | n | n |
| 120 | Y | Y | ◇ | n | n | n | n | n | n | n |
| 150 | Y | Y | Y | n | n | n | n | n | n | n |
| 180 | Y | Y | Y | n | n | n | n | n | n | n |
| 210 | Y | Y | Y | ◇ | n | n | n | n | n | n |
| 240 | Y | Y | Y | Y | ◇ | n | n | n | n | n |
| 270 | Y | Y | Y | Y | Y | ◇ | n | n | n | n |
| 300 | Y | Y | Y | Y | Y | Y | n | n | n | n |

μ NEEDLE LENGTH — μm

EDGED μNEEDLES — SEPARATION = 150 μm
OUTER DIAMETER— μm

|  | 10 | 20 | 30 | 40 | 50 | 60 | 70 | 80 | 90 | 100 |
|---|---|---|---|---|---|---|---|---|---|---|
| 30 | n | n | n | n | n | n | n | n | n | n |
| 60 | ◇ | ◇ | n | n | n | n | n | n | n | n |
| 90 | Y | Y | ◇ | n | n | n | n | n | n | n |
| 120 | Y | Y | Y | ◇ | n | n | n | n | n | n |
| 150 | Y | Y | Y | Y | ◇ | n | n | n | n | n |
| 180 | Y | Y | Y | Y | Y | ◇ | n | n | n | n |
| 210 | Y | Y | Y | Y | Y | Y | ◇ | n | n | n |
| 240 | Y | Y | Y | Y | Y | Y | Y | ◇ | n | n |
| 270 | Y | Y | Y | Y | Y | Y | Y | Y | ◇ | n |
| 300 | Y | Y | Y | Y | Y | Y | Y | Y | Y | ◇ |

μ NEEDLE LENGTH — μm

FIG. 45

EDGED μNEEDLES — SEPARATION = 200 μm
OUTER DIAMETER— μm

|  | 10 | 20 | 30 | 40 | 50 | 60 | 70 | 80 | 90 | 100 |
|---|---|---|---|---|---|---|---|---|---|---|
| 30 | n | n | n | n | n | n | n | n | n | n |
| 60 | n | n | n | n | n | n | n | n | n | n |
| 90 | ◇ | ◇ | n | n | n | n | n | n | n | n |
| 120 | Y | Y | ◇ | n | n | n | n | n | n | n |
| 150 | Y | Y | Y | ◇ | ◇ | ◇ | n | n | n | n |
| 180 | Y | Y | Y | Y | Y | Y | ◇ | n | n | n |
| 210 | Y | Y | Y | Y | Y | Y | Y | ◇ | ◇ | n |
| 240 | Y | Y | Y | Y | Y | Y | Y | Y | Y | ◇ |
| 270 | Y | Y | Y | Y | Y | Y | Y | Y | Y | Y |
| 300 | Y | Y | Y | Y | Y | Y | Y | Y | Y | Y |

μ NEEDLE LENGTH — μm

FIG. 46

EDGED μNEEDLES – SEPARATION = 250 μm
OUTER DIAMETER– μm

|  | 10 | 20 | 30 | 40 | 50 | 60 | 70 | 80 | 90 | 100 |
|---|---|---|---|---|---|---|---|---|---|---|
| 30 | n | n | n | n | n | n | n | n | n | n |
| 60 | ◇ | n | n | n | n | n | n | n | n | n |
| 90 | Y | ◇ | ◇ | n | n | n | n | n | n | n |
| 120 | Y | Y | Y | ◇ | ◇ | ◇ | n | n | n | n |
| 150 | Y | Y | Y | Y | Y | Y | ◇ | ◇ | ◇ | ◇ |
| 180 | Y | Y | Y | Y | Y | Y | Y | Y | Y | Y |
| 210 | Y | Y | Y | Y | Y | Y | Y | Y | Y | Y |
| 240 | Y | Y | Y | Y | Y | Y | Y | Y | Y | Y |
| 270 | Y | Y | Y | Y | Y | Y | Y | Y | Y | Y |
| 300 | Y | Y | Y | Y | Y | Y | Y | Y | Y | Y |

μ NEEDLE LENGTH – μm

EDGED μ NEEDLES – SEPARATION = 300 μm
OUTER DIAMETER– μm

|  | 10 | 20 | 30 | 40 | 50 | 60 | 70 | 80 | 90 | 100 |
|---|---|---|---|---|---|---|---|---|---|---|
| 30 | n | n | n | n | n | n | n | n | n | n |
| 60 | ◇ | n | n | n | n | n | n | n | n | n |
| 90 | Y | ◇ | ◇ | ◇ | n | n | n | n | n | n |
| 120 | Y | Y | Y | Y | ◇ | ◇ | ◇ | n | n | n |
| 150 | Y | Y | Y | Y | Y | Y | Y | ◇ | n | n |
| 180 | Y | Y | Y | Y | Y | Y | Y | Y | ◇ | ◇ |
| 210 | Y | Y | Y | Y | Y | Y | Y | Y | Y | Y |
| 240 | Y | Y | Y | Y | Y | Y | Y | Y | Y | Y |
| 270 | Y | Y | Y | Y | Y | Y | Y | Y | Y | Y |
| 300 | Y | Y | Y | Y | Y | Y | Y | Y | Y | Y |

μ NEEDLE LENGTH – μm

EMBOSSING

INTRACUTANEOUS MICRONEEDLE ARRAY APPARATUS

CROSS REFERENCES TO RELATED APPLICATIONS

This is a continuation-in-part of prior application Ser. No. 09/329,025, filed on Jun. 9, 1999 now U.S. Pat. No. 6,256,533.

TECHNICAL FIELD

The present invention relates generally to medical devices and is particularly directed to a fluid dispensing device and a fluid sampling device of the type which, in one embodiment penetrates the stratum corneum and epidermis, but not into the dermis of skin, and in another embodiment penetrates into the dermis so as to interface with blood or other biological fluids. The invention is specifically disclosed as an array of microneedles which painlessly and with minimal trauma to the skin enable fluid transfer either into a body as a dispensing device, or from the body to sample body fluid.

BACKGROUND OF THE INVENTION

Topical delivery of drugs is a very useful method for achieving systemic or localized pharmacological effects. The main challenge in transcutaneous drug delivery is providing sufficient drug penetration across the skin. The skin consists of multiple layers starting with a stratum corneum layer about (for humans) twenty (20) microns in thickness (comprising dead cells), a viable epidermal tissue layer about seventy (70) microns in thickness, and a dermal tissue layer about two (2) mm in thickness.

The thin layer of stratum corneum represents a major barrier for chemical penetration through skin. The stratum corneum is responsible for 50% to 90% of the skin barrier property, depending upon the drug material's water solubility and molecular weight. The epidermis comprises living tissue with a high concentration of water. This layer presents a lesser barrier for drug penetration. The dermis contains a rich capillary network close to the dermal/epidermal junction, and once a drug reaches the dermal depth it diffuses rapidly to deep tissue layers (such as hair follicles, muscles, and internal organs), or systemically via blood circulation.

Current topical drug delivery methods are based upon the use of penetration enhancing methods, which often cause skin irritation, and the use of occlusive patches that hydrate the stratum corneum to reduce its barrier properties. Only small fractions of topically applied drug penetrates through skin, with very poor efficiency.

Convention methods of biological fluid sampling and non-oral drug delivery are normally invasive. That is, the skin is lanced in order to extract blood and measure various components when performing fluid sampling, or a drug delivery procedure is normally performed by injection, which causes pain and requires special medical training. An alternative to drug delivery by injection has been proposed by Henry, McAllister, Allen, and Prausnitz, of Georgia Institute of Technology (in a paper titled "Micromachined Needles for the Transdermal Delivery of Drugs), in which an array of solid microneedles is used to penetrate through the stratum corneum and into the viable epidermal layer, but not to the dermal layer. In this Georgia Tech design, however, the fluid is prone to leakage around the array of microneedles, since the fluid is on the exterior surface of the structure holding the microneedles.

Another alternative to drug delivery by injection is disclosed in U.S. Pat. No. 3,964,482 (by Gerstel), in which an array of either solid or hollow microneedles is used to penetrate through the stratum corneum, into the epidermal layer, but not to the dermal layer. Fluid is to be dispensed either through hollow microneedles, through permeable solid projections, or around non-permeable solid projections that are surrounded by a permeable material or an aperture. A membrane material is used to control the rate of drug release, and the drug transfer mechanism is absorption. The microneedle size is disclosed as having a diameter of 15 gauge through 40 gauge (using standard medical gauge needle dimensions), and a length in the range of 5–100 microns. The permeable material may be filled with a liquid, hydrogel, sol, gel, of the like for transporting a drug through the projections and through the stratum corneum.

Another structure is disclosed in WO 98/00193 (by Altea Technologies, Inc.) in the form of a drug delivery system, or analyte monitoring system, that uses pyramidal-shaped projections that have channels along their outer surfaces. These projections have a length in the range of 30–50 microns, and provide a trans-dermal or trans-mucous delivery system, which can be enhanced with ultrasound.

Another structure, disclosed in WO 97/48440, WO 97/48441, and WO 97/48442 (by ALZA Corp.) is in the form of a device for enhancing transdermal agent delivery or sampling. It employs a plurality of solid metallic microblades and anchor elements, etched from a metal sheet, with a length of 25–400 mm. WO 96/37256 (by Silicon Microdevices, Inc.) disclosed another silicon microblade structure with blade lengths of 10–20 mm. For enhancing transdermal delivery.

Most of the other conventional drug delivery systems involve an invasive needle or plurality of needles. An example of this is U.S. Pat. No. 5,848,991 (by Gross) which uses a hollow needle to penetrate through the epidermis and into the dermis of the subject's skin when the housing containing an expansible/contractible chamber holding a reservoir of fluidic drug is attached to the skin. Another example of this is U.S. Pat. No. 5,250,023 (by Lee) which administers fluidic drugs using a plurality of solid needles that penetrate into the dermis. The Lee drug delivery system ionizes the drug to help transfer the drug into the skin by an electric charge. The needles are disclosed as being within the range of 200 microns through 2,000 microns.

Another example of a needle that penetrates into the dermis is provided in U.S. Pat. No. 5,591,139, WO 99/00155, and U.S. Pat. No. 5,855,801 (by Lin) in which the needle is processed using integrated circuit fabrication techniques. The needles are disclosed as having a length in the range of 1,000 microns through 6,000 microns.

The use of microneedles has great advantages in that intracutaneous drug delivery can be accomplished without pain and without bleeding. As used herein, the term "microneedles" refers to a plurality of elongated structures that are sufficiently long to penetrate through the stratum corneum skin layer and into the epidermal layer, yet are also sufficiently short to not penetrate to the dermal layer. Of course, if the dead cells have been completely or mostly removed from a portion of skin, then a very minute length of microneedle could be used to reach the viable epidermal tissue.

Since microneedle technology shows much promise for drug delivery, it would be a further advantage if a microneedle apparatus could be provided to sample fluids within skin tissue. Furthermore, it would be a further advantage to provide a microneedle array in which the individual microneedles were of a hollow structure so as to allow fluids to pass from an internal chamber through the hollow microneedles and into the skin, and were of sufficient length to ensure that they will reach into the epidermis, entirely through the stratum corneum.

SUMMARY OF THE INVENTION

Accordingly, it is a primary advantage of the present invention to provide a microneedle array in the form of a patch which can perform intracutaneous drug delivery. It is another advantage of the present invention to provide a microneedle array in the form of a patch that can perform biological body-fluid testing and/or sampling (including interstitial fluids and/or blood). It is a further advantage of the present invention to provide a microneedle array as part of a closed-loop system to control drug delivery, based on feedback information that analyzes body fluids, which can achieve real time continuous dosing and monitoring of body activity. It is yet another advantage of the present invention to provide an electrophoretically/microneedle-enhanced transdermal drug delivery system in order to achieve high-rate drug delivery and to achieve sampling of body fluids. It is a yet further advantage of the present invention to provide a method for manufacturing an array of microneedles using microfabrication techniques, including standard semiconductor fabrication techniques. It is still another advantage of the present invention to provide a method of manufacturing an array of microneedles comprising a plastic material by a "self-molding" method, a micromolding method, a micro-embossing method, or a microinjection method. It is still another advantage of the present invention to provide an array of edged microneedles that, in one configuration are hollow and have at least one blade with a substantially sharp edge that assists in penetration of the stratum corneum of skin, and in another configuration the microneedles are solid and have at least one blade with a substantially sharp edge to assist in penetrating the stratum corneum. It is still a further advantage of the present invention to provide a microneedle array that has sufficient separation distance between the individual microneedles so as to ensure penetration of the stratum corneum of skin to achieve greater transdermal flux. It is still another advantage of the present invention to provide a method of manufacturing an array of microneedles in which a metal mold is initially manufactured for use in a microembossing procedure, while allowing a sufficient separation distance between individual microneedles of the array, then use a procedure for creating hollow chambers and through-holes in the substrate of the microneedle array. It is yet another advantage of the present invention to provide a microneedle array that has sensing capabilities using optical, spectroscopic, colorimetric, electrochemical, thermal, gravimetric, and light scattering sensing means. It is still another advantage of the present invention to provide a method for manufacturing an array of microneedles that uses shear forces during a de-molding procedure to create sharp hollow microneedles.

Additional advantages and other novel features of the invention will be set forth in part in the description that follows and in part will become apparent to those skilled in the art upon examination of the following or may be learned with the practice of the invention.

To achieve the foregoing and other advantages, and in accordance with one aspect of the present invention, a first embodiment of an improved microneedle array is constructed of silicon and silicon dioxide compounds using MEMS (i.e., Micro-Electro-Mechanical-Systems) technology and standard microfabrication techniques. The microneedle array may be fabricated from a silicon die which can be etched in a microfabrication process to create hollow or solid individual microneedles. The resulting array of microneedles can penetrate with a small pressure through the stratum corneum of skin (including skin of animals, reptiles, or other creatures-typically skin of a living organism) to either deliver drugs or to facilitate biological fluid sampling (e.g., sampling interstitial fluids and/or blood) through the hollow microneedles or pores made through skin via solid microneedles. The drug reservoir, and/or the chemical analysis components for sampling body fluid, may be fabricated inside the silicon die, or an additional thick film layer can be bonded or otherwise attached over the silicon substrate to create the reservoir. The delivery of drugs and sampling of fluids can be performed by way of passive diffusion (e.g., time release), instantaneous injection, pressure, vacuum, ultrasound, or electrophoresis (e.g., iontophoresis). A complete closed-loop system can be manufactured including active elements, such as micro-machined pumps, heaters, and mixers, as well as passive elements such as sensors. A "smart patch" can thereby be fabricated that samples body fluids, performs chemistry to decide on the appropriate drug dosage, and then administers the corresponding amount of drug. Such a system can be made disposable, including one with an on-board power supply.

In a second embodiment, an array of hollow (or solid) microneedles can be constructed of plastic or some other type of molded or cast material. When using plastic, a micro-machining technique is used to fabricate the molds for a plastic microforming process. The molds are detachable and can be re-used. Since this procedure requires only a one-time investment in the mold micro-machining, the resulting plastic microstructure should be much less expensive than the use of microfabrication techniques to construct microneedle arrays, as well as being able to manufacture plastic microneedle arrays much more quickly and accurately. It will be understood that such hollow microneedles may also be referred to herein as "hollow elements," or "hollow projections," including in the claims. It will also be understood that such solid microneedles may also be referred to herein as "solid elements," or "solid projections" (or merely "projections"), including in the claims.

Molds used in the second embodiment of the present invention can contain a micropillar array and microhole array (or both), which are fabricated by micro-machining methods. Such micro-machining methods may include micro electrode-discharge machining to make the molds from a variety of metals, including stainless steel, aluminum, copper, iron, tungsten, and their alloys. The molds alternatively can be fabricated by microfabrication techniques, including deep reactive etching to make silicon, silicon dioxide, and silicon carbide molds. Also, LIGA or deep UV processes can be used to make molds and/or electroplated metal molds.

The manufacturing procedures for creating plastic (or other moldable material) arrays of microneedles include: "self-molding," micromolding, microembossing, and microinjection techniques. In the "self-molding" method, a plastic film (such as a polymer) is placed on a micropillar array, the plastic is then heated, and plastic deformation due to gravitational force causes the plastic film to deform and create the microneedle structure. Using this procedure, only a single mold-half is required. When using the micromolding technique, a similar micropillar array is used along with a second mold-half, which is then closed over the plastic film to form the microneedle structure. The micro-embossing method uses a single mold-half that contains an array of micropillars and conical cut-outs (microholes) which is pressed against a flat surface (which essentially acts as the second mold-half) upon which the plastic film is initially placed. In the micro-injection method, a melted plastic substance is injected between two micro-machined molds that contain microhole and micropillar arrays.

Of course, instead of molding a plastic material, the microneedle arrays of the present invention could also be constructed of a metallic material by a die casting method using some of the same structures as are used in the molding techniques discussed above. Since metal is somewhat more expensive and more difficult to work with, it is probably not the preferred material except for some very stringent requirements involving unusual chemicals or unusual application or placement circumstances. The use of chemical enhancers, ultrasound, or electric fields may also be used to increase transdermal flow rate when used with the microneedle arrays of the present invention.

In the dispensing of a liquid drug, the present invention can be effectively combined with the application of an electric field between an anode and cathode attached to the skin which causes a low-level electric current. The present invention combines the microneedle array with electrophoretic (e.g., iontophoresis) or electroosmotic enhancement, which provides the necessary means for molecules to travel through the thicker dermis into or from the body, thereby increasing the permeability of both the stratum corneum and deeper layers of skin. While the transport improvement through the stratum corneum is mostly due to microneedle piercing, electrophoresis (e.g., iontophoresis) provides higher transport rates in epidermis and dermis.

The present invention can thereby be used with medical devices to dispense drugs by electrophoretic/microneedle enhancement, to sample body fluids (while providing an electrophoretically/microneedle-enhanced body-fluid sensor), and a drug delivery system with fluid sampling feedback using a combination of the other two devices. For example, the body-fluid sensor can be used for a continuous or periodic sampling noninvasive measurement of blood glucose level by extracting glucose through the skin by reverse iontophoresis, and measuring its concentration using a bioelectrochemical sensor. The drug delivery portion of this invention uses the microneedle array to provide electrodes that apply an electric potential between the electrodes. One of the electrodes is also filled with an ionized drug, and the charged drug molecules move into the body due to the applied electric potential.

In an alternative embodiment of hollow microneedles, an edged microneedle is provided that includes at least one longitudinal blade that runs to the top surface or tip of the microneedle to aid in penetration of the stratum corneum of skin. The blade at the top surface provides a sharp tip that increases the likelihood of penetrating the skin when coming into contact therewith. In a preferred mode of the edged hollow microneedles, there are two such longitudinal blades that are constructed on opposite surfaces at approximately a 180° angle along the cylindrical side wall of the microneedle. Each edged blade has a cross-section that, when viewed from above the microneedle top, has a profile that is approximately that of an isosceles triangle. The blade's edge can run the entire length of the microneedle from its very top surface to its bottom surface where it is mounted onto the substrate, or the edge can be discontinued partway down the length of the microneedle as the microneedle outer surface approaches the substrate. The orientation of the blades in the microneedle array can be random, in which the blades of various individual microneedles point in all different directions.

In an alternative embodiment of a solid microneedle, a star-shaped solid microneedle is provided having at least one blade with a relatively sharp edge to assist in penetrating the stratum corneum of skin. In a preferred embodiment of a bladed or edged solid microneedle, a three pointed star-shaped solid microneedle is provided in which each blade has a triangular cross-section when viewed from the top of the microneedle, and each of these triangles approximates that of an isosceles triangle. The base of each of the isosceles triangles meets at a center of the microneedle to form a star-shaped structure when seen from the top of the microneedle. At least one hole through the substrate preferably is located near the side surfaces of at least one pair of blades of the solid microneedle, and preferably a through-hole would be located near each pair of such blades. In this preferred embodiment, there would be three edged blades and three adjacent through-holes in the substrate for each microneedle.

In a further alternative embodiment, a porous polymer, such as a hydrogel or solgel matrix can be impregnated with active material and deposited in the inside corners between the blades of the star. This provides an additional delivery mechanism.

The microneedle arrays of the present invention are significantly improved by using a proper separation distance between each of the individual microneedles. A very useful range of separation distances between microneedles is in the range of 100–300 microns, and more preferably in the range of 100–200 microns. The outer diameter and microneedle length is also very important, and in combination with the separation distance will be crucial as to whether or not the microneedles will actually penetrate the stratum corneum of skin. For hollow circular microneedles, a useful outer diameter range is from 20–100 microns, and more preferably in the range of 20–50 microns. For circular microneedles that do not have sharp edges, a useful length for use with interstitial fluids is in the range of 50–200 microns, and more preferably in the range of 100–150 microns; for use with other biological fluids, a useful length is in the range of 200 microns–3 mm, and more preferably in the range of 200–400 microns.

For circular hollow microneedles having sharp edges (such as those having the blades with triangular shaped edges), a useful length for use with interstitial fluids is in the range of 50–200 microns, and more preferably in the range of 80–150 microns; for use with other biological fluids, a useful length is again in the range of 200 microns–3 mm, and more preferably in the range of 200–400 microns. An example of a "sharp edge" as used herein is where the tip of the blade edge exhibits a dimension at its angular vertex that is as narrow or narrower than 0.5 microns. For solid microneedles having a star-shaped profile with sharp edges for its star-shaped blades, a useful length is in the range of 50–200 microns, and more preferably in the range of 80–150 microns, while the radius of each of its blades is in the range of 10–50 microns, and more preferably in the range of 10–15 microns.

The present invention can be manufactured with an alternative methodology using a mold preparation procedure that begins by placing an optical mask over a layer of PMMA material, then exposing the PMMA material that is not masked to x-rays or another type of high energy radiation (e.g., neutrons, electrons), and developing that PMMA material in a photoresist process. The remaining PMMA material is then coated (e.g., electroplated) with metal, such as nickel. When the coating has reached the appropriate thickness, it is detached to become a metal mold to create polymer or other type of moldable plastic material. This metal mold is then used in a microembossing procedure, in which the metal mold is pressed against a heated layer of polymer or other plastic material. Once the mold is pressed down to its proper distance, the plastic or polymer material is cooled to be solidified, and the mold is then detached, thereby leaving behind an array of microneedles. If the microneedles are hollow, then alternative procedures to create through-holes all the way through the microneedles and its underlying substrate material uses a methodology such as, for example, laser ablation, water jet erosion, electric discharge machining, plasma etching, and particle bombardment.

Another alternative procedure to create polymer or plastic microneedles is to begin with a two-layer laminate structure of biocompatible material. A metallic mold created by any process is then pressed down all the way through the top layer of this laminate, and partially into the bottom layer to ensure that the top layer is entirely penetrated. This occurs while the laminate material has been heated to its plastic, deformable temperature. Once the laminate material has then been cooled, the mold is removed and the top layer is detached from the bottom layer. This top layer will now have holes that will be further operated upon by a microembossing procedure using a different mold. This different mold creates hollow microneedles, in which the through-holes that normally need to be later created in the substrate have already been created in advance by the first pressing or molding procedure.

Another refinement of the present invention is to create a microneedle array that has sensing capabilities. In this structure, the tips or side grooves of the microneedles are coated with a particular chemical that aids in detecting a particular chemical or biological structure or fluid that come into contact with the tips of the microneedles. A sensing means is performed by the use of optical energy, for example such as a laser light source that is directed through the microneedle structure, in which the microneedles themselves are made of substantially transparent material. Other sensing mechanisms also could be used, as discussed hereinbelow.

A further alternative manufacturing process for hollow or solid microneedles is to create shear forces along the outer surfaces of the distal or tip portion of the hollow or solid microneedle during its molding or embossing process. The shear forces are actually created during the de-molding step while the microneedle array material is being cooled. The amount of shear can be controlled by the cool-down temperature, and if properly done will result in microneedles having sharp edges (rather than smooth edges) along their upper surfaces at their tips.

Still other advantages of the present invention will become apparent to those skilled in this art from the following description and drawings wherein there is described and shown a preferred embodiment of this invention in one of the best modes contemplated for carrying out the invention. As will be realized, the invention is capable of other different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification illustrate several aspects of the present invention, and together with the description and claims serve to explain the principles of the invention. In the drawings:

FIG. 37 is a table of microneedle penetration data for an array of circular hollow microneedles at a separation distance of 50 microns.

FIG. 38 is a table of microneedle penetration data for an array of circular hollow microneedles at a separation distance of 100 microns.

FIG. 39 is a table of microneedle penetration data for an array of circular hollow microneedles at a separation distance of 150 microns.

FIG. 40 is a table of microneedle penetration data for an array of circular hollow microneedles at a separation distance of 200 microns.

FIG. 41 is a table of microneedle penetration data for an array of circular hollow microneedles at a separation distance of 250 microns.

FIG. 42 is a table of microneedle penetration data for an array of circular hollow microneedles at a separation distance of 300 microns.

FIG. 43 is a table of microneedle penetration data for an array of edged hollow microneedles at a separation distance of 50 microns.

FIG. 44 is a table of microneedle penetration data for an array of edged hollow microneedles at a separation distance of 100 microns.

FIG. 45 is a table of microneedle penetration data for an array of edged hollow microneedles at a separation distance of 150 microns.

FIG. 46 is a table of microneedle penetration data for an array of edged hollow microneedles at a separation distance of 200 microns.

FIG. 47 is a table of microneedle penetration data for an array of edged hollow microneedles at a separation distance of 250 microns.

FIG. 48 is a table of microneedle penetration data for an array of edged hollow microneedles at a separation distance of 300 microns.

DETAILED DESCRIPTION OF THE PREFERRED EMBODIMENT

Reference will now be made in detail to the present preferred embodiment of the invention, an example of which is illustrated in the accompanying drawings, wherein like numerals indicate the same elements throughout the views.

Figure 1:
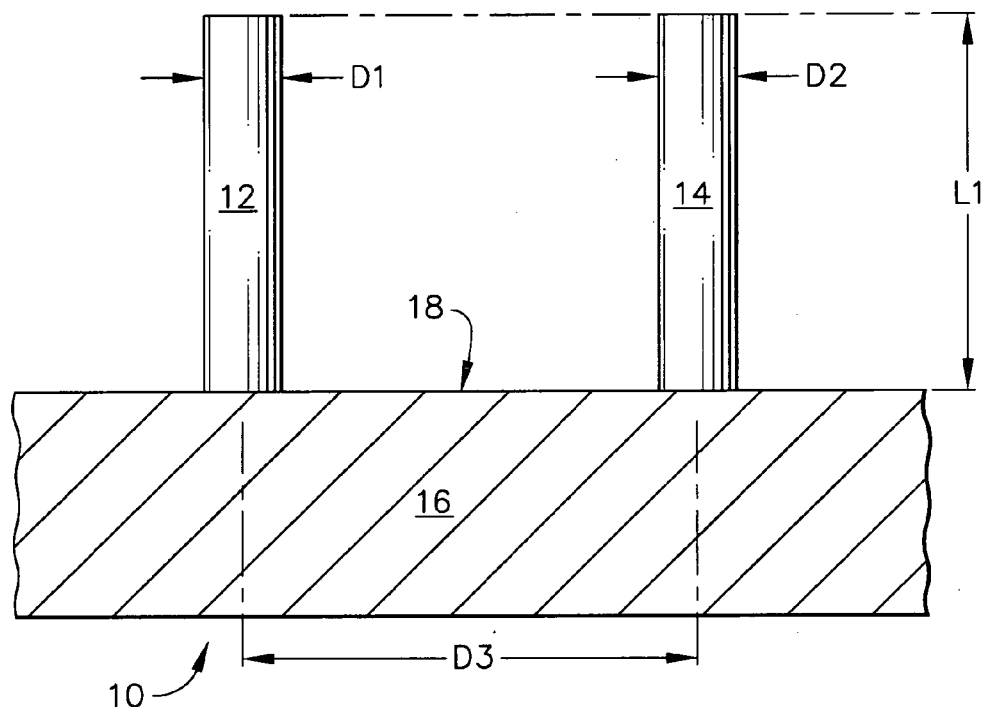
FIG. 1 is an elevational view in partial cross-section of a bottom mold provided at the initial step of a "self-molding" method of manufacturing an array of plastic microneedles, as constructed according to the principles of the present invention.

Referring now to the drawings, FIG. 1 shows a mold generally designated by the reference numeral 10 that comprises a plurality of micropillars, including micropillars 12 and 14, that are mounted to a base 16 having a planar upper surface 18. Micropillar 12 preferably is cylindrical in shape, and has an outer diameter designated "D1," whereas micropillar 14 (which also preferably is cylindrical in shape) has a diameter designated "D2." The centerlines of micropillars 12 and 14 are separated by a distance "D3," and the vertical height of micropillars 12 and 14 is designated by the letter "L1."

In a preferred configuration, the diameters D1 and D2 are in the range of 1–49 microns, more preferably about ten (10) microns (i.e., 10 microns=10 micrometers), the height L1 in the range of 50–3000 microns, whereas the separation distance D3 is in the range of 50–1000 microns, more preferably from 50–200 microns.

Microelectrode-discharge machining can be used to fabricate the mold 10 from metals, such as stainless steel, aluminum, copper, iron, tungsten, or other metal alloys. Mold 10 could also be fabricated from silicon or silicon carbide using integrated circuit processing, or photolithographic processing.

Figure 2:
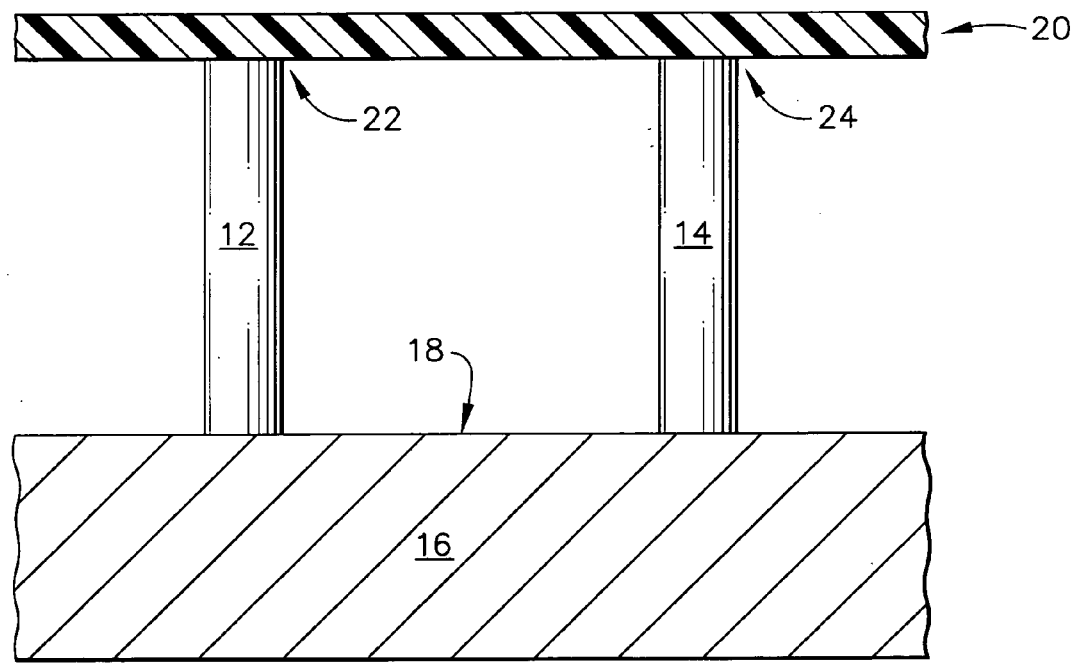
FIG. 2 is an elevational view in partial cross-section of the mold of FIG. 1 in a second step of the self-molding procedure.

FIG. 2 depicts the mold 10 and a thin layer of plastic, such as a polymer film, designated by the reference numeral 20, which is placed on the micropillars 12 and 14, thereby making contact at the reference numerals 22 and 24, respectively. Once the polymer film is placed on the micropillars, the polymer is heated to just above the melting temperature of the plastic material. Micropillars 12 and 14 are heated to above the glass transition temperature of the plastic material, but are preferably held below the melting temperature of the plastic material. This establishes a temperature gradient within the plastic film, after which the plastic film is subjected to natural gravitational forces, or placed in a centrifuge. Furthermore, an air-pressure gradient also can be established across the deforming plastic film, by applying pressure from above, or by applying a vacuum from below the film level. The overall effect on the plastic film is that it will undergo a "self-molding" operation, by way of the gravitational force or centrifugal force, and the air-pressure gradient can be used to accelerate the self-molding process.

Figure 3:
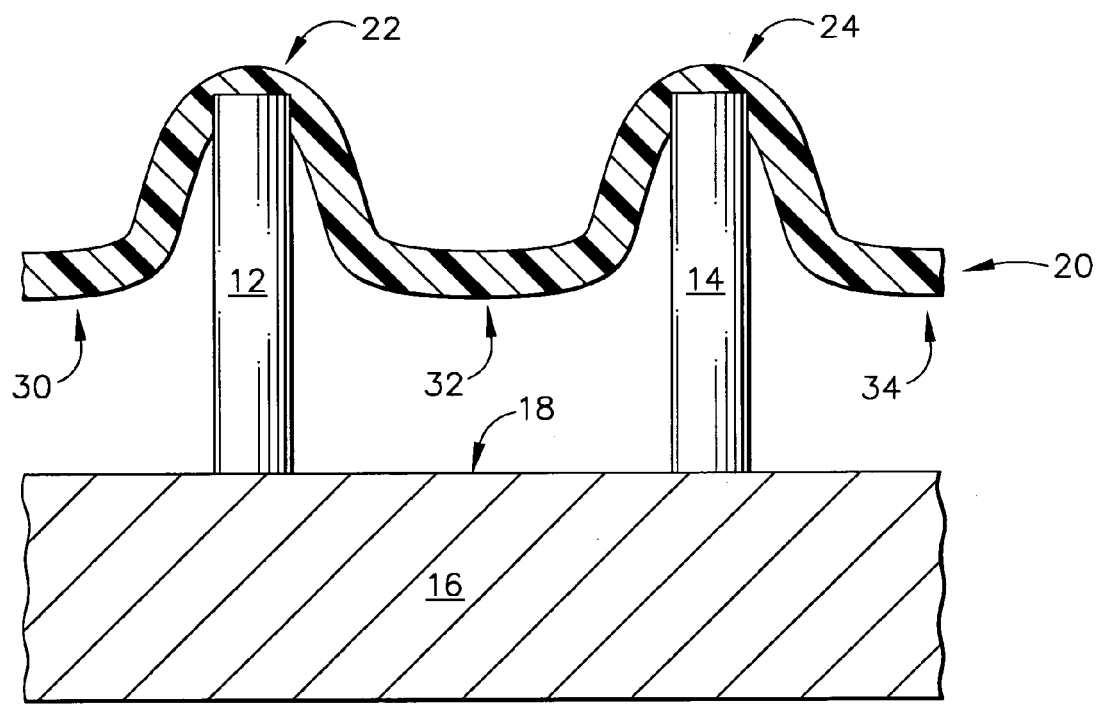
FIG. 3 is an elevational view in partial cross-section of the mold of FIG. 1 in a third step of the self-molding procedure.

FIG. 3 depicts the mold 10 at a further step in the processing of the plastic film, showing the result of the temperature gradient. This result is that the areas contacting the micropillars (at the reference numerals 22 and 24) will have a smaller deformation as compared to the remaining portions of the plastic film 20 that are between the pillars 12 and 14. Therefore, the portions 30, 32, and 34 of the plastic material will undergo greater deformation, as viewed on FIG. 3.

Figure 4:
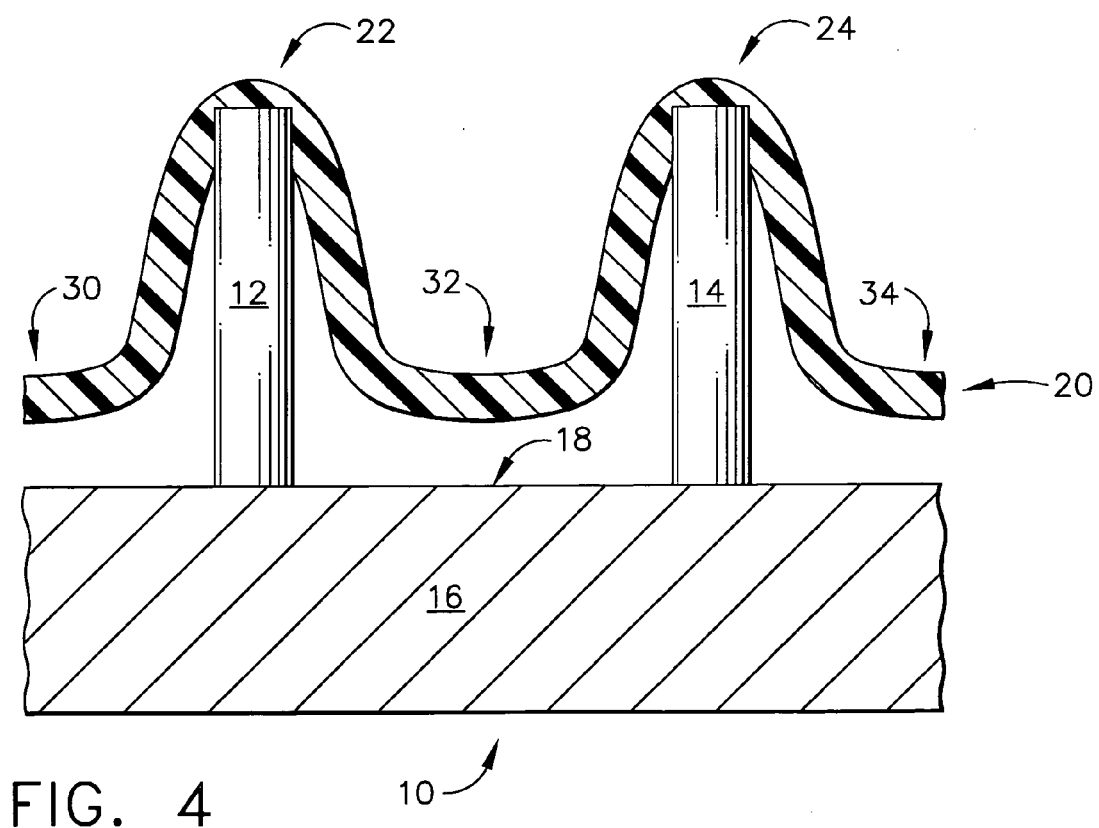
FIG. 4 is an elevational view in partial cross-section of the mold of FIG. 1 in a fourth step of the self-molding procedure.

FIG. 4 depicts the mold 10 at yet a later step in the self-molding process, showing the initial stage in which the mold (including micropillars 12 and 14) is heated above the melting temperature of the plastic material 20. During this latter stage of the self-molding process, the plastic material will continue to melt and to be removed from the tops of the pillars 12 and 14. As viewed in FIG. 4, the remaining portions not in contact with micropillars 12 and 14 will continue to deform downward (as viewed on FIG. 4) at the reference numerals 30, 32, and 34.

Figure 5:
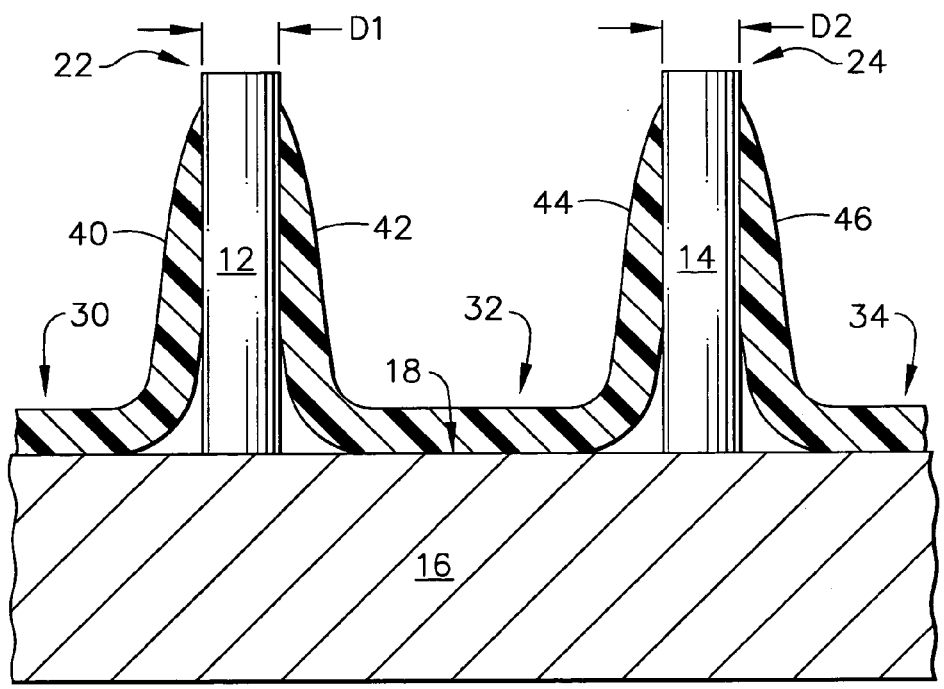
FIG. 5 is an elevational view in partial cross-section of the mold of FIG. 1 in a fifth step of the self-molding procedure.

FIG. 5 depicts the mold 10 at the final stage of self-molding, which illustrates the fact that the plastic material has completely melted down and away from the tops 22 and 24 of the micropillars 12 and 14. At this point the mold and the plastic material are both cooled down, thereby forming the final shape that will become the microneedles. This final shape includes an outer wall 40 and 42 for the microneedle being formed by micropillar 12, and an outer wall at 44 and 46 for the microneedle being formed at the micropillar 14.

Figure 6:
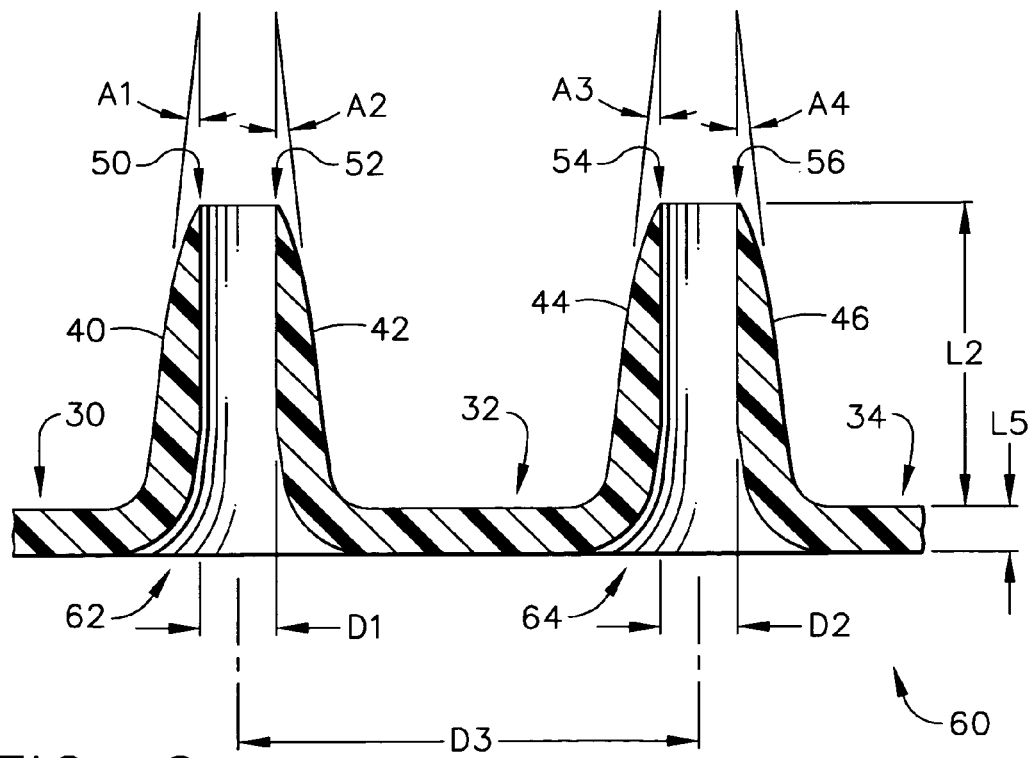
FIG. 6 is an elevational view in cross-section of an array of hollow microneedles constructed according to the self-molding procedure depicted in FIGS. 1–5.

FIG. 6 illustrates the cross-sectional shape of the microneedle array, generally designated by the reference numeral 60, after it has been detached from the mold 10. The left hand microneedle 62 has a relatively sharp upper edge, which appears as points 50 and 52. Its outer wall is illustrated at 40 and 42, which are sloped with respect to the vertical, as designated by the angles "A1" and "A2." The right-hand side microneedle 64 exhibits a similar sharp top edge, as indicated by the points 54 and 56, and also exhibits a sloped outer wall at 44 and 46. The angle of this outer wall is indicated at the angles "A3" and "A4." The preferred value of angles A1–A4 is in the range of zero (0) to forty-five (45) degrees.

The inner diameter of the left-hand microneedle 62 is indicated by the distance "D1," and the inner diameter of the right-hand microneedle 64 is indicated by the distance "D2." These distances D1 and D2 are substantially the same distance as the diameter of micropillars 12 and 14, as indicated in FIG. 1. Furthermore, the distance D3 between the centerlines of the microneedles on FIG. 6 is essentially the same as the distance D3 between the micropillars on FIG. 1. The length "L2" of the microneedles on FIG. 6 is somewhat less than the length L1 on FIG. 1, although this length L2 could theoretically be a maximum distance of L1.

It will be understood that the plastic material (also referred to herein as the "polymer film") may consist of any type of permanently deformable material that is capable of undergoing a gradual deformation as its melting point is reached or slightly exceeded. This "plastic material" could even be some type of metallic substance in a situation where the metallic material would deform at a low enough temperature so as to not harm the mold itself. The preferred material is a polyamide such as nylon, although many other types of polymer material certainly could be used to advantage. Other potential materials include: polyesters, vinyls, polystyrenes, polycarbonates, acrylics such as PMMA, polyurethanes, epoxides, phenolics, and acrylonitriles like acrylonitrilebutadienestyrene (ABS). Of course, one important criterion is that the material which makes up the microneedles does not chemically react with skin, or with the fluidic substance that is being transported through the hollow interiors of the microneedle array.

Figure 7:
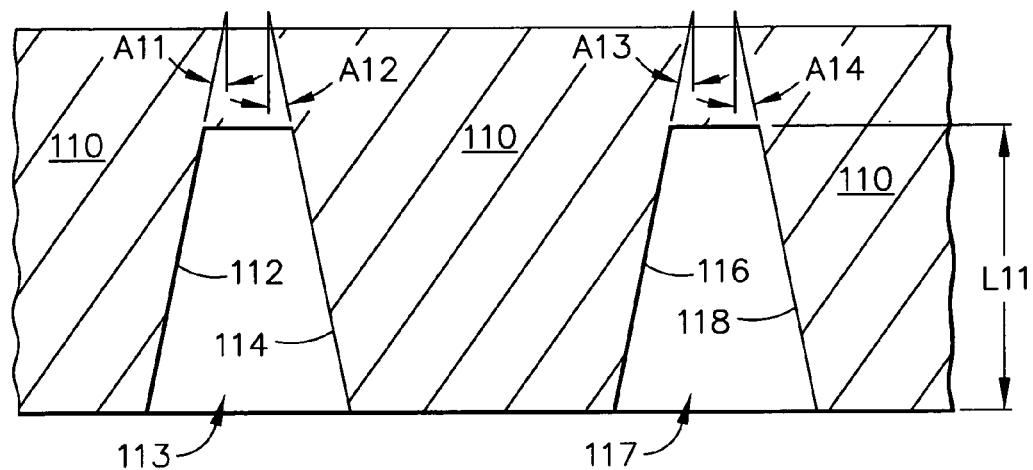
FIG. 7 is a cross-sectional view of a top mold-half used in a micromolding procedure, according to the principles of the present invention.

FIG. 7 depicts a top mold-half, generally designated by the reference numeral 110, of a second embodiment of the present invention in which the manufacturing method for creating an array of hollow microneedles is performed by a micromolding procedure. The top mold-half 110 includes two "microholes" that have sloped side walls, designated by the reference numerals 112 and 114 for the left-hand microhole 113, and by the reference numerals 116 and 118 for the right-hand microhole 117. The microholes 113 and 117 have a vertical (in FIG. 7) dimension referred to herein as a distance "L11". Microholes 113 and 117 correspond to a pair of micropillars 122 and 124 that are part of a bottom mold-half, generally designated by the reference number 120, and illustrated in FIG. 8.

Referring back to FIG. 7, the sloped side walls of the microhole 113 are depicted by the angles "A11" and "A12," with respect to the vertical. The side walls of microhole 117 are also sloped with respect to the vertical, as illustrated by the angles "A13" and "A14" on FIG. 7. Since microhole 113 preferably is in a conical overall shape, the angle A11 will be equal to the angle A12; similarly for microhole 117, the angle A13 will be equal to the angle A14. It is preferred that all microholes in the top mold-half 110 exhibit the same angle with respect to the vertical, which means that angles A11 and A13 are also equal to one another. A preferred value for angles A11–A14 is in the range of zero (0) through forty-five (45) degrees. The larger the angle from the vertical, the greater the trauma to the skin tissue when a microneedle is pressed against the skin. On FIG. 7, the illustrated angle A11 is approximately twelve (12) degrees.

Figure 8:
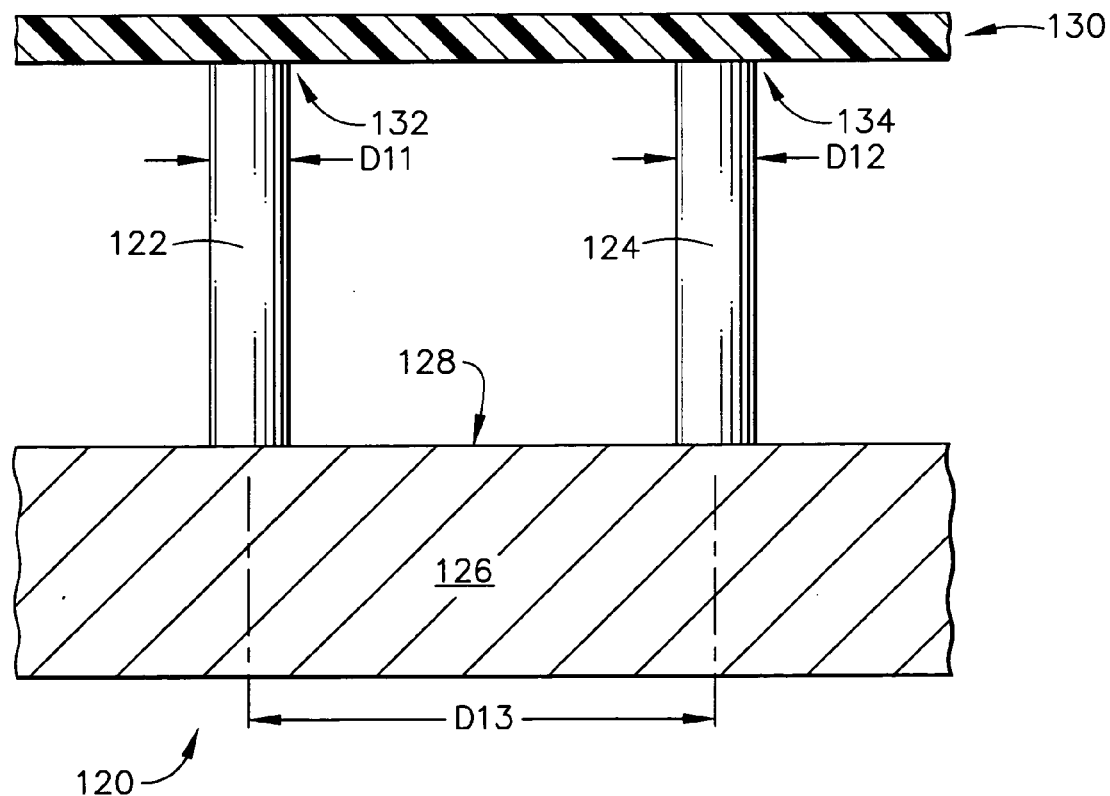
FIG. 8 is an elevational view of the bottom half of the mold that mates to the top mold-half of FIG. 7, and which is used to form plastic microneedles according to the micromolding procedure.

Referring now to FIG. 8, the bottom mold-half 120 includes a base 126 having a substantially planar top surface 128, upon which the two micropillars 122 and 124 are mounted. These micropillars are preferably cylindrical in shape, and have a diameter of D11 and D12, respectively. The distance between the centerlines of these micropillars is designated as D13. Diameters D11 and D12 preferably are in the range 1–49 microns, more preferably about 10 microns. The distance "D13" represents the separation distance between the center lines of micropillars 122 and 124, which preferably is in the range 50–1000 microns, more preferably in the range of 100–200 microns.

The two mold-halves 110 and 120 can be fabricated from metals using microelectrode-discharge machining techniques. Alternatively, the molds could be fabricated from silicon or silicon carbide using integrated circuit processing or lithographic processing.

Figure 9:
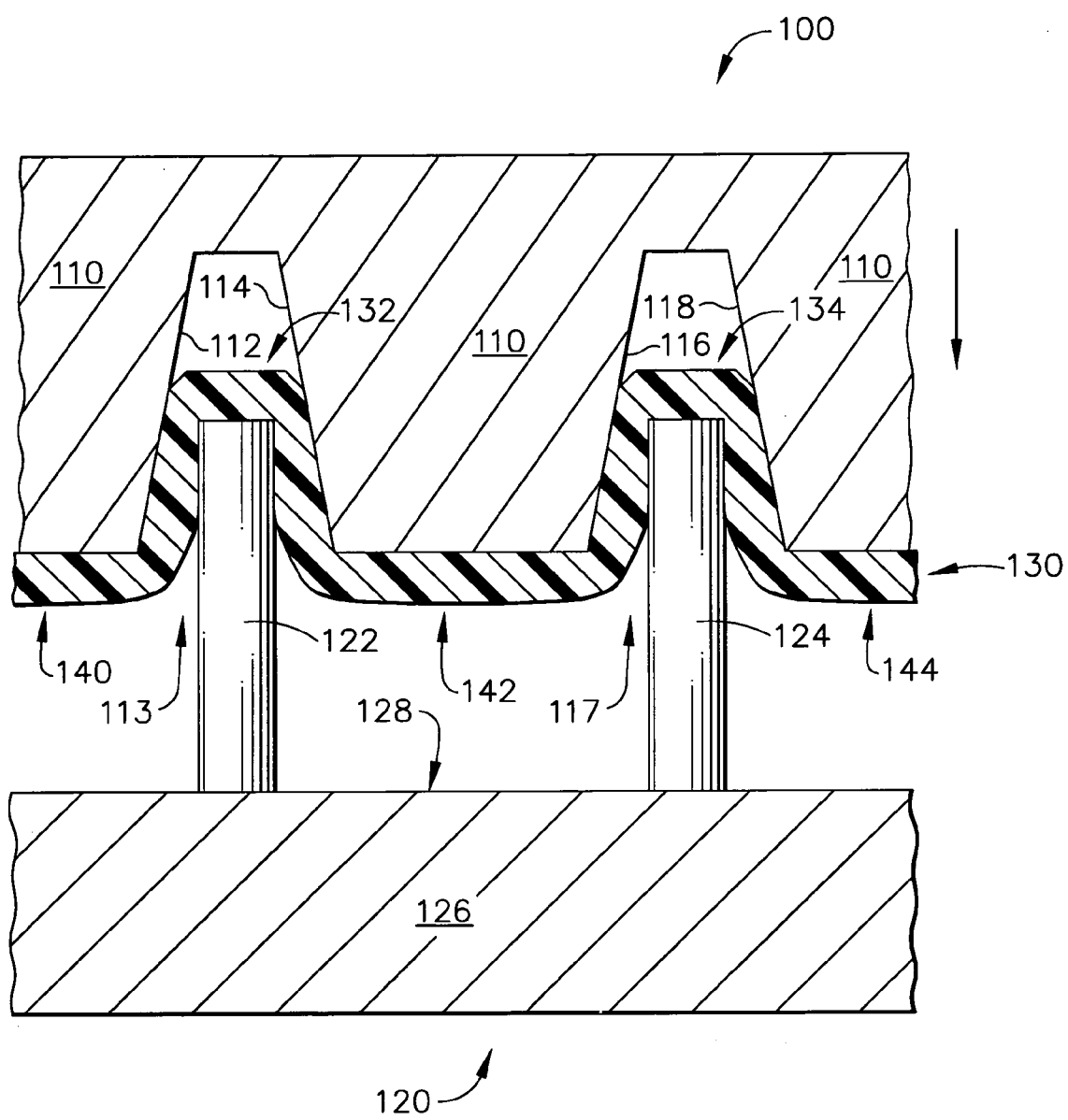
FIG. 9 is an elevational view in partial cross-section of one of the method steps in the micromolding procedure using the mold halves of FIGS. 7 and 8.

On FIG. 8, a thin plastic film, generally designated by the reference numeral 130, is placed on top of the micropillars and heated above the glass transition temperature of the plastic material while the plastic material 130 rests upon the tops of the pillars at 132 and 134, thereby causing the plastic material to become sufficient pliable or "soft" for purposes of permanently deforming the material's shape. Preferably, the temperature of the plastic material will not be raised above its melting temperature, although it would not inhibit the method of the present invention for the plastic material to become molten just before the next step of the procedure. In FIG. 9, the top mold-half 110 is pressed downward and begins to deform the plastic film 130. While a portion of the plastic material 130 temporarily resides above the micropillars at 132 and 134, a larger amount of the plastic material is pressed downward directly by the mold top-half 110 at 140, 142, and 144. As can be seen in FIG. 9, the two mold halves 110 and 120 are aligned so that the microholes 113 and 117 correspond axially to the micropillars 122 and 124, respectively. The two mold halves now begin to operate as a single mold assembly, generally designated by the reference numeral 100.

Figure 10:
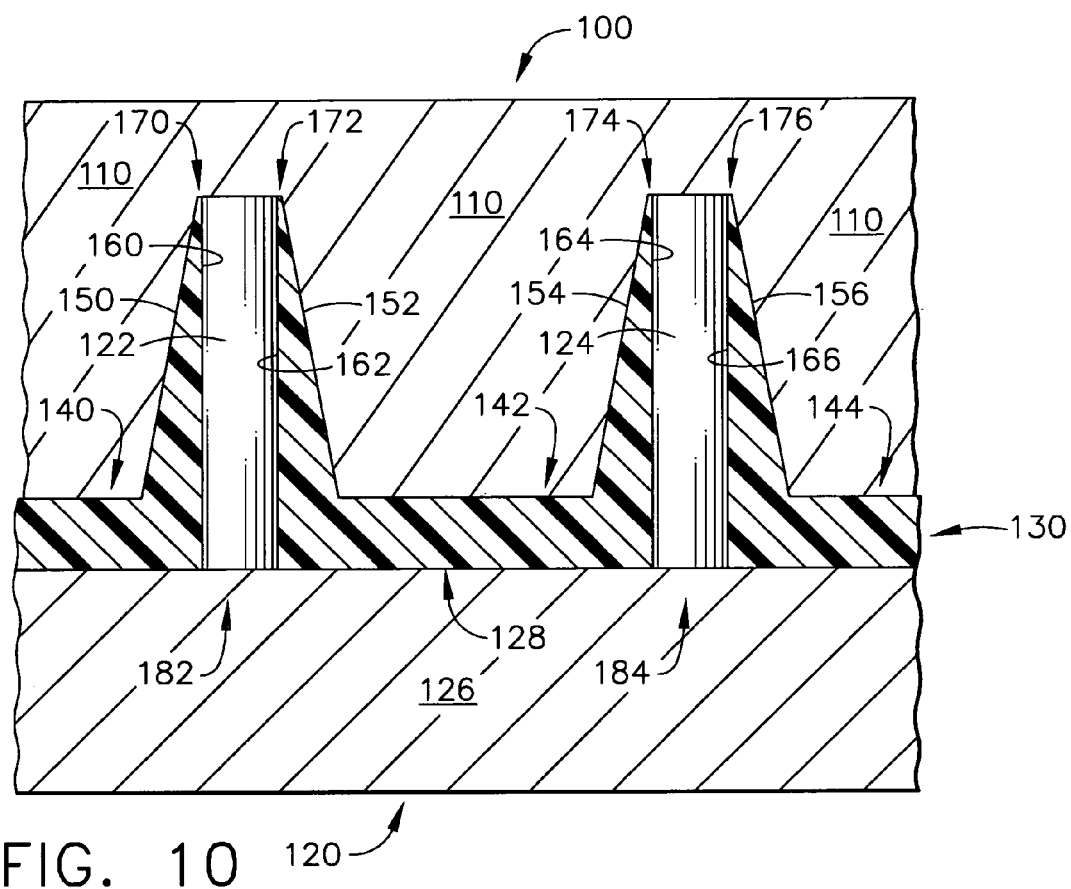
FIG. 10 is an elevational view in partial cross-section of the mold of FIG. 9 depicting the next step in the micromolding procedure.

In FIG. 10, the two mold halves 110 and 120 have completely closed, thereby squeezing all of the plastic material 130 away from the tops of the micropillars 122 and 124. At this point, the plastic microneedles are formed, and the mold and the plastic material are both cooled down.

The wall 112 and 114 of the first microhole 113 causes a side outer wall to be formed out of the plastic material at 150 and 152. The corresponding inner wall of the microneedle 182 is depicted at 160 and 162, which is caused by the shape of the micropillar 122. Since the outer wall is sloped, it will converge with the inner wall 160 and 162, near the top points at 170 and 172. A similar outer wall 154 and 156 is formed by the inner wall 116 and 118 of microhole 117. The inner wall of the microneedle 184 is depicted at 164 and 166, and these inner and outer walls converge near points 174 and 176.

Figure 11:
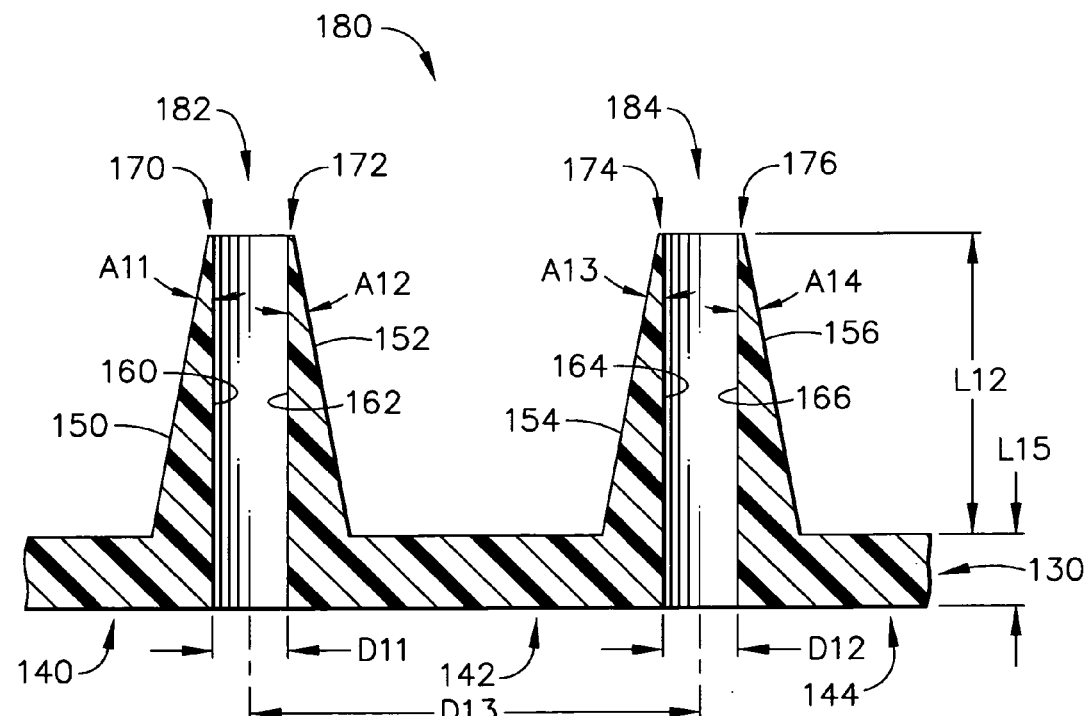
FIG. 11 is a cross-sectional view of an array of plastic microneedles constructed according to the micromolding procedure depicted in FIGS. 7–10.

FIG. 11 illustrates the microneedle array, generally designated by the reference numeral 180, after the mold is removed from the plastic material 130. A lower relatively planar base remains, as illustrated at 140, 142, and 144. On FIG. 11, two different microneedles are formed at 182 and 184. The angles formed by the walls are as follows: angle A11 by walls 150 and 160, angle A12 by walls 162 and 152, angle A13 by walls 154 and 164, and angle A14 by walls 166 and 156. The points at the top if the microneedles (designated at 170, 172, 174, and 176) are fairly sharp, and this sharpness can be adjusted by the shape of the mold with respect to the microholes and micropillar orientations.

The inner diameter of microneedle 182 is designated by the distance D11, and the inner diameter of the microneedle 184 is designated by the distance D12. The distance between the centerlines of these microneedles is designated as D13. These distances correspond to those illustrated on FIG. 8.

It is preferred that all of the angles A11–A14 are equal to one another, and that the angles fall within the range of zero (0) to forty-five (45) degrees. The preferred angle really depends upon the strength of the material being used to construct the microneedles, in which a greater angle (e.g., angle A11) provides greater strength. However, this angular increase also causes greater trauma to the skin.

Microneedle array 180 also includes a relatively flat base structure, as indicated at the reference numerals 140, 142, and 144. This base structure has a vertical thickness as designated by the dimension L15 (see FIG. 11). The microneedle height is designated by the dimension L12 on FIG. 11. The height must be sufficient to penetrate the skin through the stratum corneum and into the epidermis, and a preferred dimension for height L12 is in the range of 50–3000 microns (although, certainly microneedles shorter than 50 microns in length could be constructed in this manner—for use with skin cosmetics, for example). The thickness L15 can be of any size, however, the important criterion is that it be thick enough to be mechanically sound so as to retain the microneedle structure as it is used to penetrate the skin.

Figure 12:
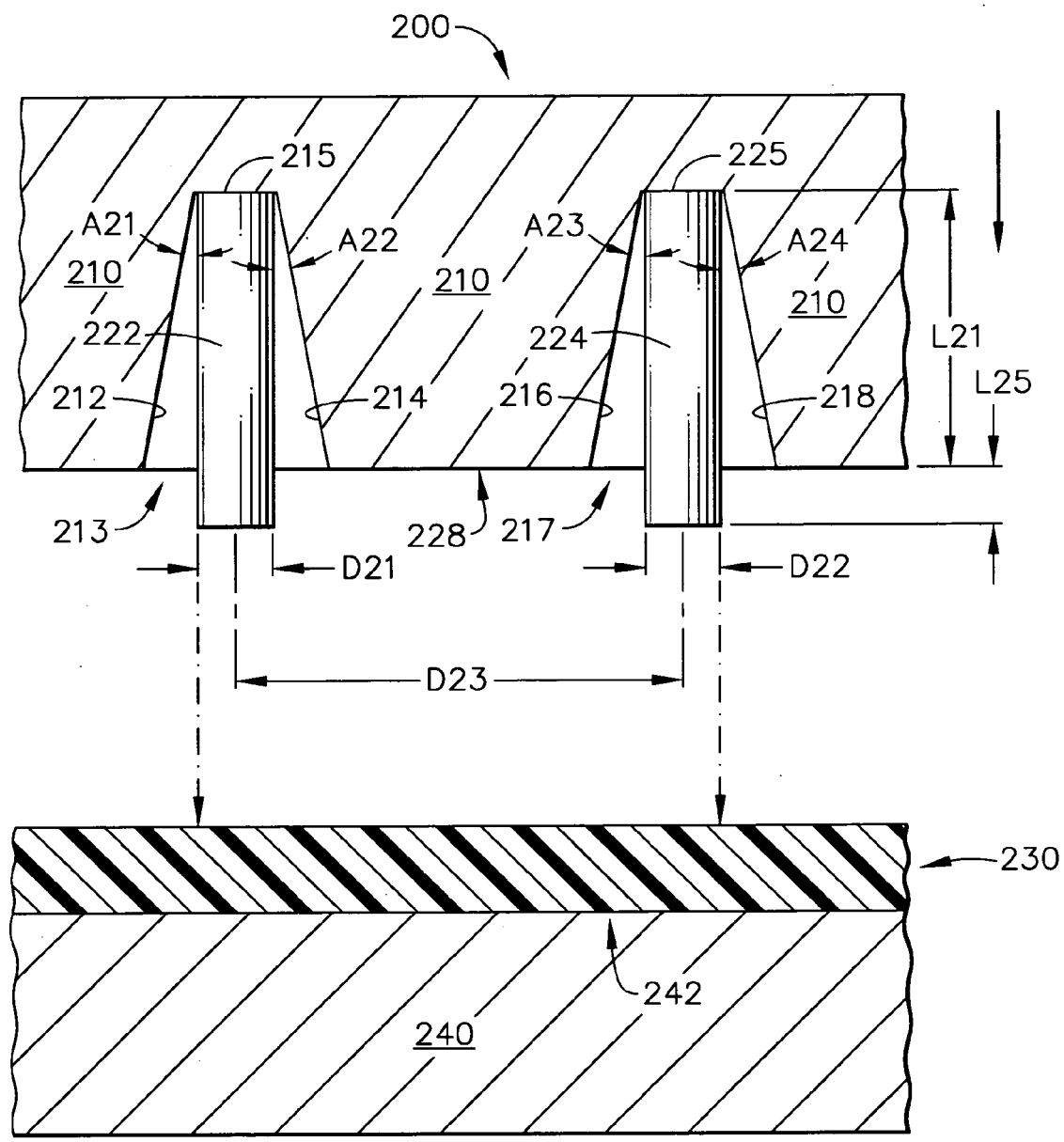
FIG. 12 is an elevational view in partial cross-section of a top mold-half and a bottom planar surface used in creating an array of molded, plastic microneedles by a microembossing procedure, as constructed according to the principles of the present invention.

Referring now to FIG. 12, a top mold-half 210 is combined with a planar bottom mold-half 240 to create an entire mold, generally designated by the reference numeral 200. The top mold-half 210 contains an array of microholes with micropillars at the center of each of the microholes. For example, a microhole 213, having its conical wall at 212 and 214, is preferably concentric with a micropillar 222, and a microhole 217, having its conical wall at 216 and 218, is preferably concentric with a micropillar 224.

The fabrication method used in conjunction with the mold 200 is referred to herein as "microembossing" for the reason that the bottom mold-half 240 is simply a flat or planar surface. This greatly simplifies the construction of this particular mold. A thin plastic film at 230 is placed upon the top surface 242 of this bottom mold-half 240. In the later steps, it will be seen that the plastic material 230 is heated while the top mold-half 210 is pressed down against the bottom mold-half 240.

Microhole 213 and micropillar 222 have an angular relationship as illustrated by the angles "A21" and "A22." A similar angular relationship exists for microhole 217 and micropillar 224, as illustrated by the angles "A23" and "A24." These angles A21–A24 will preferably be in the range of zero (0) to forty-five (45) degrees from the vertical. As noted hereinabove, the greater the angle, the greater the transport rate, however, also the greater trauma to the skin tissue when used.

Micropillar 222 preferably has a cylindrical shape with an outer diameter designated at "D21," and micropillar 224 similarly has a preferred cylindrical shape having a diameter "D22." Diameters D21 and D22 preferably are in the range 1–49 microns, more preferably about 10 microns. The distance "D23" represents the separation distance between the center lines of micropillars 222 and 224, which preferably is in the range 50–1000 microns, more preferably in the range of 100–200 microns.

The length of the micropillars from the bottom surface 228 of the top mold-half 210 to the closed end of the microholes at 215 and 225, respectively, is designated as the length "L21." The micropillars 222 and 224 are somewhat longer than this length L21, since they are to mate against the upper surface 242 of the bottom mold-half 240, and therefore are longer by a distance designated as "L25." In this manner, the microneedles will be hollow throughout their entire length. The combined length of dimensions L21 and L25 preferably will be approximately 150 microns.

The molds 210 and 240 will preferably be made from a metal, in which microelectrode-discharge machining can be used to fabricate such metallic molds. Alternatively, the molds could be fabricated from silicon or silicon carbide, for example, using integrated circuit processing or lithographic processing.

Figure 13:
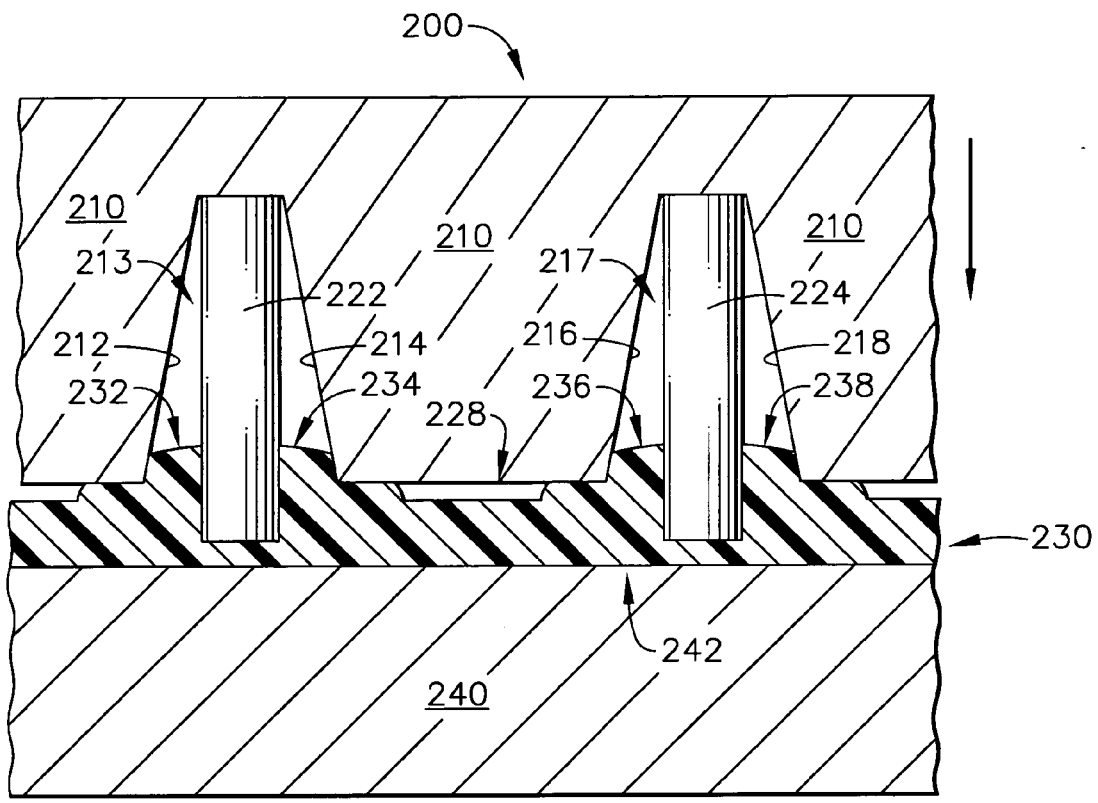
FIG. 13 is an elevational view in partial cross-section of the mold of FIG. 12 in a subsequent process step of the microembossing method.

Referring now to FIG. 13, after the plastic material is heated above its glass transition temperature, thereby causing the plastic material to become sufficient pliable or "soft" for purposes of permanently deforming the material's shape. Preferably, the temperature of the plastic material will not be raised above its melting temperature, although it would not inhibit the method of the present invention for the plastic material to become molten just before the top mold 210 begins to be pressed down against the plastic material 230. This top mold movement begins to deform that plastic material 230 such that it begins to fill the microholes, as illustrated at 232 and 234 (for microhole 213) and at 236 and 238 (for microhole 217).

Figure 14:
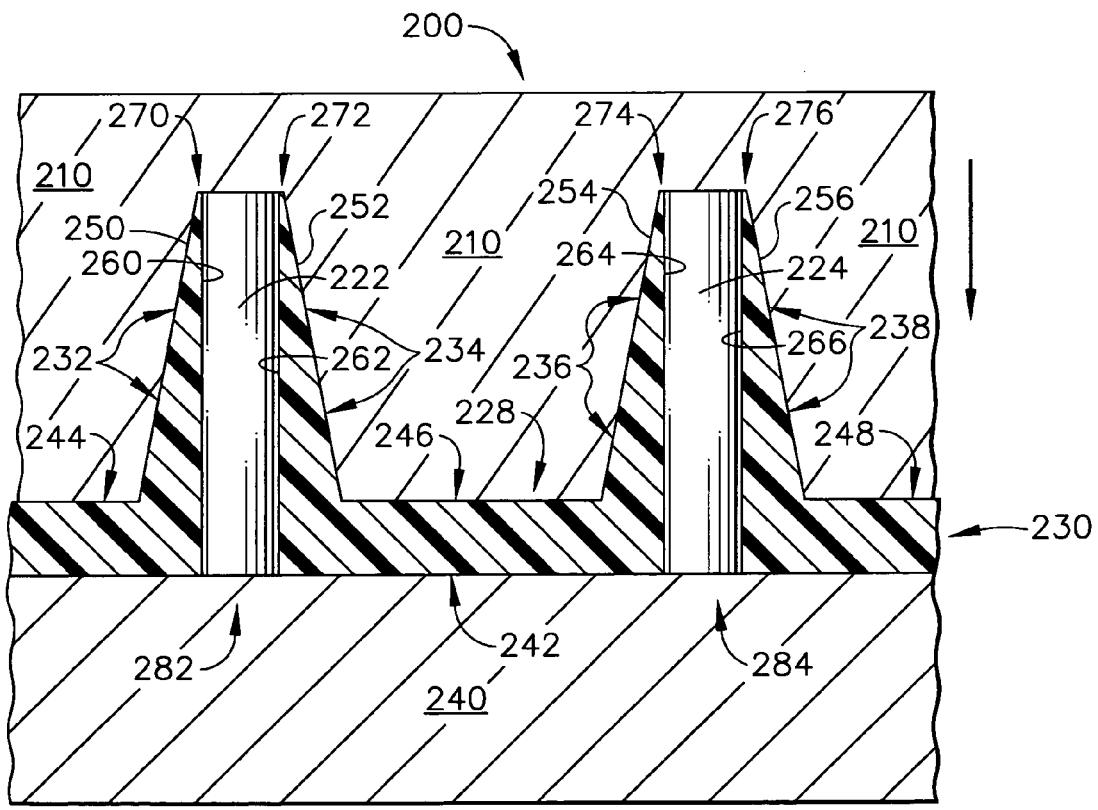
FIG. 14 is an elevational view in partial cross-section of the mold if FIG. 12 showing a later step in the microembossing procedure.

In FIG. 14, the top mold-half 210 has now been completely closed against the bottom planar mold-half 240, and the plastic material 230 has now completely filled the microholes, as illustrated at 232, 234, 236, and 238. The shape of the plastic material now has a conical outer wall at 250 and 252, and a corresponding cylindrical inner wall at 260 and 262, for the left-hand microneedle 282 on FIG. 14. Correspondingly for the right-hand microneedle 284, the plastic material shape has an outer conical wall at 254 and 256, as well as a cylindrical inner wall at 264 and 266. The conical outer walls and the cylindrical inner walls converge at the top points 270 and 272, and 274 and 276. The bottom surface 228 of the top mold-half 210 causes a base to be formed in the plastic material 230 at the locations indicated by the reference numerals 244, 246, and 248. Once this shape has been formed, the mold and the plastic material are cooled down, and then the molds are separated so that the plastic microneedle array is detached to form the shape as illustrated in FIG. 15.

Figure 15:
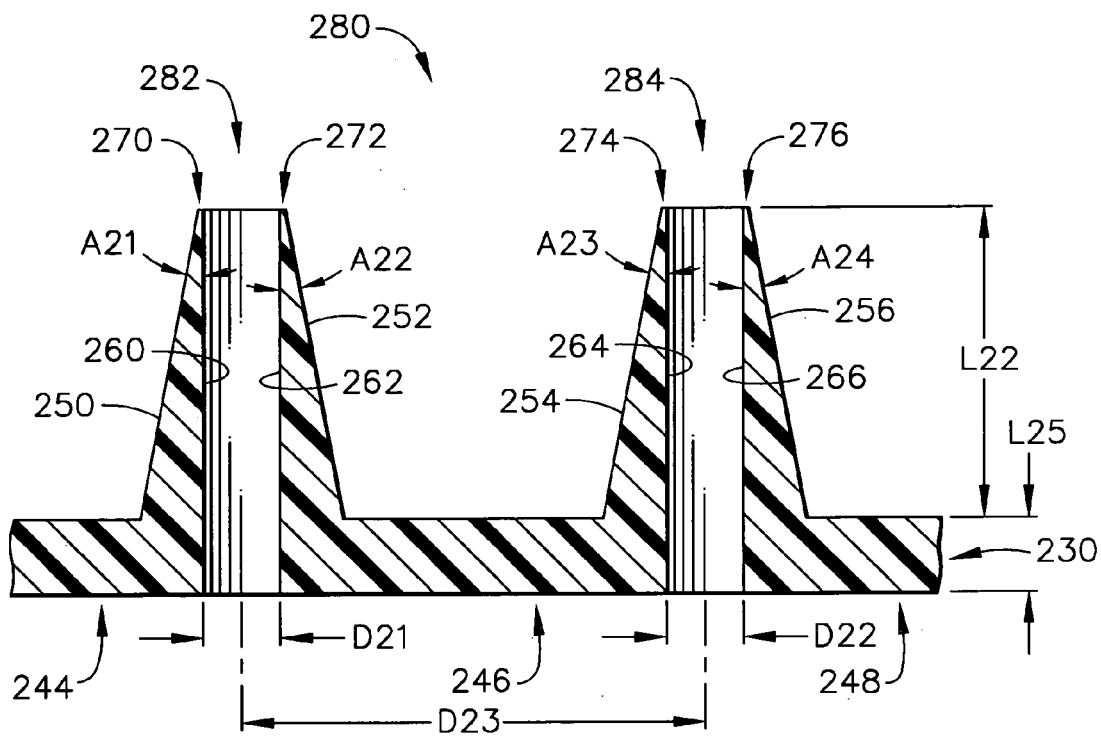
FIG. 15 is a cross-sectional view of a microneedle array of hollow microneedles constructed by the mold of FIGS. 12–14.

In FIG. 15, a microneedle array 280 has been formed out of the plastic material 230, which as viewed on FIG. 15 depicts two microneedles 282 and 284. The left-hand microneedle 282 comprises an outer conical wall as viewed at 250 and 252, and a hollow interior cylindrical wall at 260 and 262. These walls converge at the top points (as viewed on this Figure) at 270 and 272, and the convergence angle is given as "A21" and "A22." The right-hand microneedle 284 comprises an outer conical wall 254 and 256 and a hollow interior cylindrical wall 262 and 264. These walls converge at the top points (on this Figure) at 274 and 276, and the convergence angle is given as "A23" and "A24." Angles A21–A24 are preferably in the range of zero (0) to forty-five (45) degrees.

Microneedle array 280 also includes a relatively flat base structure, as indicated at the reference numerals 244, 246, and 248. This base structure has a vertical thickness as designated by the dimension L25. The microneedle height is designated by the dimension L22. The height must be sufficient to penetrate the skin through the stratum corneum and into the epidermis, and has a preferred dimension for use with interstitial fluids in the range of 50–200 microns (although, as noted above, much shorter microneedles could be constructed in this manner). The height L22 could also be a greater distance for use with other biological fluids, preferably in the range of 200–3000 microns. The thickness L25 can be of any size, however, the important criterion is that it be thick enough to be mechanically sound so as to retain the microneedle structure as it is used to penetrate the skin.

The inside diameter of the hollow microneedles is illustrated as D21 and D22, which correspond to the diameters of a cylindrical hollow opening. The distance D23 represents the separation distance between the centerlines of the two microneedles 282 and 284, in this array 280.

Figure 15A:
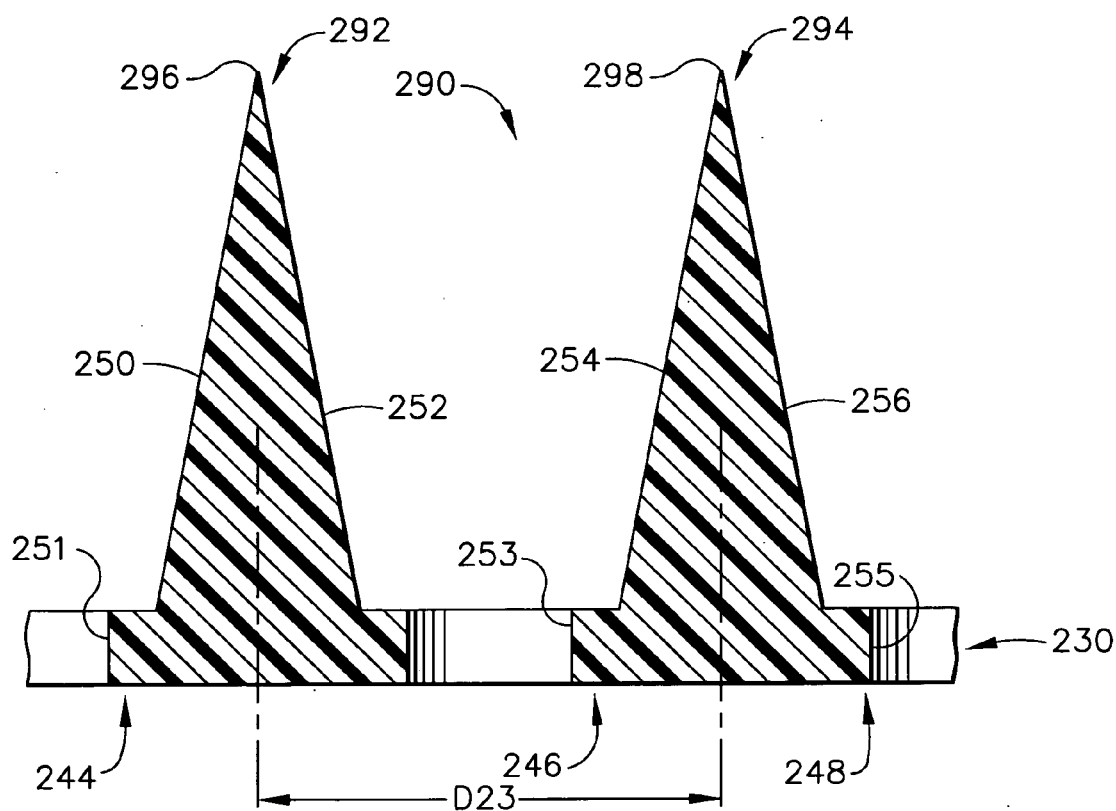
FIG. 15A is a cross-sectional view of an array of microneedles which are not hollow, and are constructed according to the mold of FIGS. 12–14 without the micropillars.

FIG. 15A represents an alternative embodiment in which a microneedle array 290 comprises "solid" microneedles 292 and 294, rather than hollow microneedles as seen at 282 and 284 on FIG. 15. These solid microneedles 292 and 294 are formed by a similar mold as viewed on FIG. 12, but with the micropillars 222 and 224 removed from this mold, and a change in shape of the microholes 213 and 217. This simple change allows the solid microneedles to be formed within conical microholes (not shown on FIG. 12), and produces a pointed conical shape, as exhibited by the outer conical wall 250 and 252 for microneedle 292, with a top pointed surface at 296. Similarly, the microneedle 294 has a conical outer wall 254 and 256, with a similar top pointed surface at 298. The other dimensions and features of the solid microneedle array 290 can be exactly the same as those features of the hollow microneedle array 280 of FIG. 15, or the dimensions may be different since this is for a different application.

The holes 251, 253, 255, can be fabricated during the microstamping or microembossing procedure via inclusion of appropriate micropillars located adjacent to the microholes 213 and 217 in FIG. 12.

Figure 16:
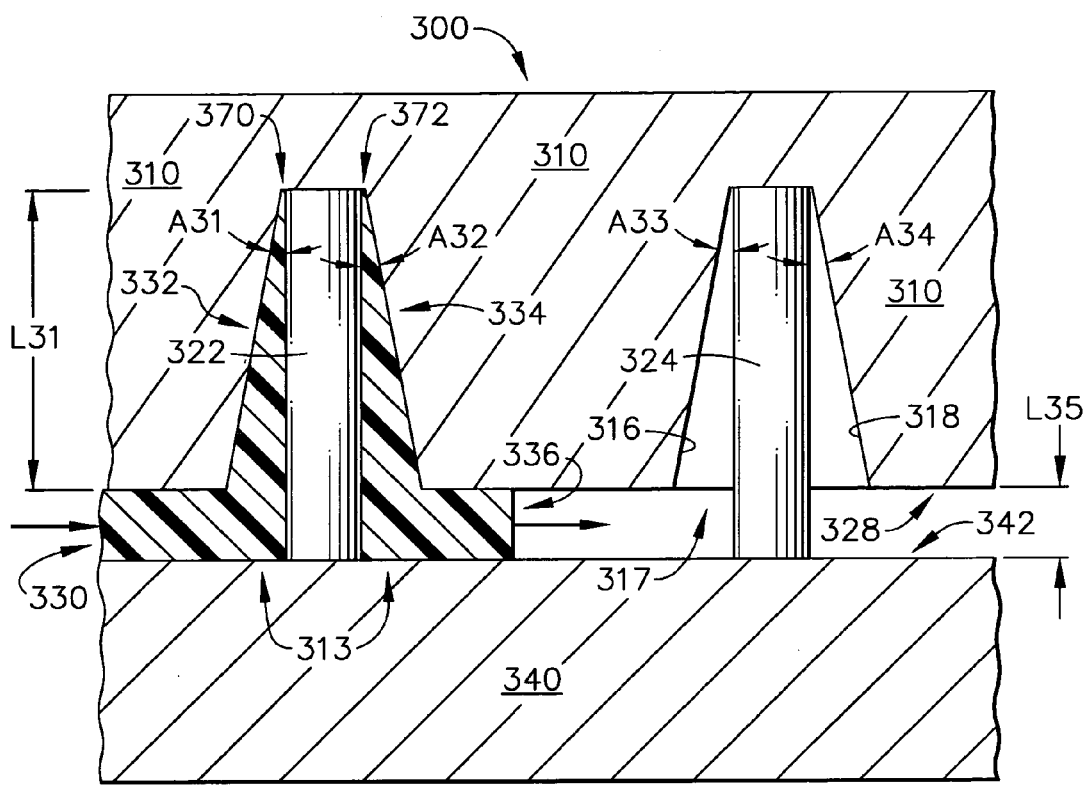
FIG. 16 is an elevational view in partial cross-section of a two-piece mold used in a microinjection method of manufacturing plastic microneedles, as constructed according to the principles of the present invention.

Referring to FIG. 16, a mold 300 consists of two mold-halves 310 and 340. These mold-halves 310 and 340 are virtually identical in shape, and probably in size, as compared to the mold-halves 210 and 240 of the mold 200 on FIG. 12. The main difference in FIG. 16 is that these mold-halves are to be used in a microinjection procedure in which molten plastic material is injected from the side at 330 into the opening between the mold-halves formed by the bottom surface 328 of the top mold-half 310 and the top surface 342 of the bottom mold-half 340.

The mold structure 300 is preferably made of a metallic material by a micro-machining process, although it could be made of a semiconductor material such as silicon or silicon carbide, if desired. On FIG. 16, the plastic material 330 is being filled from the left-hand side in this view, and has already filled a first microhole 313 with plastic material. The plastic material is illustrated as it is advancing, and has reached the point at the reference numeral 336. As time proceeds, the plastic material will reach and fill the second microhole 317, which has a conical inner wall at 316 and 318, and a corresponding micropillar 324.

At the first microhole 313, the plastic material has filled the shape around a micropillar 322 and within the conical walls of this microhole 313, to form a hollow cone having an outer wall at 332 and 334. The plastic material will be forced upward until it reaches a top point as seen at the reference numerals 370 and 372. The outer conical shape at 332 and 334 will converge with the interior shape of the micropillar 322 at an angle designated by the angles "A31"

and "A32." Microhole 317 also exhibits a converging angular shape at "A33" and "A34," which is the convergence angle between the conical walls 316 and 318 and the outer cylindrical shape of the micropillar 324.

The separation between the surfaces 328 and 342 is given by the length dimension "L35," which will become the thickness of the planar face material that will remain once the mold is opened. The vertical dimension (in FIG. 16) of the microholes is given by the dimension "L31" which preferably will create microneedles long enough to penetrate through the stratum corneum and into the epidermis, but not so long as to penetrate all the way to the dermis when used with interstitial fluids. On the other hand, for use with other biological fluids, the microneedle length will be greater, preferably in the range of 200–3000 microns, so as to penetrate into the dermis.

Figure 17:
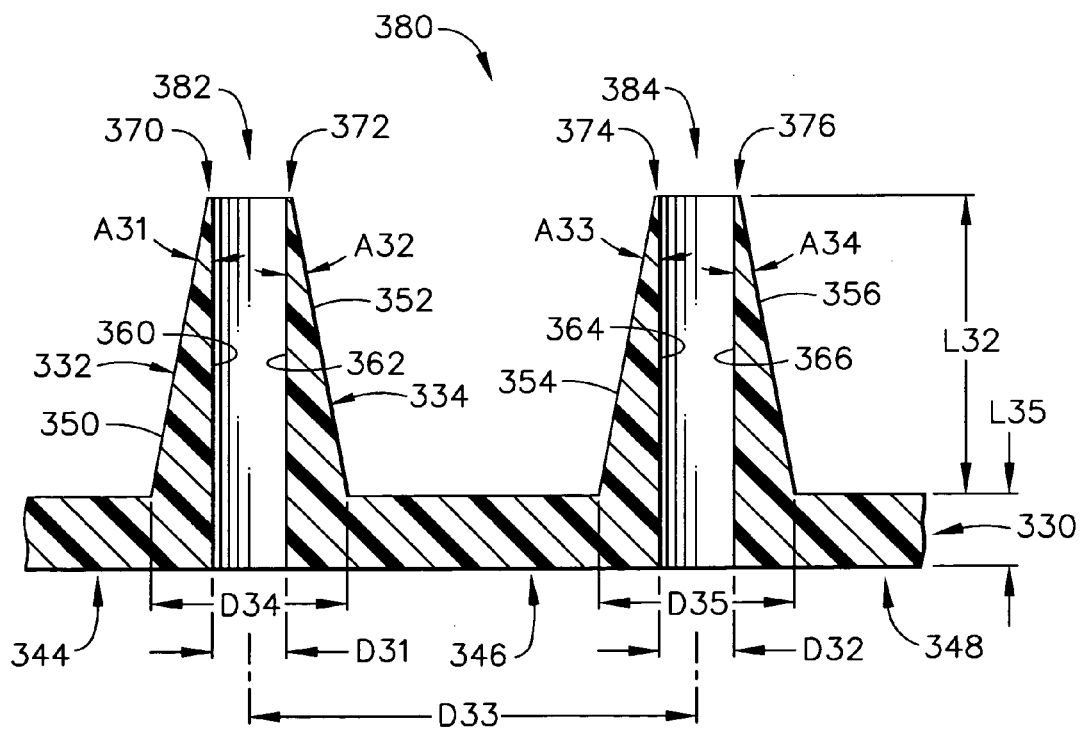
FIG. 17 is a cross-sectional view of a microneedle array of hollow microneedles constructed by the mold of FIG. 16.

FIG. 17 illustrates the microneedle array, generally designated by the reference numeral 380. On FIG. 17, two microneedles are illustrated at 382 and 384. These microneedles have a length "L32," which in theory should be exactly the same as the dimension L31 on FIG. 16, assuming the mold was properly filled with material. A preferred distance for L32 is in the range of 50–200 microns.

The plastic material 330 has a planar base structure, as illustrated at 344, 346, and 348. The thickness of this base structure is the dimension L35. The microneedles themselves exhibit a conical outer wall at 350 and 352 for the left-hand microneedle 382, and at 354 and 356 for the right-hand microneedle at 384. Each microneedle has a hollow interior, as illustrated by the cylindrical surface 360 and 362 for microneedle 382, and 364 and 366 for microneedle 384. These surfaces converge to form points (as illustrated on FIG. 17) at 370 and 372 for microneedle 382, and at 374 and 376 for microneedle 384. The convergence angle of these walls is designated by the angles A31–A34, and preferably will be in the range of zero (0) to forty-five (45) degrees.

The inner diameter of microneedle 382 is given by the dimension D31, and for microneedle 384 is given by dimension D32. These dimensions preferably are in the range 1–49, more preferably about 10 microns. The separation distance between the center lines of the microneedles is given at D33, which preferably is in the range 50–1000 microns, more preferably in the range of 100–200 microns. The height L32 is preferably in the range of 50–3000 microns and, depending upon the convergence angle A31–A34, the bottom width of the conical microneedles will vary depending upon the exact application for usage. In one preferred embodiment, this bottom dimension, designated by "D34" and "D35," will be approximately twenty (20) microns. The vertical thickness at L35 will likely be made as thin as possible, however, the important criterion is that it is sufficiently thick to be mechanically sound to hold the microneedle array 380 together as a single structure during actual usage. It is likely that, for most plastic materials that might be used in this molding procedure, the dimension L35 will be in the range of ten (10) microns through two (2) mm, or greater.

Figure 21:
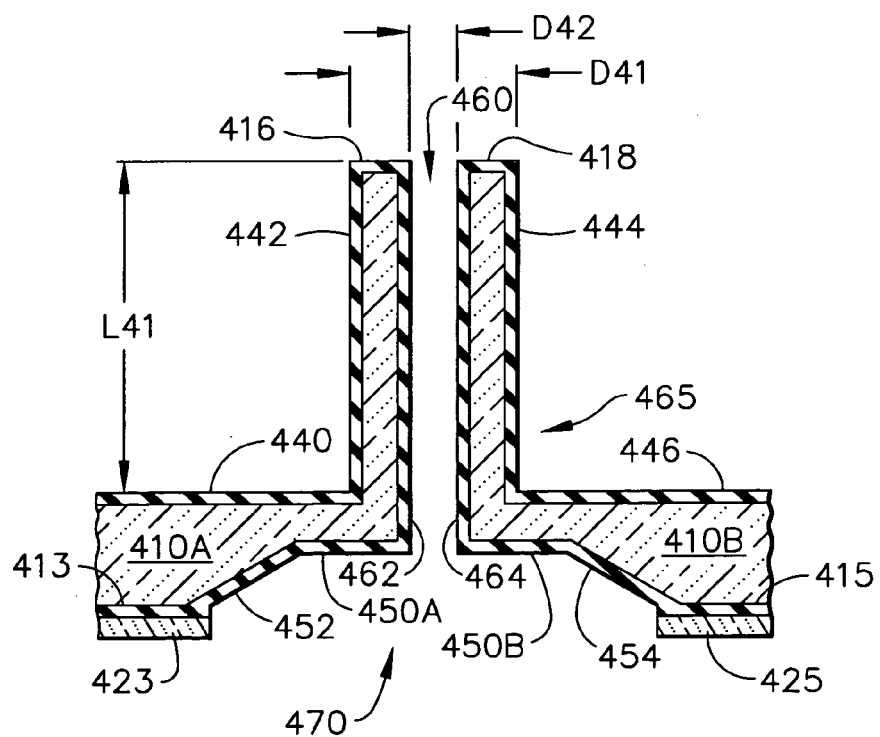
FIG. 21 is a cross-sectional view of the wafer of FIG. 20 after the silicon nitride has been removed, and after a deep reactive ion etch has created through holes, thereby resulting in a hollow microneedle.

The angular relationship between the microneedles and the corresponding planar base surface is preferably perpendicular, although an exact right angle of 90 degrees is not required. This applies to all microneedle embodiments herein described, including microneedles 62, 64 and planar surfaces 30, 32, 34 of FIG. 6, microneedles 182, 184 and planar surfaces 140, 142, 144 of FIG. 11, microneedles 282, 284 and planar surfaces 244, 246, 248 of FIG. 15, microneedles 292, 294 and planar surfaces 244, 246, 248 of FIG. 15A, microneedles 382, 384 and planar surfaces 344, 346, 348 of FIG. 17, and microneedle 470 and planar surfaces 440, 446 of FIG. 21.

It will be understood that other methods of forming plastic microneedles could be utilized to create hollow microneedles in an array, without departing from the principles of the present invention. It will also be understood that various types of materials could be used for such molding procedures, including metallic materials that might be cast using higher temperature dies of a similar shape and size, without departing from the principles of the present invention.

It will be further understood that variations in dimensions and angular relationships could be utilized to construct an array of hollow microneedles, without departing from the principles of the present invention. It will be still further understood that the angular relationship between the microneedles and their planar base surface need not be precisely perpendicular (although that configuration is preferred), but could have some variation without departing from the principles of the present invention; the microneedles also need not be exactly parallel with one another, even though that configuration is preferred.

It will be yet further understood that other microneedle shapes could be used than a cylindrical shape, if desired, without departing from the principles of the present invention. For example, the shape for hollow microneedles could prescribe a circle, ellipse, square, triangle, crescent or other arcuate path, or some other geometric structure for either the inner opening or the outer perimeter. Furthermore, the inner opening's shape could be different from the outer perimeter's shape.

Moreover, it will be understood that, with only simple modifications to the molds, an array of solid microneedles could be fabricated using the molding techniques described herein, without departing from the principles of the present invention. The outer shape for such solid microneedles could prescribe a circle, ellipse, square, triangle, crescent or other arcuate path, a star or other jagged perimeter, or some other geometric structure.

Figure 18:
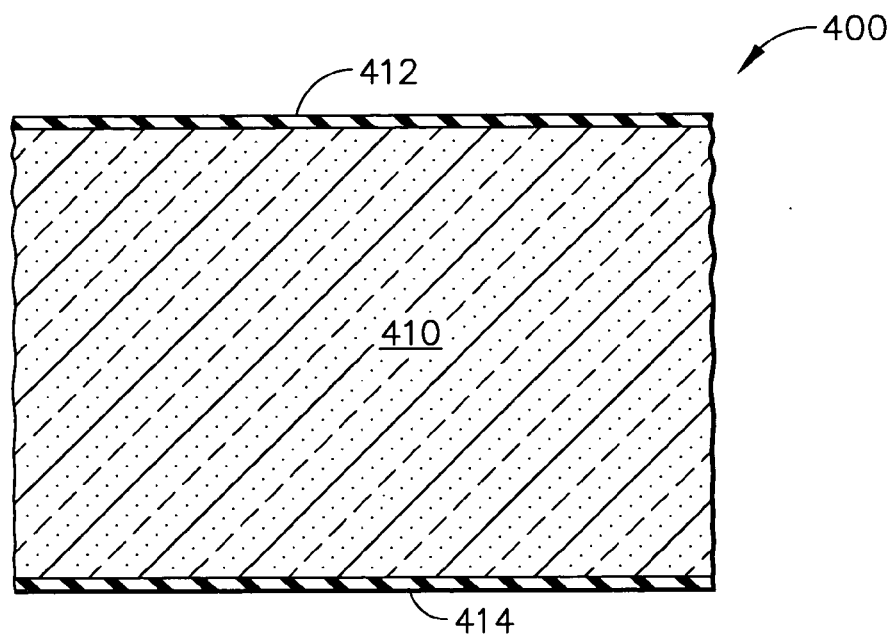
FIG. 18 is a cross-sectional view of the initial semiconductor wafer that will be formed into an array of microneedles by a microfabrication procedure, according to the principles of the present invention.

Referring now to FIG. 18, a procedure for forming dry etched microneedles will be described using an example of microfabrication (e.g., semiconductor fabrication) techniques. Starting with a single crystal silicon wafer at reference numeral 400, it is preferred to use a double side polish wafer and to grow an oxide layer on the entire outer surface. In FIG. 18, a cross-section of this wafer appears as a substrate 410, a top oxide layer 412, and a bottom oxide layer 414. Any single crystal silicon wafer will suffice, although it is preferred to use a crystal structure 100-type wafer, for reasons that will be explained below. A 110-type wafer could be used, however, it would create different angles at certain etching steps.

To create the structure depicted in FIG. 19, certain process steps must first be performed, as described below. The first step is a pattern oxide step which is performed on the top side only to remove much of the top oxide layer 412. The pattern used will create multiple annular regions comprising two concentric circles each, of which the cross-section will appear as the rectangles 416 and 418 on FIG. 19. In perspective, these annular-shaped features will have the appearance as illustrated on the perspective view of FIG. 22 at the reference numerals 416 and 418. These annular oxide patterns are the initial stages of the array locations of the multiple microneedles that will be formed on this substrate 410.

The next step is to deposit a layer of silicon nitride using a low pressure vapor deposition step, which will form a silicon nitride layer on both the top and bottom surfaces of the substrate 410. This appears as the uppermost layer 420 and the bottommost layer 422 and 424. It will be understood that the bottommost layer 422 and 424 is one continuous layer at this step, although it is not illustrated as such on FIG. 19, since a later step etches out a portion of the bottom side of the substrate between the layers 422 and 424.

Figure 19:
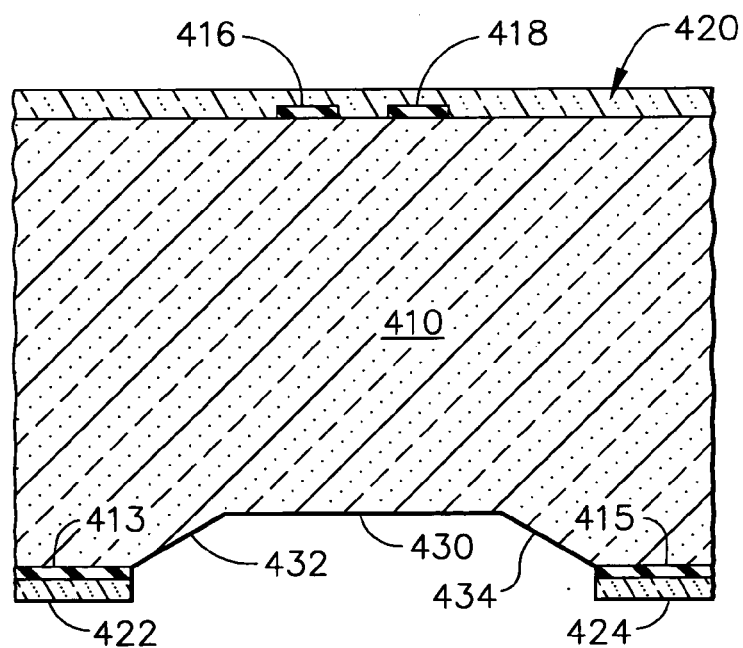
FIG. 19 is a cross-sectional view of the semiconductor wafer of FIG. 18 after a hole pattern has been established, and after a silicon nitride layer has been deposited.

Next in the process is a pattern bottom procedure in which a square hole is patterned beneath the annulus 416, 418, which is not directly visible on FIG. 19. The square holes placed by the pattern bottom procedure are now used in a KOH etching step that is applied to the bottom side only of the substrate 410. This KOH etching step creates a window along the bottom of the substrate as viewed along the surfaces 432, 430, and 434 on FIG. 19. This window interrupts the oxide layer 414 along the bottom of substrate 410, and divides it (on FIG. 19) into two segments 413 and 415. This window (or hole) also interrupts the silicon nitride layer into two segments (on FIG. 19) 422 and 424.

The slope angle of the etched window along surfaces 432 and 434 is 54.7 degrees, due to the preferred 100-type silicon material. If type-110 silicon material was used, then this slope would be 90 degrees. That would be fine, however, crystalline silicon 100-type material is less expensive than silicon 110-type material. After the KOH time etching step has been completed, the silicon wafer will have the appearance as depicted in FIG. 19.

The next fabrication operation is to perform a pattern top nitride procedure using a photoresist mask. This removes the entire upper silicon nitride layer 420 except where the photoresist mask was located, which happens to be aligned with the upper oxide annulus at 416 and 418. The remaining upper silicon nitride is indicated at the reference numeral 426 on FIG. 20, although at this stage in the fabrication procedure, the upper surface will still be a planar surface at the level of the oxide layer 416 and 418, across the entire horizontal dimension of FIG. 20.

The next fabrication step is to perform a deep reactive ion etch (DRIE) operation on the top surface of the substrate 410, which will etch away a relatively deep portion of the upper substrate except at locations where the silicon nitride layer still remains, i.e., at 426. In this DRIE procedure, it is preferred to remove approximately 50–70 microns of material. After that has occurred, the remaining photoresist mask material is removed. This now exposes the top silicon nitride layer 426.

The next fabrication step is to oxidize all of the bare silicon that is now exposed along the outer surfaces. This will form a layer of silicon dioxide at locations on FIG. 20, such as at 440, 442, 444, 446, 452, 450, and 454. The outer silicon nitride layers at 426, 423, and 425 are not oxidized. The outer silicon nitride layers 423 and 425 are essentially the same structures as layers 422 and 424 on FIG. 19, although the silicon dioxide layers 452 and 454 are now formed above these "pads" 423 and 425. It is preferred that this oxidation be a minimal amount, just enough for a future DRIE masking procedure, and that the oxidized thickness be approximately 5,000 Angstroms. At this point in the fabrication procedure, the silicon wafer has the appearance of that depicted in FIG. 20.

Figure 20:
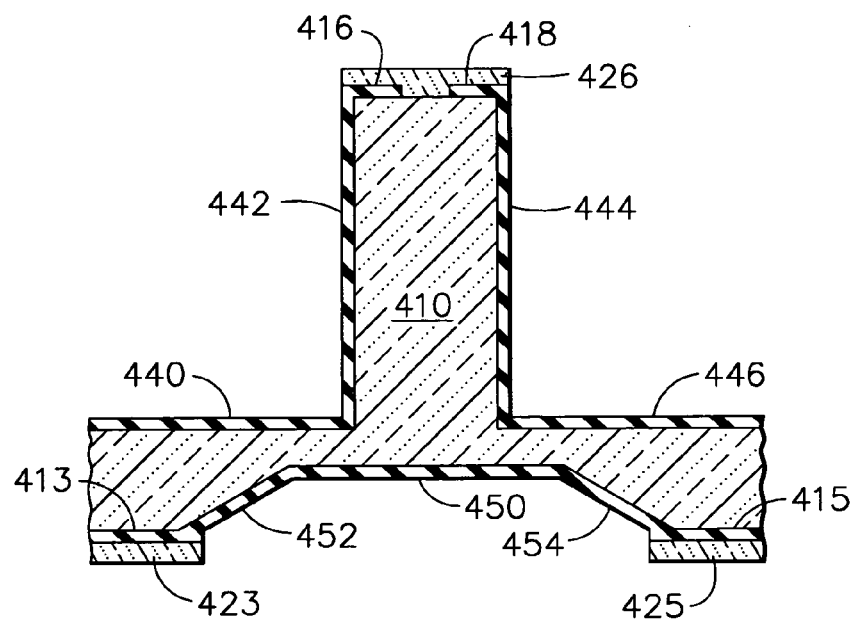
FIG. 20 is a cross-sectional view of the wafer of FIG. 18 after a photoresist mask operation, a deep reactive ion etch operation, and an oxidize operation have been performed.

The next step in the fabrication procedure is to remove the silicon nitride layer on the top, which will remove the layer at 426 as seen on FIG. 20. This will expose a circular region in the very center of the annulus such that pure silicon is now the outermost material on the top side of the wafer. After that has occurred, a deep reactive ion etch operation is performed to create a through-hole at the reference numeral 460 on FIG. 21. After this step has been performed, there will be pure silicon exposed as the inner wall of the through-hole 460. Therefore, the next step is to oxidize the entire wafer, which will place a thin cylindrical shell of silicon dioxide around the inner diameter of through-hole 460, and this oxidized layer is viewed on FIG. 21 at 462 and 464.

After these steps have been performed, a microneedle 465 is the result, having an outer diameter at "D41," and an inner diameter through-hole at "D42." It is preferred that the inner diameter D42 have a distance in the range of 5–10 microns. The height of the microneedle is given at the dimension "L41," which has a preferred dimension in the range of 50–200 microns. On FIG. 21, the substrate 410 has been divided into halves at 410A and 410B. In addition, the bottom oxide layer 450 has been divided in halves at 450A and 450B.

The bottom chamber formed by the sloped surfaces 452 and 454, in combination with the horizontal surfaces 450A and 450B, act as a small, recessed storage tank or chamber generally indicated by the reference numeral 470. This chamber 470 can be used to store a fluid, such as insulin, that is to be dispensed through the cylindrical opening 460 in the hollow microneedle 465. At the scale of FIG. 21, this chamber is not very large in overall physical volume, and it normally would be preferred to interconnect all of such chambers for each of the microneedles in the overall array so that a common fluid source could be used to dispense fluid to each of these chambers 470. Furthermore, there may be a need to dispense a physically much larger volume of fluid, and it also may be desirable to provide a pressure source, such as a pump. In such situations, it may be preferable to have an external storage tank that is in communication with each of the fluid chambers 470 on the wafer that is used to make up the array of microneedles, such as microneedle 465.

Figure 22:
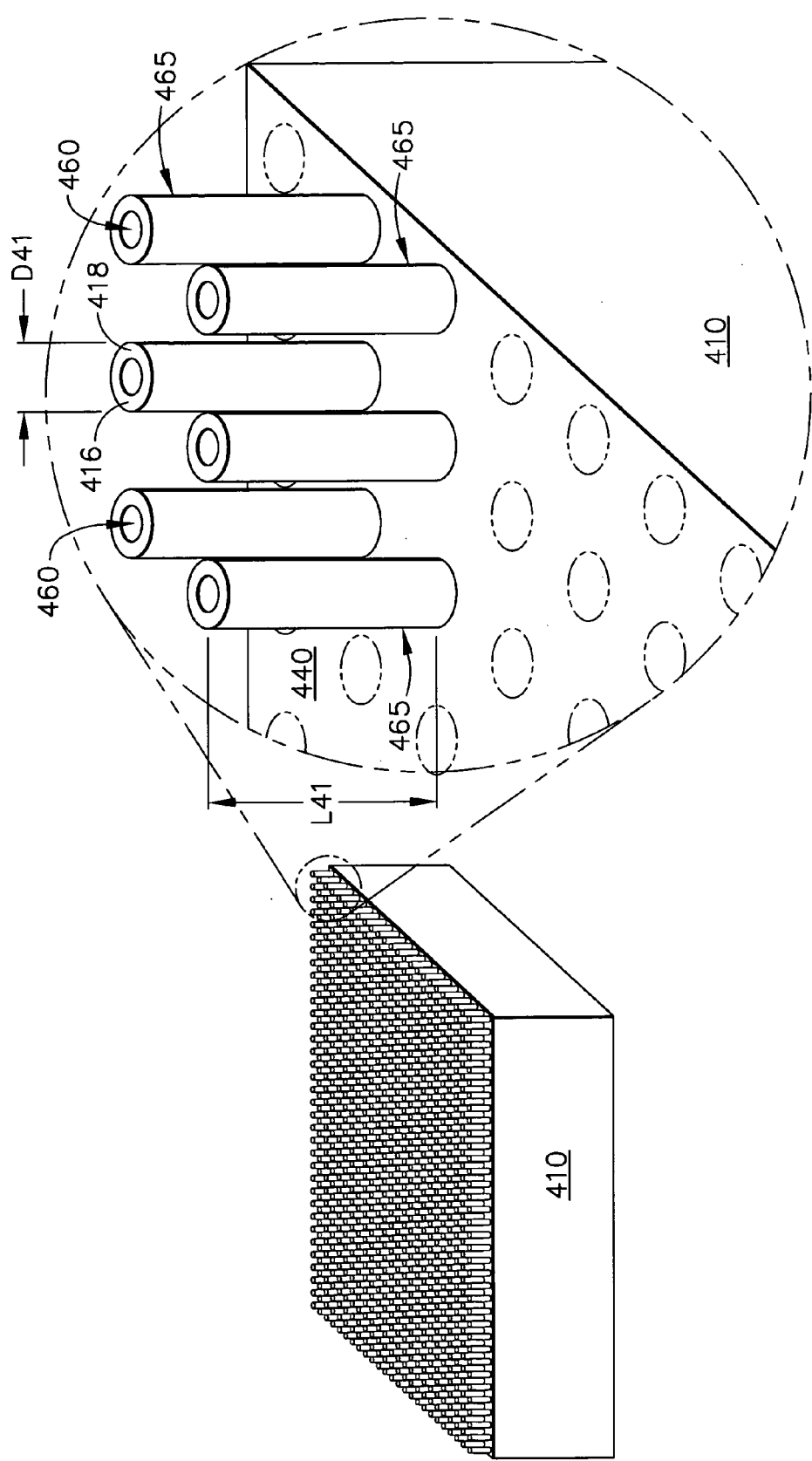
FIG. 22 is a perspective view of a microneedle array on a semiconductor substrate, including a magnified view of individual cylindrical microneedles.

FIG. 22 depicts an array of microneedles on substrate 410, and also illustrates a magnified view of some of these microneedles 465. Each microneedle 465 exhibits a cylindrical shape in the vertical direction, and has an outer diameter D41, an annular shaped upper surface at 416 and 418, and a through-hole at 460. Each of the microneedles 465 extends out from the planar surface 440 of the substrate 410.

As can be seen in FIG. 22, substrate 410 can either be made much larger in height so as to have a very large internal volume for holding a fluid substance, or the substrate itself could be mounted onto a different material that has some type of fluidic opening that is in communication with the chambers 470 of the individual microneedles 465.

It will be understood that other semiconductor substances besides silicon could be used for the fabrication of the array of microneedles depicted on FIG. 22, without departing from the principles of the present invention. Furthermore, the microneedles could be coated with materials such as silicon carbide to impart additional strength. Moreover, other microneedle shapes could be used than a cylindrical shape with an annular top surface, and in fact, the top surface of such microneedles could be sloped to create a sharper edge, if desired, without departing from the principles of the present invention.

It will also be understood that the preferred dimensions discussed hereinabove are only preferred, and any microneedle length or diameter that is appropriate for a particular chemical fluidic compound and for a particular skin structure could be used without departing from the principles of the present invention. As discussed above, for use with interstitial body fluids it is preferred that the microneedle penetrate through the stratum corneum into the epidermis, but not penetrate into the dermis itself. This means that such microneedles would typically be no longer than two hundred (200) microns, though they must typically be at least fifty (50) microns in length. However, for use with other biological fluids, a useful length is in the range of 200 microns–3 mm, and more preferably in the range of 200–400 microns. Of course, if cosmetic applications were desired, then the microneedle could be much shorter in length, even as short as one (1) micron. Finally, it will be understood that any size or shape of fluid-holding chamber could be used in a drug-delivery system, which will be further discussed hereinbelow. In addition, for a body-fluid sampling system, a fluid-holding chamber would also preferably be in communication with the through-holes 460 of each of the microneedles 465.

Figure 23:
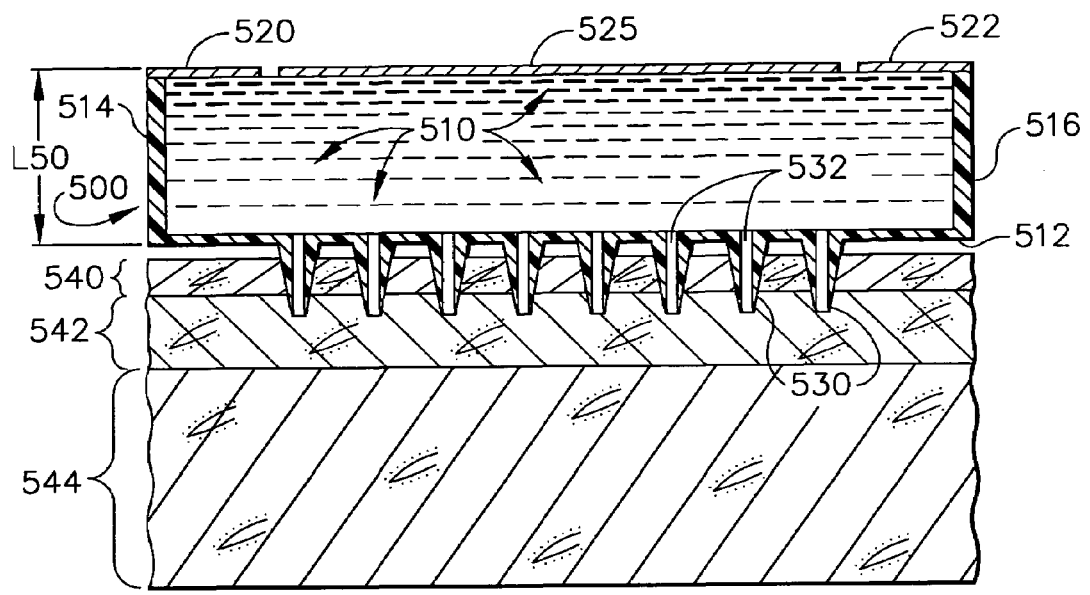
FIG. 23 is a cross-sectional view of an electrophoretically enhanced body-fluid sensor, based upon a hollow microneedle array, as constructed according to the principles of the present invention.

FIG. 23 depicts an electrophoretically enhanced body-fluid sensor that is based upon a hollow microneedle array, generally designated by the reference numeral 500. Sensor 500 includes a plurality of microneedles 530, which are each hollow, having a vertical opening throughout, as indicated at 532. A fluid chamber 510 is in communication with the hollow portions 532 of the array of microneedles 530. Of course, other fluid driving mechanisms could be used as well, such as passive diffusion (e.g., time release), instantaneous injection, pressure, vacuum, or ultrasound.

Fluid chamber 510 is constructed of a bottom (in FIG. 23) planar surface 512—which has openings that are aligned with the microneedles 530—a left vertical wall 514, and a right vertical wall 516. The top (or ceiling) of the fluid chamber 510 is made up of a planar material which is divided into individual electrodes. The middle electrode 525 is part of the fluid sensor, and makes it possible to measure a current or voltage within the fluid chamber 510. Electrodes 520 and 522 are electrically connected to one another (and can be of a single structure, such as an annular ring) so as to act as the electrophoretic electrodes (i.e., as either an anode or a cathode) that facilitate the transport of fluid through the hollow microneedles 530 from the skin into the fluid chamber 510.

The height of the fluid chamber structure is designated as "L50," which could be any reasonable dimension that is large enough to hold a sufficient volume of fluid for a particular application. Of course, if desired, the fluid chamber 510 could be connected to a much larger external reservoir (not shown), and a pump could even be used if pressure or vacuum is desired for a particular application.

The layer 540 represents the stratum corneum, the layer 542 represents the viable epidermis, and the largest layer 544 represents the dermis, which contains nerves and capillaries.

The application of microneedles 530 into the stratum corneum 540 and epidermis 542 decreases the electrical resistance of the stratum corneum by a factor of approximately fifty (50). The applied voltage, therefore, during electrophoresis (e.g., iontophoresis) or electroosmosis can be greatly reduced, thereby resulting in low power consumption and improved safety. Iontophoresis provides the necessary means for molecules to travel through the thicker dermis into or from the body. The combination of the microneedles and the electric field that is applied between the electrodes 520 and 522 (acting as an anode, for example) and a remotely placed electrode (e.g., electrode assembly 505, viewed on FIG. 25, and acting as a cathode, for example) provides for an increase in permeability for both the stratum corneum and the deeper layers of skin.

While the transport improvement in stratum corneum is mostly due to microneedle piercing, the electrophoresis provides higher transport rates in the epidermis and dermis. This is not only true for small sized molecules, but also for the larger and more complex useful molecules.

The body-fluid sampling sensor 500 can be used for a continuous non-invasive measurement of blood glucose level, for example. Glucose is extracted through the skin by reverse iontophoresis, and its concentration is then characterized by a bioelectrochemical sensor. The sensor comprises the chamber 510 that is filled with hydrogel and glucose oxidase, and the electrode 525. The glucose molecules are moved from the body by the flow of sodium and chloride ions caused by the applied electric potential. The detection of the glucose concentration in the hydrogel pad is performed by the bioelectrochemical sensor.

Figure 24:
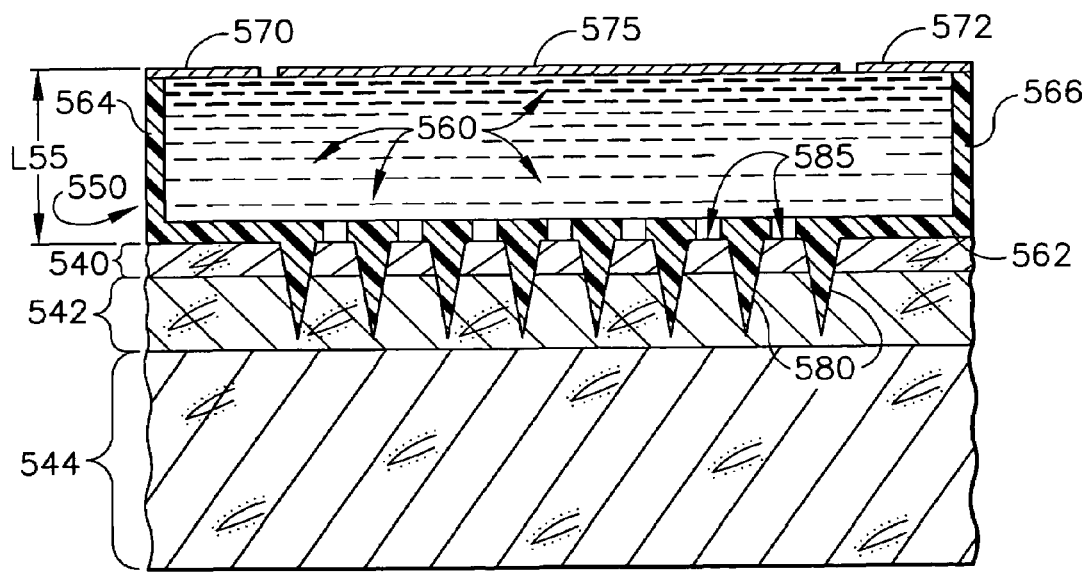
FIG. 24 is a cross-sectional view of an electrophoretically enhanced body-fluid sensor, based upon a solid microneedle array, as constructed according to the principles of the present invention.

An alternative embodiment 550 is depicted in FIG. 24, in which the microneedles 580 are solid, rather than hollow. A fluid-filled chamber 560 is provided and also comprises hydrogel filled with glucose oxidase. The chamber 560 is made of a bottom wall 562 that has openings proximal to the individual microneedles 580, in which these openings are designated by the reference numeral 585. Chamber 560 also includes side walls 564 and 566, as well as electrodes 570, 572, and 575.

The electrode 575 is constructed as part of the bioelectrochemical sensor. The electrodes 570 and 572 act as the electrophoretic electrodes, acting either as an anode or cathode to set up an electric current through the skin which flows to a remotely-attached (to the skin) electrode (e.g., electrode assembly 555, viewed on FIG. 26).

As in the sensor 500 of FIG. 23, the transport rate of fluids is enhanced by not only the piercing effect of the microneedles 580, but also the electric field inducing a current through the skin. In the glucose sampling example, glucose is attracted into the chamber 560, and its concentration is measured by the bioelectrochemical sensor.

The height of the fluid chamber structure is designated as "L55," which could be any reasonable dimension that is large enough to hold a sufficient volume of fluid for a particular application. Of course, if desired, the fluid chamber 560 could be connected to a much larger external reservoir (not shown), and a pump could even be used if pressure or vacuum is desired for a particular application.

Figure 25:
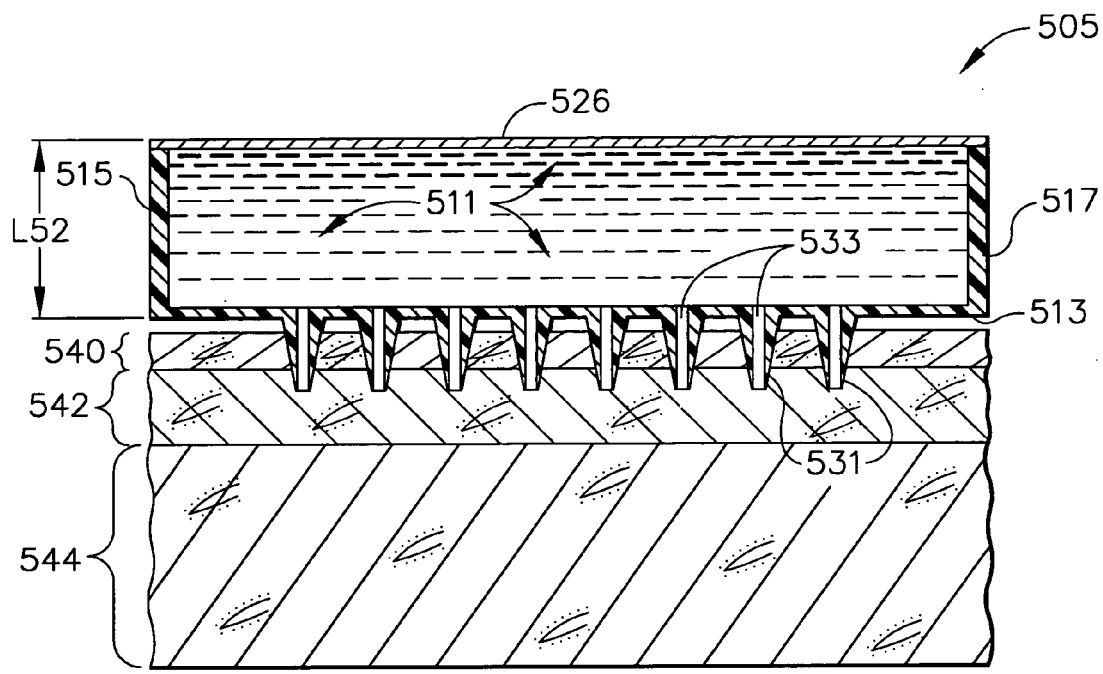
FIG. 25 is a cross-sectional view of an electrode, based upon a hollow microneedle array, as constructed according to the principles of the present invention.

FIG. 25 depicts an electrophoretic electrode assembly that is based upon a hollow microneedle array, generally designated by the reference numeral 505. Electrode assembly 505 includes a plurality of microneedles 531, each being hollow and having a vertical opening throughout, as indicated at 533. A fluid chamber 511 is in communication with the hollow portions 533 of the array of microneedles 531.

Fluid chamber 511 is constructed of a bottom planar surface 513—which has openings that are aligned with the microneedles 531—a left vertical wall 515, and a right vertical wall 517. The top (or ceiling) of fluid chamber 511 is made of a planar electrode material 526. The electrode 526 is to be electrically connected to a low-current voltage source (not shown on FIG. 25), either through a substrate pathway (such as a integrated circuit trace or a printed circuit foil path) or a wire (also not shown on FIG. 25).

The height of the fluid chamber 511 is given by the dimension "L52," which can be of any practical size to hold a sufficient amount of hydrogel, for example, to aid in the conduction of current while acting as the electrode. In electrode assembly 505, the fluid within chamber 511 preferably would not be electrically charged.

As can be seen in FIG. 25, the hollow microneedles 531 penetrate the stratum corneum 540 and into the viable epidermis 542. The microneedles 531 preferably will not be sufficiently long to penetrate all the way to the dermis 544.

Figure 26:
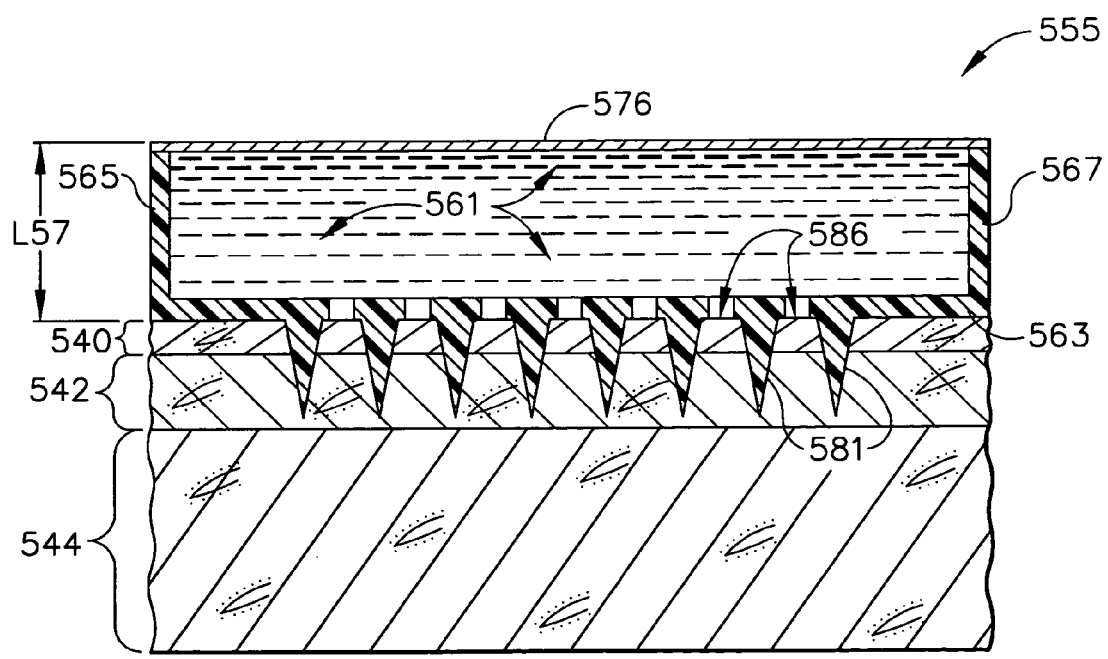
FIG. 26 is a cross-sectional view of an electrode, based upon a solid microneedle array, as constructed according to the principles of the present invention.

An alternative embodiment 555 is depicted in FIG. 26, in which the microneedles 581 are solid, rather than hollow. A fluid chamber 561 is provided and preferably is filled with hydrogel (which is not electrically charged). Chamber 561 is made of a bottom wall 563 that has openings proximal to the individual microneedles 581, in which these openings are designated by the reference numeral 586. Chamber 561 also includes side walls 565 and 567, as well as a top (or ceiling) electrode 576. The electrode 576 may act as a cathode, for example, in a situation where electrode assembly 555 is being used in conjunction with a body-fluid sensor, such as sensor assembly 550 viewed on FIG. 24, in which its electrodes 570 and 572 may act, for example, as an anode. The height "L57" of fluid chamber 561 could be any reasonable dimension that is large enough to hold a sufficient volume of the hydrogel to enhance the fluid flow via the electric field between the respective anode and cathode of the system.

Figure 27:
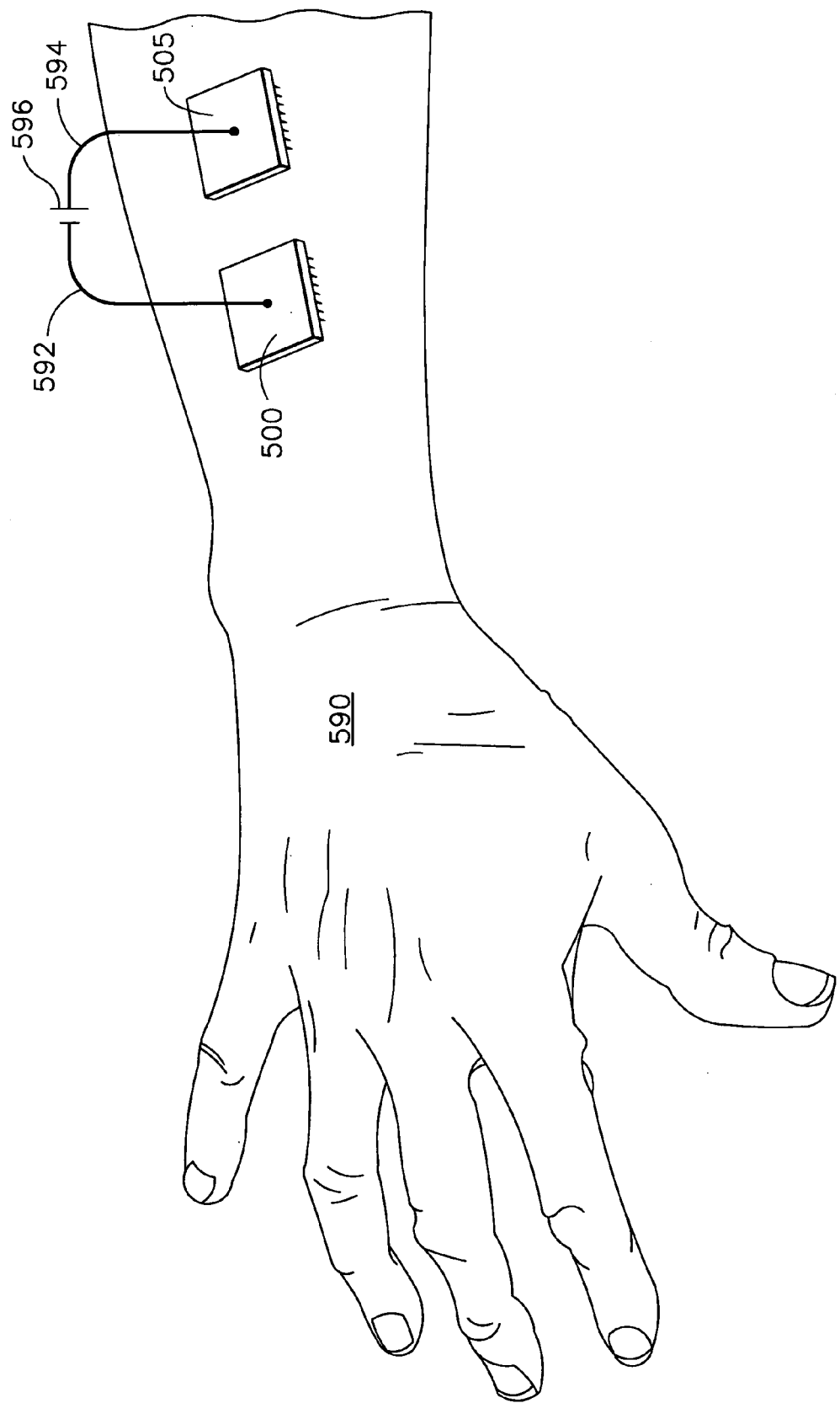
FIG. 27 is a perspective view of a sensing system attached to a human hand and forearm, which includes an electrophoretically enhanced body-fluid sensor as per FIG. 23 and an electrode as per FIG. 25.

FIG. 27 illustrates a portion of a human arm and hand 590, along with a drug delivery electrode assembly 500 and a second electrode assembly 505. Both electrodes are attached to the skin of the human user, via their microneedles, such as the hollow microneedles 530 (viewed on FIG. 23) and the hollow microneedles 531 (viewed on FIG. 25).

Since an electrical voltage is applied between the two electrode assemblies 500 and 505, it is preferred to use a low current power supply, generally designated by the reference numeral 596, that is connected to each of the electrodes via a wire 592 or a wire 594, respectively. It will be understood that any type of physical electrical circuit could be used to provide the electrical conductors and power supply necessary to set up an appropriate electrical potential, without departing from the principles of the present invention. In fact, the electrode assemblies and wiring, along with an associated power supply, could all be contained on a single apparatus within a substrate, such as that viewed on FIGS. 30 and 31 herein, or by use of printed circuit boards.

Figure 28:
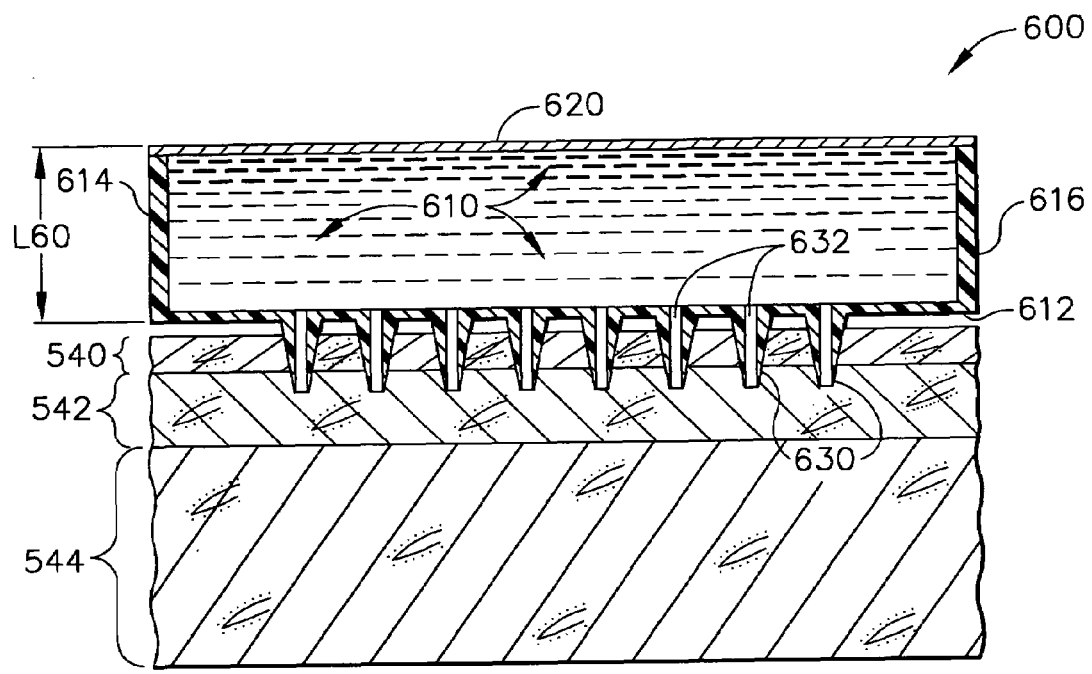
FIG. 28 is a cross-sectional view of an electrophoretically enhanced drug delivery system, based upon a hollow microneedle array, as constructed according to the principles of the present invention.

FIG. 28 depicts an electrophoretically enhanced fluidic drug delivery apparatus that is based upon a hollow microneedle array, generally designated by the reference numeral 600. Drug-delivery apparatus 600 includes a plurality of microneedles 630, which are each hollow, having a vertical opening throughout, as indicated at 632. A fluid chamber 610 is in communication with the hollow portions 632 of the array of microneedles 630.

Fluid chamber 610 is constructed of a bottom (in FIG. 28) planar surface 612—which has openings that are aligned with the microneedles 630—a left vertical wall 614, and a right vertical wall 616. The top (or ceiling) of the fluid chamber 610 is made up of a planar material 620 that acts as an electrode. Electrode 620 is part of the drug delivery apparatus, and makes it possible to induce a current flow through fluid chamber 610. Electrodes 620 and 622 are connected so as to act as the electrophoretic electrodes (i.e., as either an anode or a cathode) that facilitate the transport of fluid through the hollow microneedles 630 from the fluid chamber 610 into the skin.

The height of the fluid chamber structure is designated as "L60," which could be any reasonable dimension that is large enough to hold a sufficient volume of fluid for a particular drug delivery application. Of course, if desired, the fluid chamber 510 could be connected to a much larger external reservoir (not shown), and a pump could even be used if pressure or vacuum is desired for a particular application.

The layer 540 represents the stratum corneum, the layer 542 represents the viable epidermis, and the largest layer 544 represents the dermis, which contains nerves and capillaries.

The application of microneedles 630 into the stratum corneum 540 and epidermis 542 decreases the electrical resistance of the stratum corneum by a factor of approximately fifty (50). The applied voltage, therefore, during electrophoresis (e.g., iontophoresis) can be greatly reduced, thereby resulting in low power consumption and improved safety. Iontophoresis provides the necessary means for molecules to travel through the thicker dermis into or from the body. The combination of the microneedles and the electric field that is applied between the electrodes 620 and 622 (acting as anodes, for example), and another electrode (e.g., electrode assembly 505, acting as a cathode) that is attached elsewhere on the skin of the user, provides for an increase in permeability for both the stratum corneum and the deeper layers of skin. While the transport improvement in stratum corneum is mostly due to microneedle piercing, the electrophoresis provides higher transport rates in the epidermis and dermis. This is not only true for small sized molecules, but also for the larger and more complex useful molecules.

The drug delivery apparatus 600 can be used for a continuous non-invasive medical device that can continuously deliver a fluidic drug through the skin and into the body. For example, insulin could be delivered to the blood stream via the microneedles 531, through the stratum corneum 540 and epidermis 542, and also into the dermis 544 where the insulin would be absorbed into the capillaries (not shown).

Figure 29:
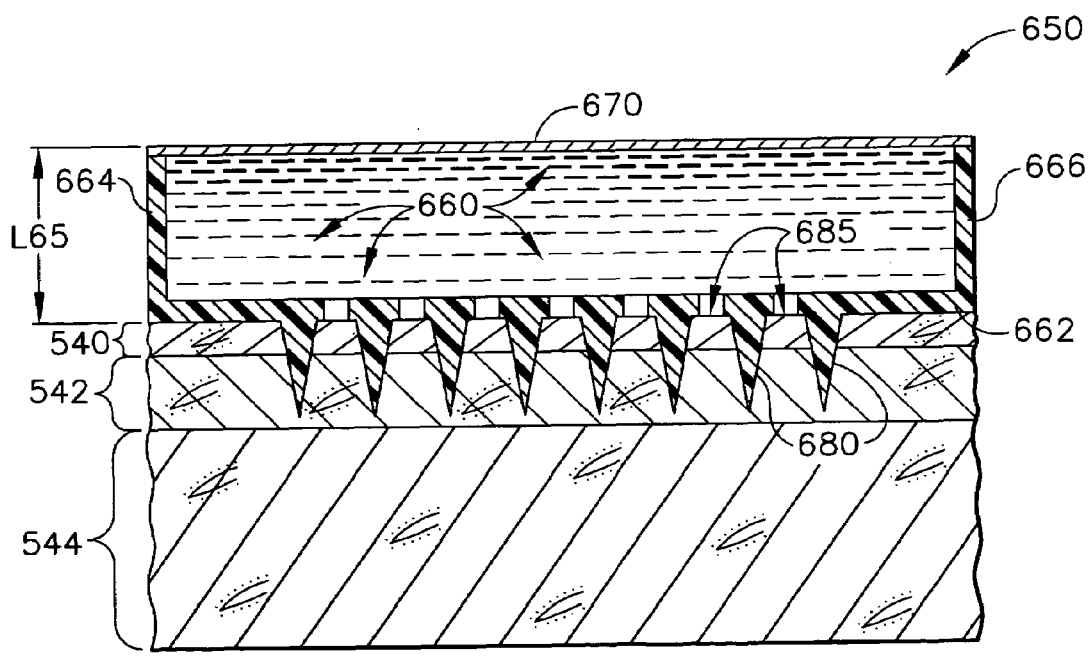
FIG. 29 is a cross-sectional view of an electrophoretically enhanced drug delivery system, based upon a solid microneedle array, as constructed according to the principles of the present invention.

An alternative embodiment 650 is depicted in FIG. 29, in which the microneedles 680 are solid, rather than hollow. A fluid-filled chamber 660 is provided and also contains hydrogel. Chamber 660 is made of a bottom wall 662 that has openings proximal to the individual microneedles 680, in which these openings are designated by the reference numeral 685. Chamber 660 also includes side walls 664 and 666, as well as electrodes 670, 672, and 675.

The electrode 675 is constructed as part of the bioelectrochemical sensor. The electrodes 670 and 672 act as the electrophoretic electrodes, acting either as the anode or cathode to set up an electric current through the skin, in conjunction with another electrode assembly (such as electrode assembly 655, viewed on FIG. 26) placed elsewhere on the user's skin.

As in the drug delivery apparatus 600 of FIG. 28, the transport rate of fluids is enhanced by not only the piercing effect of the microneedles 680, but also the electric field inducing a current through the skin. In the insulin dispensing example, insulin is repelled from the chamber 660, and therefore, flows out through openings 685 proximal to microneedles 680, then into the user's skin.

The height of the fluid chamber structure is designated as "L65," which could be any reasonable dimension that is large enough to hold a sufficient volume of fluid for a particular application. Of course, if desired, the fluid chamber 660 could be connected to a much larger external reservoir (not shown), and a pump could even be used if pressure or vacuum is desired for a particular application.

Figure 30:
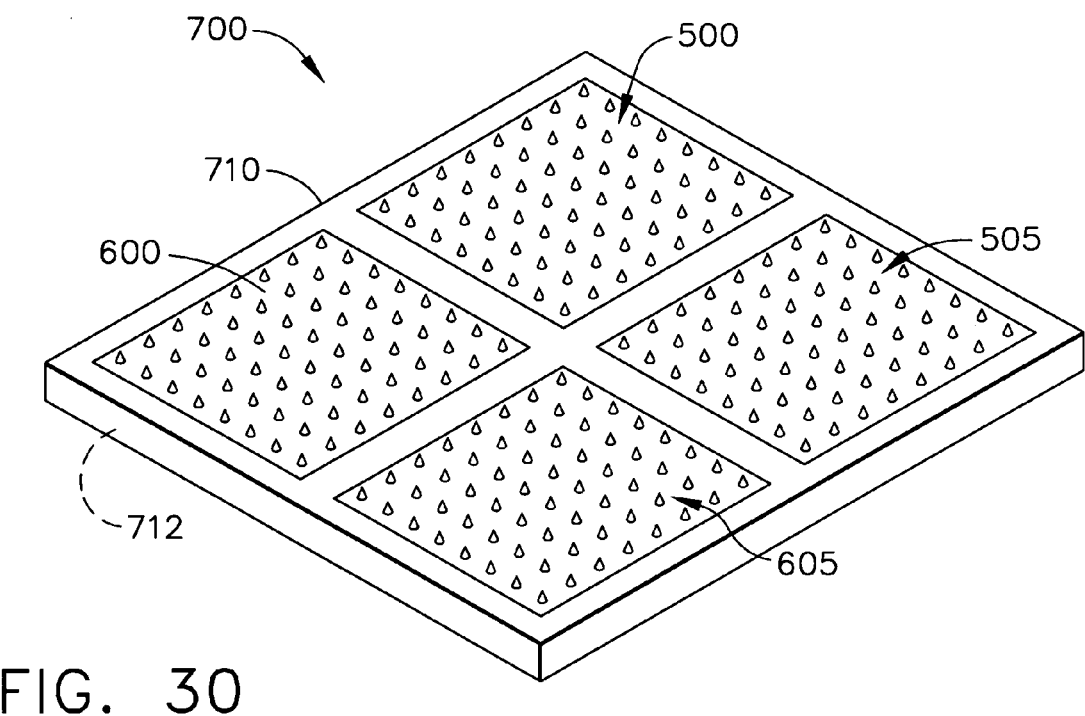
FIG. 30 is a perspective view of a closed-loop drug-delivery system, as viewed from the side of a patch that makes contact with the skin, as constructed according to the principles of the present invention.

FIG. 30 depicts a closed-loop drug-delivery system generally designated by the reference numeral 700. This closed-loop system 700 includes a pair of electrophoretic pads, generally designated by the reference numerals 500 and 505, which each include an array of microneedles for fluid sampling. Pad 500 comprises a sensor assembly (as described hereinabove with respect to FIG. 23), and pad 505 comprises an electrode assembly (as described hereinabove with respect to FIG. 25).

Closed-loop system 700 also includes a pair of electrophoretic pads, generally designated by the reference numerals 600 and 605, that each include an array of microneedles for drug delivery. Pad 600 comprises a drug delivery apparatus (as described hereinabove with respect to FIG. 28), and pad 505 comprises an electrode assembly (as described hereinabove with respect to FIG. 25). Of course, electrophoretic pads having solid microneedles could instead be used, such that pads 500 and 600 (with hollow microneedles) could be replaced by pads 550 and 650 (with solid microneedles), and pad 505 (with hollow microneedles) could be replaced by a pad 555 (with solid microneedles).

Pads 500 and 600 are mounted to a substrate 710, which can be made of either a solid or a somewhat flexible material. Within substrate 710 preferably resides a reservoir 712 (within the substrate 710) that holds the fluid which is to be dispensed through the microneedles of pads 600. Reservoir 712 could be made up of individual "small" chambers, such as a large number of chambers 610 that are connected to a source of fluidic drug.

Figure 31:
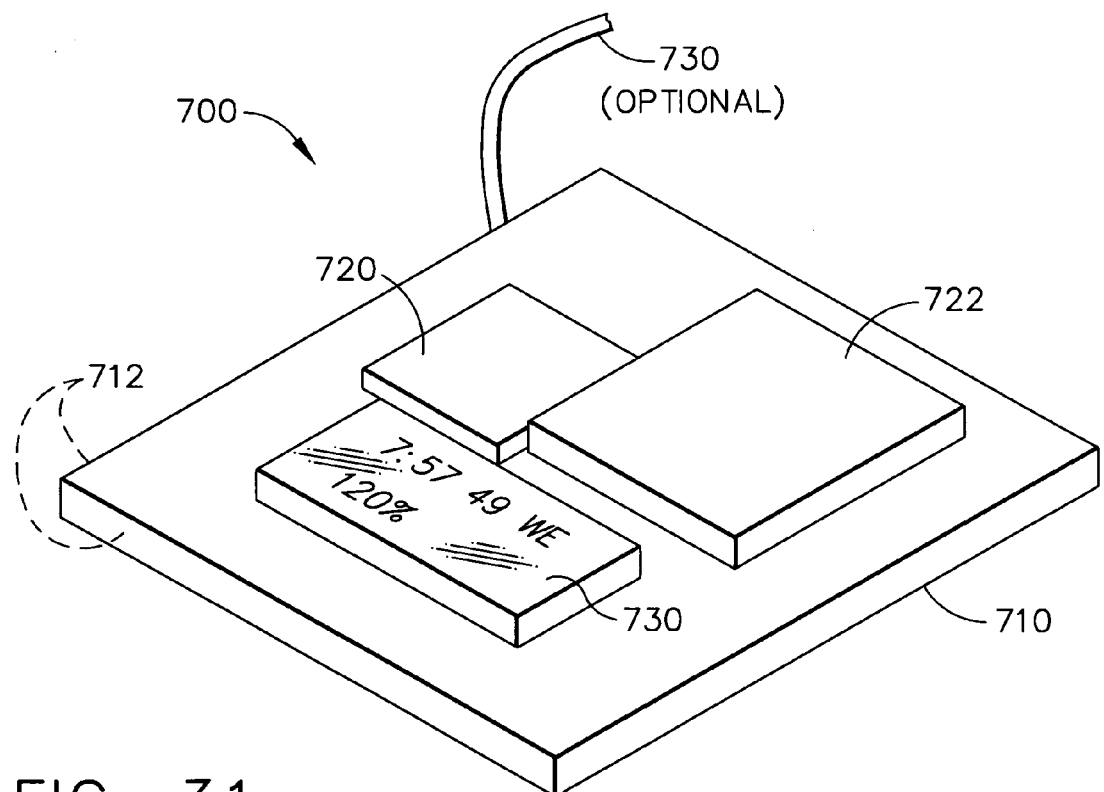
FIG. 31 is a perspective view of the closed-loop drug-delivery system of FIG. 30, as seen from the opposite side of the patch.

It will be understood that the reservoir 712 preferably is completely contained within substrate 710, and cannot be seen from this view of FIG. 31. As an alternative, however, a fluid channel (such as a flexible tube at 730) could be connected into substrate 710 and, by use of a pump (not shown), further quantities of the fluid could be provided and dispensed through the microneedles of pads 600, using fluidic pressure.

FIG. 31 illustrates the opposite side of the closed-loop system 700. A controller 720 is mounted to the upper surface (in this view) of substrate 710. Controller 720 preferably comprises a type of microchip that contains a central processing unit that can perform numeric calculations and logical operations. A microprocessor that executes software instructions in a sequential (or in a parallel) manner would be sufficient. A microcontroller integrated circuit would also suffice, or an ASIC that contains a microprocessor circuit.

Adjacent to controller 720 is an electrophoretic power supply with a battery, the combination being generally designated by the reference numeral 722. In addition, a visual indicator can be placed on the surface of the substrate, as at 730. This visual indicator could give a direct reading of the quantity of interest, such as glucose concentration, or some other body-fluid parameter. The visual indicator preferably comprises a liquid crystal display that is capable of displaying alphanumeric characters, including numbers.

While a pumping system that creates fluid pressure could be used for dispensing a fluidic drug into a body through hollow microneedles, such as emplaced on pads 600, in many instances it is preferred to use an electrophoresis method to enhance the delivery of the drugs through the microneedles. As discussed hereinabove, application of microneedles can decrease the electrical resistance of the stratum corneum by a factor of fifty (50), and so the voltage necessary to facilitate electrophoresis can be greatly reduced, improving safety and requiring much less power consumption. By use of the electrophoresis, the molecules making up the fluid drug will travel through the thicker dermis into or from the body, and the combination of both transport-enhancing methods provides an increase in permeability for both the stratum corneum and the deeper layers of the skin. The transport improvement in the stratum corneum is mostly due to microneedle piercing, although the electrophoresis provides higher transport rates in the epidermis and dermis.

The closed-loop drug-delivery system and fluid-sampling system 700 can be used for continuous noninvasive measurement of blood glucose level by extracting, via reverse iontophoresis, glucose through the skin and measuring its concentration by the bioelectrochemical sensor (such as the sensor constructed of the hydrogel chamber 510 and sensor electrode 525, along with the controller 720). The hydrogel pads containing microneedles (i.e., pads 500) enhance the reverse iontophoresis to move glucose molecules from the body by the flow of sodium and chloride ions, which are caused by the applied electric potential via electrodes 520 and 522. Once the glucose concentration is measured within the hydrogel pads 500, the proper amount of insulin, for example, can be dispensed through the other pair of pads 600 that make up part of the closed-loop system 700.

As discussed hereinabove, drug delivery is performed by applying an electric potential between two microneedle array electrodes. One of the electrodes is filled with an ionized drug (such as insulin), and the charged drug molecules move into the body due to the electric potential. Controller 720 will determine how much of a drug is to be dispensed through the microneedle array 600 at any particular time, thereby making the closed-loop system 700 a "smart" drug-delivery system.

This smart drug-delivery system can be used as an artificial pancreas for diabetes patients, as a portable hormone-therapy device, as a portable system for continuous outpatient chemotherapy, as a site-specific analgesic patch, as a temporary and/or rate-controlled nicotine patch, or for many other types of drugs. Such systems could be made as a disposable design, or as a refillable design.

It will be understood that the closed-loop system 700 can be used in many applications, including as a painless and convenient transdermal drug-delivery system for continuous and controlled outpatient therapies, a painless and convenient body-fluid sampling system for continuous and programmed outpatient body-fluid monitoring, as a high-rate transdermal drug delivery system, or as a high-accuracy transdermal body-fluid sampling system. More specifically, the closed-loop system 700 of the present invention can be used as a portable high-accuracy painless sensor for outpatient blood glucose-level monitoring, as a portable system for continuous or rate controlled outpatient chemotherapy, as a temporary and rate controlled nicotine patch, as a site-specific controlled analgesic patch, as an externally attached artificial pancreas, as externally attached artificial endocrine glands, as temperature-controlled fever-reducing patches, as heart rate-controlled nitroglycerin high-rate transdermal patches, as temporarily controlled hormonal high-rate transdermal patches, as erectile dysfunction treatment high-rate transdermal patches, and as a continuous accurate blood-analysis system. Another use of the closed-loop system 700 of the present invention is to form a portable drug delivery system for outpatient delivery of the following drugs and therapeutic agents, for example: central nervous system therapy agents, psychic energizing drugs, tranquilizers, anticonvulsants, muscle relaxants and antiparkinson agents, smoking cessation agents, analgetics, antipyretics and anti-inflammatory agents, antispasmodics and antiulcer agents, antimicrobials, antimalarias, sympathomimetric patches, antiparasitic agents, neoplastic agents, nutritional agents, and vitamins.

It will be understood that various materials other than those disclosed hereinabove can be used for constructing the closed-loop system 700, and for constructing individual body-fluid sampling sensors and individual drug-delivery systems. Such other materials could include diamond, biocompatible metals, ceramics, polymers, and polymer composites, including PYREX®. It will yet be further understood that the electrophoretically/microneedle-enhanced transdermal method of transport of the present invention can also be combined with ultrasound and electroporation, in order to achieve high-rate drug delivery into individual cells.

It will also be understood that the length of the individual microneedles is by far the most important dimension with regard to providing a painless and bloodless drug-dispensing system, or a painless and bloodless body-fluids sampling system using the opposite direction of fluid flow. While the dimensions discussed hereinabove are preferred, and the ranges discussed are normal for human skin, it will further be understood that the microneedle arrays of the present invention can be used on skin of any other form of living (or even dead) creatures or organisms, and the preferred dimensions may be quite different as compared to those same dimensions for use with human skin, all without departing from the principles of the present invention.

It yet will be understood that the chemicals and materials used in the molds and dies can be quite different than those discussed hereinabove, without departing from the principles of the present invention. Further, it will be understood that the chemicals used in etching and layering operations of microfabrication discussed above could be quite different than those discussed hereinabove, without departing from the principles of the present invention.

Figure 32:
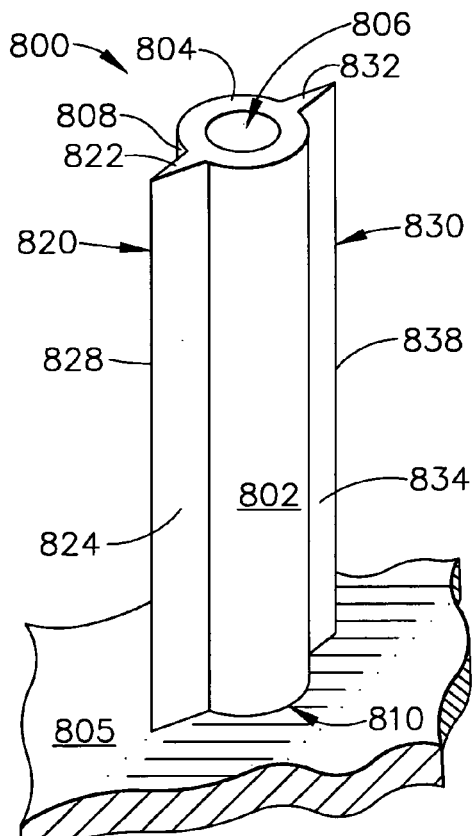
FIG. 32 is a perspective view of an alternative embodiment hollow microneedle having sharp edges for greater penetration into skin.

FIG. 32 illustrates another alternative embodiment of a hollow microneedle, generally designated by the reference numeral 800. The main body of the microneedle 800 has a generally cylindrical shape, as indicated by its outer surface at 802. A generally circular opening creates a hole at 806 through which fluids can pass. The cylindrical shape is preferably maintained throughout the length of microneedle 800, so that its bottom profile would also maintain a generally circular shape, as depicted at 810. Of course, minor variances in this shape could be utilized without departing from the principles of the present invention, such as an elliptical shape for its cross-section (rather than a circular shape), for example.

The general cylindrical shape is preferably maintained also at the top portion, as seen by the outer wall at 808. The top surface at 804 will have the form of a pair of concentric circles, in situations where the opening 806 is circular. The bottom portion at 810 of microneedle 800 is abutted to a base element having a generally planar surface at 805. In a preferred mode of construction, microneedle 800 and the surface 805 would be of a unitary construction, i.e., it would be formed from a single piece of material. This single piece of material would preferably be a molded plastic or like material, or a cast metal or like material. Of course, composite materials could also be utilized.

One primary advantage of the shape of microneedle 800 is that it has a pair of sharp edged projections at 820 and 830 that aid the penetration of the outer surface (i.e., stratum corneum) of the skin, thereby requiring less force to be applied when using an array of such microneedles 800. Each edged projection or blade 820, 830 has a cross-sectional shape that is generally triangular when viewed from the top of microneedle 800 (see FIG. 33). The exact shape of the triangle will depend upon the strength requirements of each of the blades 820, 830, the material used to construct microneedle 800, and the amount of skin damage that is allowable in a particular usage application. The preferred cross-sectional shape is that of an isosceles triangle having a base angle in the range between 1 and 45°. Of course, a rounded contour could be used instead of straight walls for the blade surfaces, without departing from the principles of the present invention.

The illustrated blade 820 has an upper generally triangular surface at 822, and one of its side walls is represented by the planar surface at 824, as seen on FIG. 32. A similar planar wall is on the opposite side at 836 (see FIG. 33), and the junction of these two planar walls 824, 826 forms a generally sharp edge, as depicted at the reference numeral 828.

The second protrusion or blade 830 is similarly formed of two generally planar side walls at 834 and 836 (see FIG. 33), which also join at a generally sharp edge at 838. The upper surface of the blade 830 is depicted at 832 as having a generally triangular shape, in the illustrated embodiment.

It will be understood that either less or more than two sharpened blade projections could be utilized in the microneedle 800 of FIG. 32 without departing from the principles of the present invention, although the two blades 820 and 830 are an optimal design.

Figure 33:
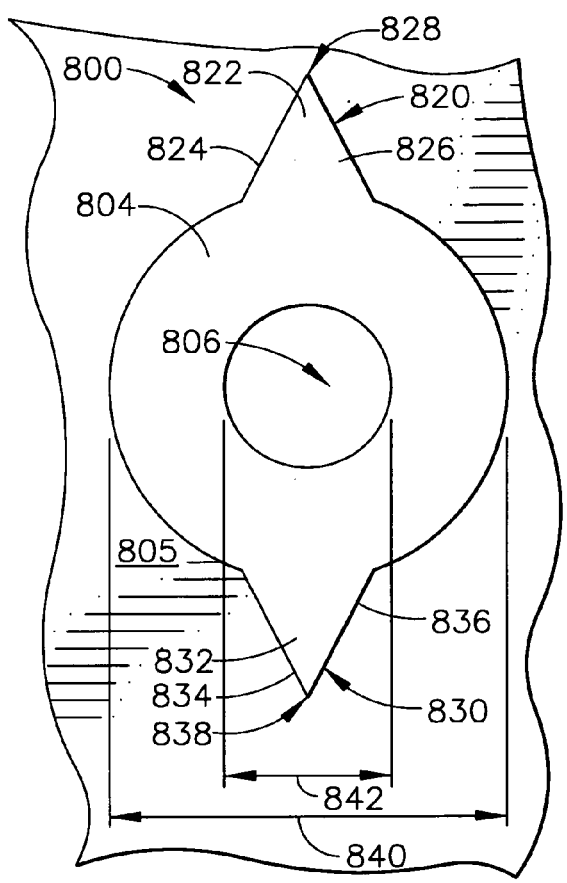
FIG. 33 is a top plan view of the edged hollow microneedle of FIG. 32.

As illustrated on FIG. 33, the inner diameter of the opening 806 is depicted at the reference numeral 842, and the outer diameter of the microneedle 800 is depicted at the reference numeral 840. The size of the outer diameter of microneedle 800 is very important as to its penetrating capabilities into the skin, whereas the inner diameter 842 is of lesser importance in that regard. However, the inner diameter 842 must be large enough to easily pass the desired molecules of the fluid to be passed therethrough.

Figure 34:
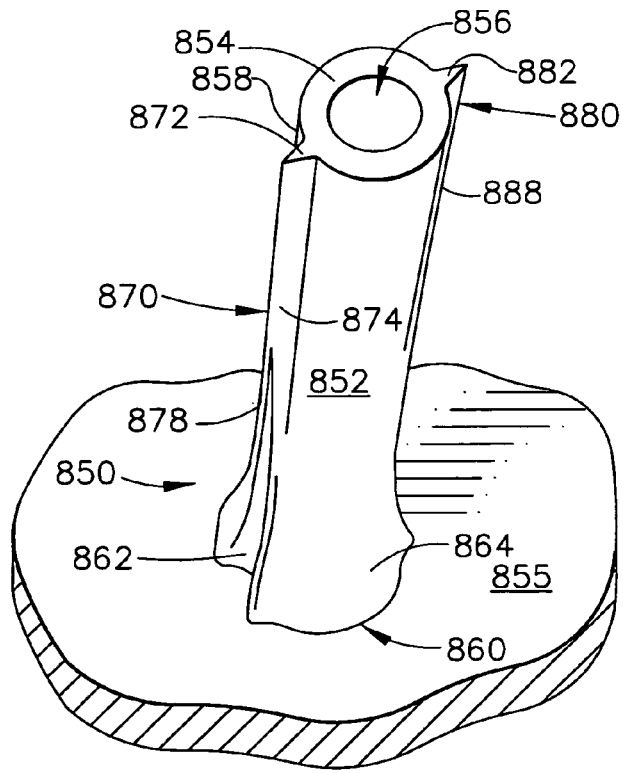
FIG. 34 is a perspective view of an alternative construction for an edged hollow microneedle as seen in FIG. 32.

FIG. 34 illustrates a similar hollow microneedle, generally designated by the reference numeral 850. This alternative embodiment microneedle 850 also includes two longitudinal blade structures at 870 and 880, and also is of a generally cylindrical shape throughout most of its length from its base element's bottom surface at 855 to its top surface at 854. The opening at 856 is also generally circular in situations where the microneedle 850 is of cylindrical shape. Of course, the overall outer shape of the microneedle 850 and the inner shape of the opening 856 could be somewhat non-circular (such as an ellipse) without departing from the principles of the present invention.

In FIG. 34, microneedle 850 could be constructed of a molded plastic or a cast metal material, but in this particular representation the microneedle 850 is constructed using semiconductor fabrication techniques. The first blade 870 has a generally planar side wall at 874, and in conjunction with a similar side wall not shown on FIG. 34, forms a generally sharp edge at 878. The cross-section profile of this blade structure 870 is seen at 872, as having a generally isosceles triangular shape, although more rounded side walls could be utilized without departing from the principles of the present invention. On FIG. 34, this sharp edge 878 does not continue all the way to the bottom surface 855 of the microneedle base structure, but instead continues down to a point where the blade structure discontinues, as illustrated at 862. This could be utilized to create a greater yield of microneedle structures using semiconductor fabrication techniques, or could be utilized to create a structure having greater mechanical strength near the bottom areas (e.g., at the side wall area 864) of the microneedle 850. When using this type of shape for the structure of microneedle 850, the outer diameter of the microneedle has the form shown at 860 as it joins the planar bottom surface 855. This shape at 860 could be generally semi-circular, but also could be of a larger diameter to provide greater mechanical strength than the outer diameter near the top surface 854 of microneedle 850.

The second blade 880 has a similar top profile at 882, and a similar sharp edge at 888. The side wall structure near the bottom of the second blade 880 is not viewable in FIG. 34, but can be inferred from the shape of the bottom sidewall at 864.

Other variations in shape of the microneedle structures depicted in FIGS. 32 and 34 could be utilized without departing from the principles of the present invention. The primary goals are to create mechanically sound structures that can penetrate the stratum corneum of human skin (or other type of animal or even plant skin), and the sharp longitudinal blade structures are a great improvement over such hollow microneedles that do not have these side blades, enhancing penetration of drugs through the skin. It will be understood that the microneedle structures depicted in FIGS. 32 and 34 could be constructed of any materials and by any type of fabrication techniques, without departing from the principles of the present invention.

Figure 57A:
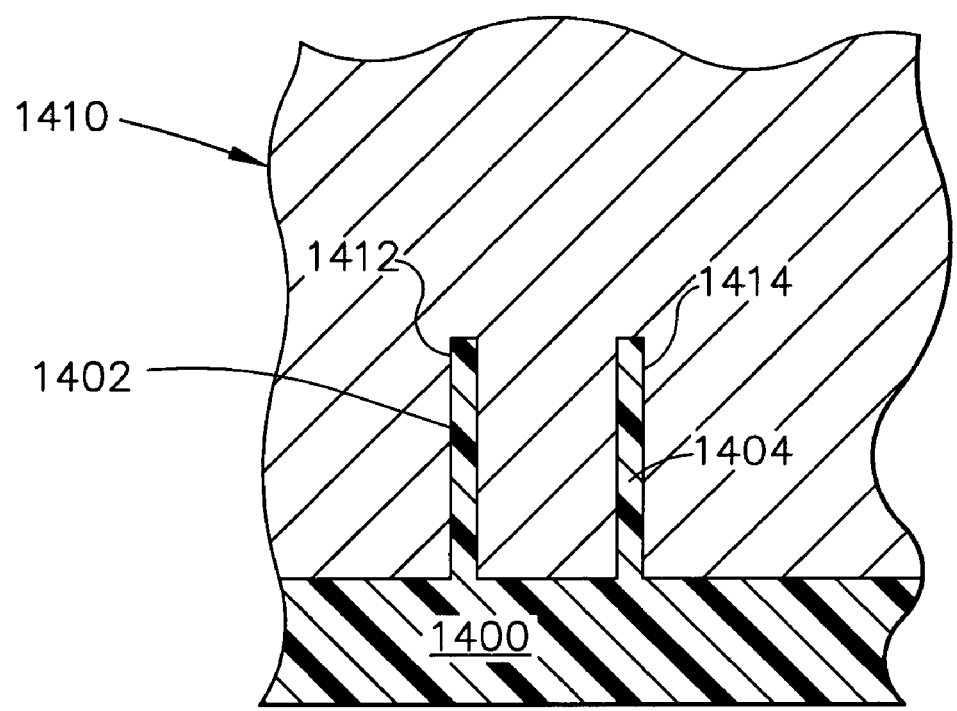
FIGS. 57A–57B are side elevational views of a de-molding procedure to create sharp hollow microneedles.
Figure 57B:
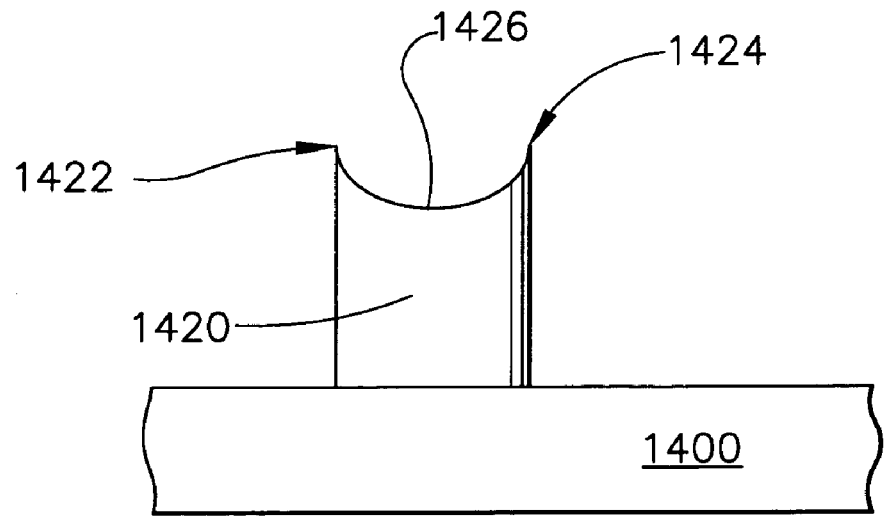

Another variation in the hollow microneedles depicted on FIGS. 32 and 34 would be to have a top surface that is not generally flat, but instead has a arcuate or parabolic top surface as seen from one of the sides of the microneedle structure. This type of structure could either be machined, or could be generated during de-molding, as illustrated in FIGS. 57A and 57B, discussed hereinbelow.

Figure 35:
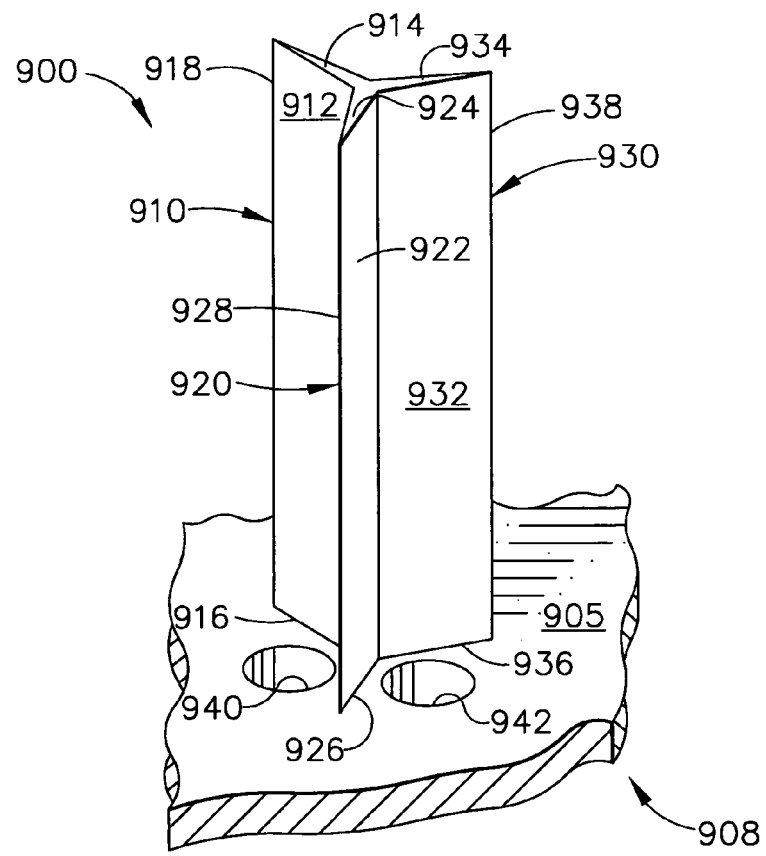
FIG. 35 is a perspective view of an alternative embodiment solid microneedle having a star-shaped set of sharp blades.
Figure 36:
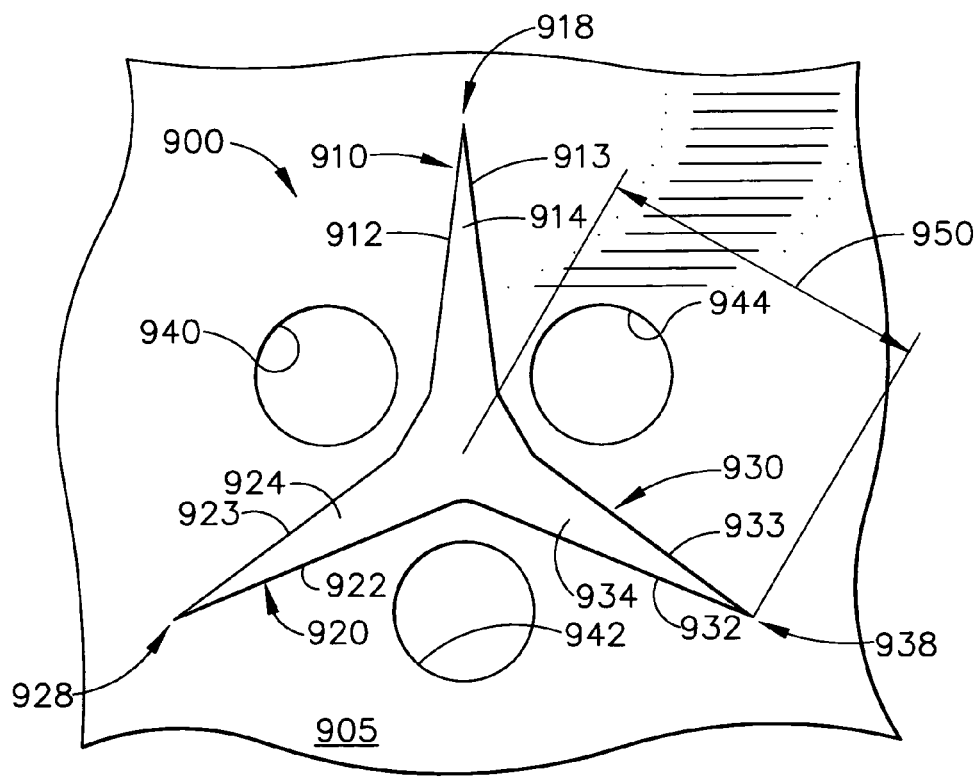
FIG. 36 is a top plan view of the star-shaped solid microneedle of FIG. 35.

An alternative solid microneedle shape is depicted in FIGS. 35 and 36, in which the solid microneedle is generally star-shaped in profile. As viewed from its top surface (see FIG. 36), the solid microneedle 900 is a generally three-pointed star shape, having three longitudinal blades at 910, 920, and 930. The top surface of each of these star-shaped blades is depicted at 914, 924, and 934, and as can be seen from FIGS. 35 and 36, a major portion of these top surfaces is generally triangular in shape. The preferred shape is that of an isosceles triangle, in which the base angle of this triangle is in the range of 1–45°. Of course, the smaller this base angle, the smaller the amount of skin damage done when the microneedle 900 is inserted into the stratum corneum.

Each blade 910, 920, and 930 has a pair of generally planar side walls at 912, 913, 922, 923, 932, and 933 (although these side walls could be somewhat curved in contour, if desired). These side walls converge to form a generally sharp point at 918, 928, and 938, respectively. In the illustrated embodiment of FIG. 35, microneedle 900 continues this star-shaped profile from its top surfaces at 914, 924, and 934 down to its bottom edges at 916, 926, and 936, where the microneedle structure joins its top planar base structure at 905. Of course, the very upper surfaces are most key as far as making a penetration into the skin through the stratum corneum, and the precise shape of the blades 910, 920, and 930 may somewhat vary along the longitudinal length of microneedle 900 without departing from the principles of the present invention. The major benefit of this shape is its small cross-sectional area allowing easy insertion into the skin, yet a large surface area providing high rates of active penetration through the skin.

Since microneedle 900 is solid, for liquid to be dispensed into the skin or to be sampled from the skin, a set of openings is provided in the base element or substrate at 908. It is preferred that a single opening be located along each pair of projections or blades, as illustrated on FIG. 36, in which an opening 940, 942, and 944 is provided between the blades 910–920, 920–930, and 930–910, respectively. Of course, different sized holes and different hole locations, as well as different numbers of holes for that matter, could be utilized with the solid microneedle 900, without departing from the principles of the present invention.

Microneedle 900 could be constructed of virtually any material that is biocompatible with human skin (or other animal or plant skin). This includes molded plastic or cast metal, or perhaps a silicon or silicon-dioxide structure that is manufactured using semiconductor and plastic fabrication techniques. The top surface at 914, 924, and 934 is illustrated as being generally planar, although this could be changed easily enough to cause the mid-portions of the microneedle 900 to be somewhat lower than the points of the three blades at their top edges 918, 928, and 938. Such a construction would have a similar side appearance to the hollow microneedle 1420 depicted on FIG. 57B.

It will be understood that more or less than three blades could be constructed to create a solid microneedle such as that of microneedle 900, without departing from the principles of the present invention. Even a single blade design could be used, having either one or two sharp edges. While the three-bladed solid microneedle 900 is of an optimal design, certainly a four-bladed design could also be manufactured and used, and provide generally good results. In a four-bladed design, it would be preferred that each pair of blades have a corresponding through-hole in the substrate beneath the bottom portion of the solid microneedle, although such holes are not necessarily required between each pair of blades. The size of each of the through-holes such as holes 940, 942, and 944 is up to the designer, although its inner diameter should be sufficiently large to allow useful molecules to pass therethrough.

Another very important attribute of arrays of microneedles is the separation distance between each of the microneedles with regard to their placement on the substrate or base structure. On one hand, the more microneedles per given area of a substrate, the greater the amount of "transdermal flux" (or transdermal flow) of a fluid that will be transported through the microneedles (i.e., in the case of hollow microneedles). On the other hand, it has been determined that the closer the spacing of microneedles, the less likely that the microneedles will actually penetrate the stratum corneum layer of skin due to the elasticity characteristics and mechanical strength of skin. Therefore, a dichotomy exists that indicates the separation between microneedles is critical for a useful device.

FIGS. 37–42 provide tabular data illustrating the effects of microneedle length, microneedle outer diameter, and microneedle separation for circular hollow microneedles, such as those depicted in FIG. 15, FIG. 22, and FIGS. 25 and 28. As related hereinabove, the microneedles illustrated in these figures are hollow, having internal cylindrical openings, but are not edged or sharpened with respect to having any type of blade structure along their outer surfaces or tips. Furthermore, the tabular data of FIGS. 37–42 are with respect to microneedles that are arranged in a hexagonal configuration. All dimensions on these FIGS. 37–42 are in microns (i.e., micrometers). Each chart shows ten rows that represent various microneedle lengths in the range of 30–300 microns, and ten columns showing microneedle outer diameters in the range of 10–100 microns. Each chart is for a different separation distance, starting with 50 microns, and then incrementing by 50 microns to the final chart of FIG. 42 that shows a separation of 300 microns.

The table entries of "Y" represent a situation where the microneedle penetrates the skin. A table entry of "n" represents a configuration where the microneedle will not penetrate skin. Finally, the "diamond" shape represents a table entry in which the microneedle will possibly penetrate the skin, however, it is not certain that penetration will occur.

Each table contains a dashed line (such as line 1002 on FIG. 37) that roughly indicates that table entries below the line will likely penetrate the skin, whereas table entries above the line will likely not penetrate the skin. These lines represent approximations to a certain extent, and a tolerance of at least plus or minus 10% should be considered when utilizing this data. In some circumstances, the tolerance should be more like plus or minus 20%.

On the various charts, the lines are indicated at 1002 for FIG. 37, 1004 for FIG. 38, 1006 for FIG. 39, 1008 for FIG. 40, 1010 for FIG. 41, and 1012 for FIG. 42. Each of these lines can be approximately defined by an equation, in which the variables are microneedle length represented by "L," and the outer diameter represented by the variable "D." For these equations, all dimensions are in microns. In FIG. 37, the equation is: $L=+120$; for FIG. 38, the equation is: $L=5D+50$; for FIG. 39, the equation is: $L=2.77D+72.3$; for FIG. 40, the equation is: $L=1.54D+59.2$; for FIG. 41, the equation is: $L=0.856D+124$; and for FIG. 42, the equation is: $L=0.47D+133$.

FIGS. 43–48 provide further tabular data, this time for edged or "sharp" hollow microneedles, such as those depicted in FIGS. 32–34. These edged microneedles are also circular or cylindrical in overall shape, but, as described above, include two longitudinal blades with a relatively sharp edge to aid in penetrating the stratum corneum of the skin. As will be seen as compared to the tables of FIGS. 37–42, penetrating skin is more easily accomplished using the edged microneedles. As noted hereinabove, an "edged" microneedle is one in which its tip has a radius less than or equal to 0.5 microns.

As before, a table entry of "Y" indicates that a penetration occurs, a table entry of "n" indicates that a penetration does not occur, and a table entry of a diamond-shaped symbol indicates that a penetration of the skin may occur, but is not definite. A dashed line is drawn on FIGS. 43–48 to indicate the likelihood that entries above the dashed line will not succeed in penetrating the skin, while entries below the line will be successful in such penetration. The lines are indicated by the reference numerals 1022 for FIG. 43, 1024 for FIG. 44, 1026 for FIG. 45, 1028 for FIG. 46, 1030 for FIG. 47, and 1032 for FIG. 48.

Similar equations for these lines can be determined from this data, where again the variable L is equal to the microneedle length and the variable D is equal to the outer diameter of the microneedle. In FIG. 43, the approximate equation is: $L=9D+30$; in FIG. 44, the equation is: $L=5D$; in FIG. 45, the equation is: $L=2.77D+11.5$; in FIG. 46, the equation is: $L=1.54D+56$; in FIG. 47, the equation is: $L=0.856D+64.4$; and in FIG. 48, the equation is: $L=0.47D+96.5$.

It can be easily seen from the tabulated data of FIGS. 37–48 that the greater the separation between microneedles, the more likely that the skin will be penetrated at any given length of microneedle. If relatively small microneedles having an outer diameter of twenty microns are desired for use in a microneedle array, then the tabular data indicates that the microneedle should be at least 100 microns in length, and either 250 or 300 microns separation distance (see FIGS. 41 and 42). On the other hand, the same 20 micron outer diameter microneedles that include edges (as per FIG. 32) will likely penetrate the skin at a needle length of at least 60 microns and a separation of 150 or 200 microns. This is an obvious improvement in microneedle density per unit area of the substrate upon which the microneedle array is mounted, thereby allowing a dramatic increase in the amount of material delivered or extracted through the skin.

Microneedle density is an important factor in dispensing fluids or sampling fluids through the stratum corneum of the skin. This is clearly indicated in the graph of FIG. 49, in which the X-axis represents microneedle separation in microns, and the Y-axis represents the transdermal flux of an active fluid such as a niacinamide solution, in units of micrograms per square centimeter per 24 hours of time.

Figure 49:
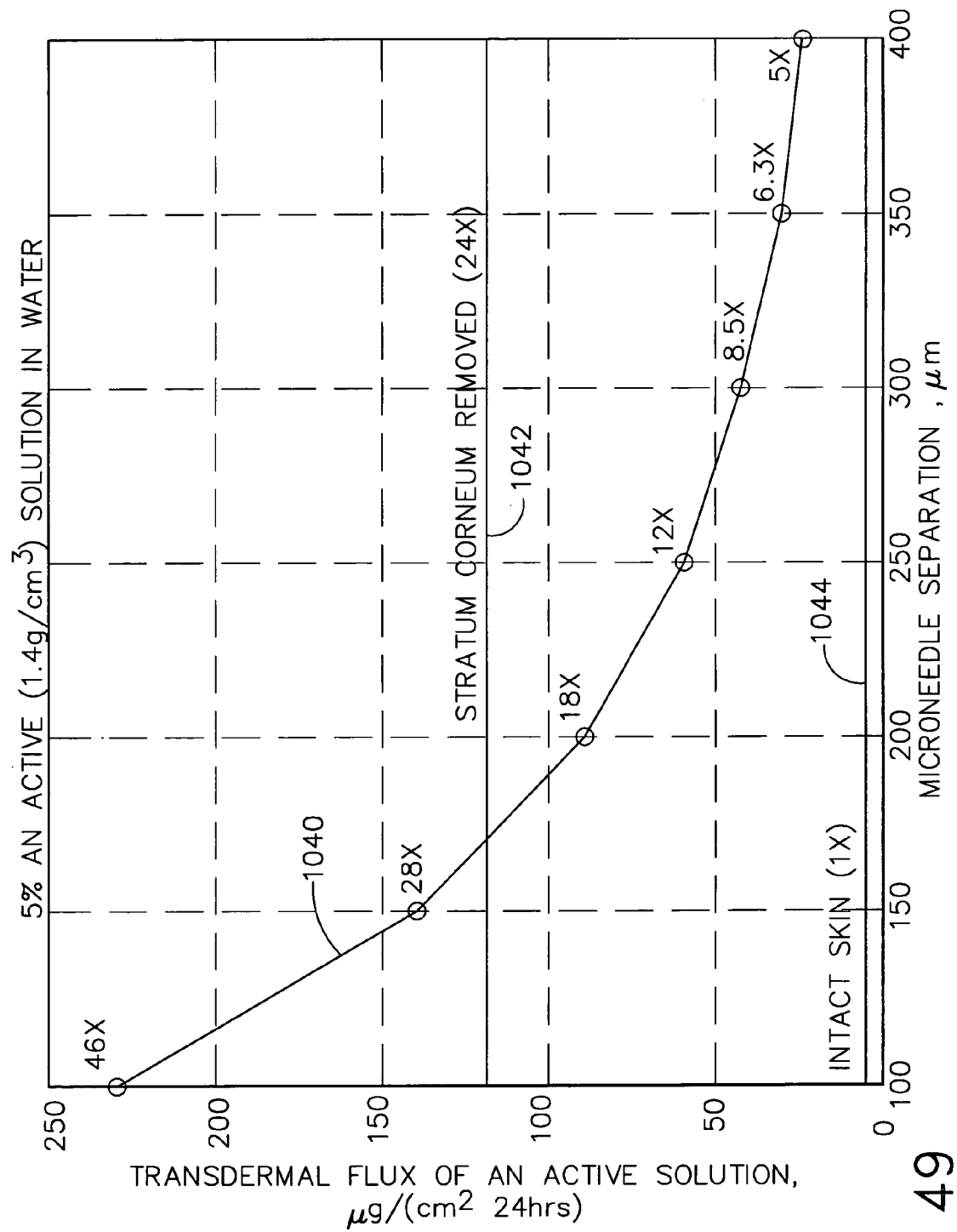
FIG. 49 is a graph showing the effect of microneedle separation versus transdermal flux.

The base or reference line of FIG. 49 is represented by the "intact skin" line 1044, which is in essence the transdermal flux rate of normal skin without any microneedles, in the above units of five (5) micrograms per square centimeter per 24 hours time. This base line 1044 is also indicated as being "1×" times a nominal transdermal flux rate. If the stratum corneum layer of human skin is removed, then the transdermal flux rate is increased by a factor of twenty-four (24), and is represented by the line 1042, which indicates approximately one hundred twenty (120) micrograms per square centimeter per 24 hours of transdermal flux flow rate. This line is also referred to as "24×" on FIG. 49.

If microneedles are used, the flow rate is variable, as per the curve (or more accurately, the segmented line) at 1040, which at 100 microns of separation provides a 46 times (or 46×) flow rate as compared to the intact skin flow rate of 1×. This flow rate naturally decreases as the microneedle separation increases, since the density of microneedles is proportionate to the square root of separation distance. For example, at a microneedle separation of 400 microns, the transdermal flux rate is only 5 times (5×) the flow rate of intact skin (at 1×).

FIG. 49 assumes that the microneedle lengths are sufficiently long and have a sufficient shape to penetrate the skin at the separations listed along the X-axis. Otherwise, the transdermal flux rates will be significantly reduced. However, any microneedle usage that does not actually penetrate the stratum corneum will likely create a certain amount of indents and breaks in the skin, which will provide a certain increase in the transdermal flux rate. For example, if the microneedle array is provided having microneedles of 40 microns in outer diameter and 50 microns in length, it is not likely that microneedle penetration will occur in very many places at virtually any separation. However, there will still be enough indents and breaks in the skin to provide a four times (i.e., 4×) increase in the transdermal flux of a drug or solution such as niacinamide in water. To achieve the results of FIG. 49, the microneedle length was 100 microns and its outer diameter was 20 microns. It can be seen from FIG. 49 that a microneedle separation of around 170–175 microns will provide results that are equal to the removal of the stratum corneum layer of skin.

Figure 50:
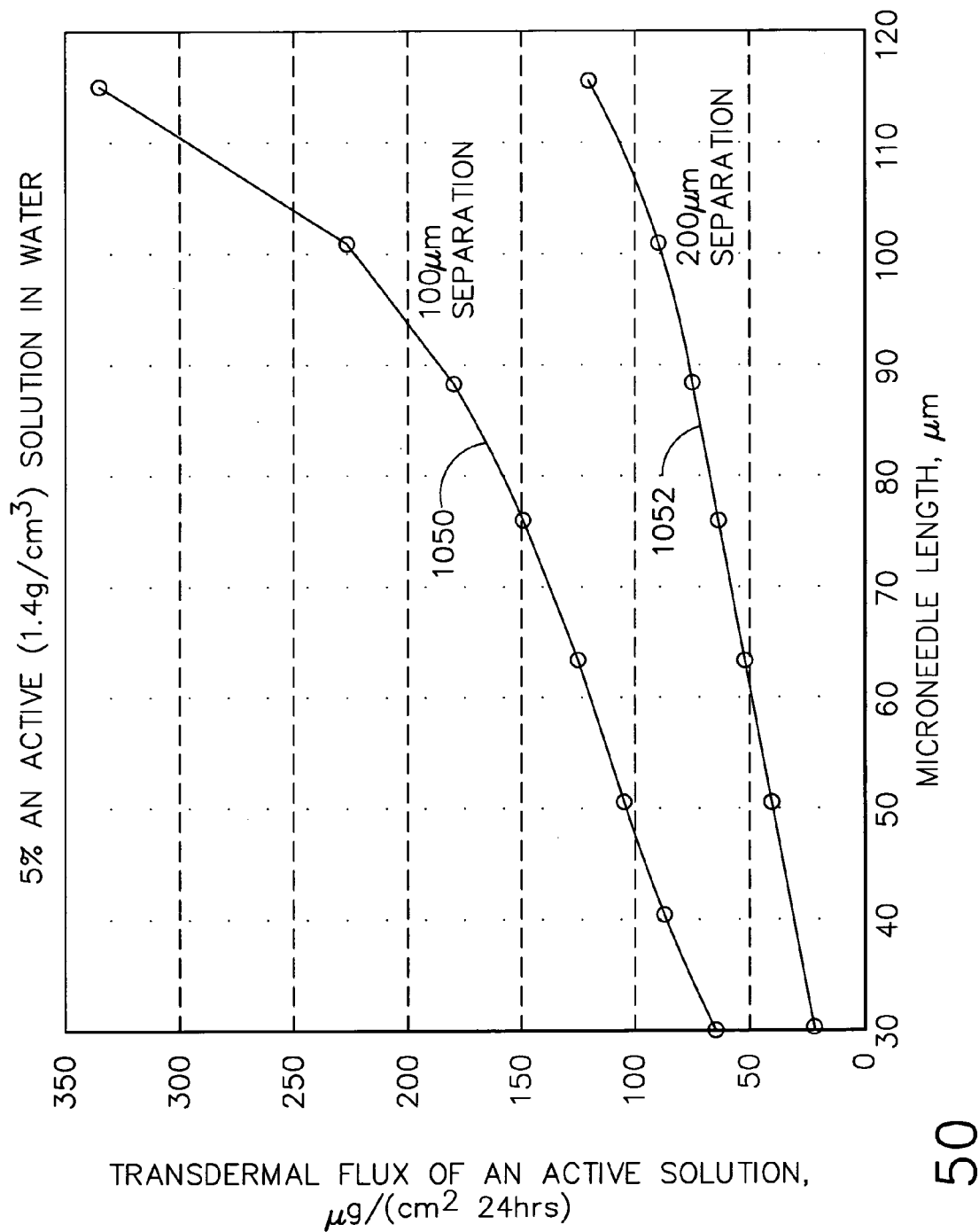
FIG. 50 is a graph showing the effect of microneedle length versus transdermal flux for two different microneedle separation distances.

Utilizing a passive diffusion model of human skin and microneedle structures, the inventors also provide the chart of FIG. 50. The X-axis of FIG. 50 represents the microneedle length in microns, while the Y-axis represents the transdermal flux of an active solution, in micrograms per square centimeter per 24 hours time period. The curves on the graph are depicted with respect to a 5% niacinamide solution in water.

The lower curve at 1052 represents a microneedle array in which the needles have a 200 micron separation in a hexagonal pattern. The upper curve at 1050 represents a microneedle array in which the microneedles have a 100 micron separation in a hexagonal pattern. Very useful transdermal flux rates can be provided with microneedle arrays having a separation of 200 microns at a needle length of 100–110 microns, and an outer diameter of 20 microns. It can be seen from FIG. 46 that this range of microneedle lengths and outer diameters lies within a small tolerance of the line 1028 that indicates whether or not microneedle penetration will occur in skin. This table of data on FIG. 46 represents edged hollow microneedles, as described above.

Figure 51:
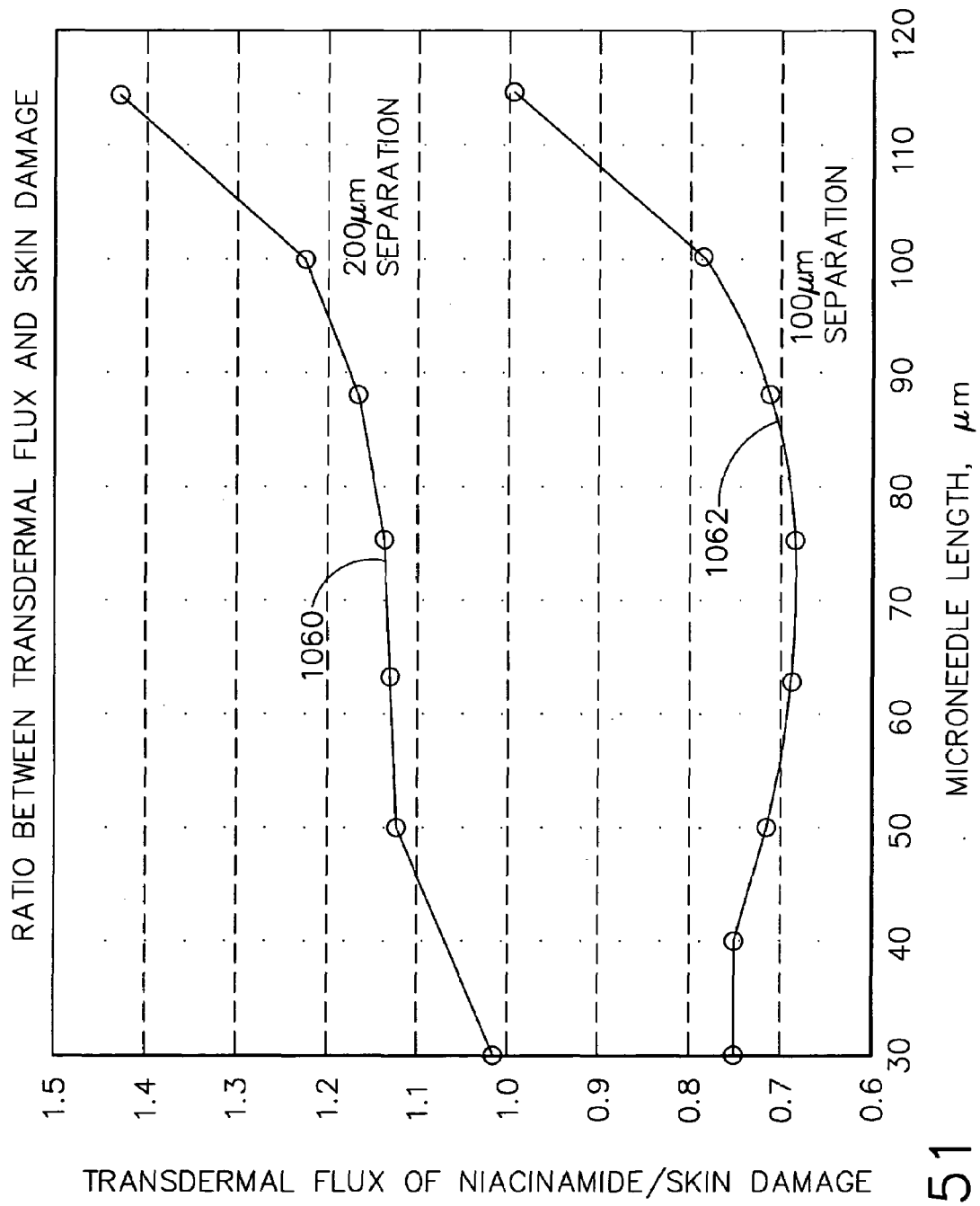
FIG. 51 is a graph showing the effect of microneedle length versus a ratio of transdermal flux versus skin damage, for two different microneedle separation distances.

FIG. 51 provides another measure of usage for microneedles. The X-axis represents microneedle length in microns, while the Y-axis is a ratio of transdermal flux using a solution of niacinamide in water versus skin damage when using the microneedle array. A nominal figure of transdermal flux versus skin damage is provided at the value of one (1) along the Y-axis. The upper curve at 1060 depicts the ratio when microneedles have a 200 micron separation. The lower curve 1062 shows a similar microneedle array having only a 100 micron separation. While the transdermal flux will typically be much greater when the microneedle separation is smaller, also the skin damage will be greater. As can be seen from the curves 1060 and 1062, once the microneedle length exceeds 100 microns, the transdermal flux versus skin damage ratio tends to increase rather sharply. The microneedle outer diameter was 20 microns for the data of FIG. 51.

Figure 52:
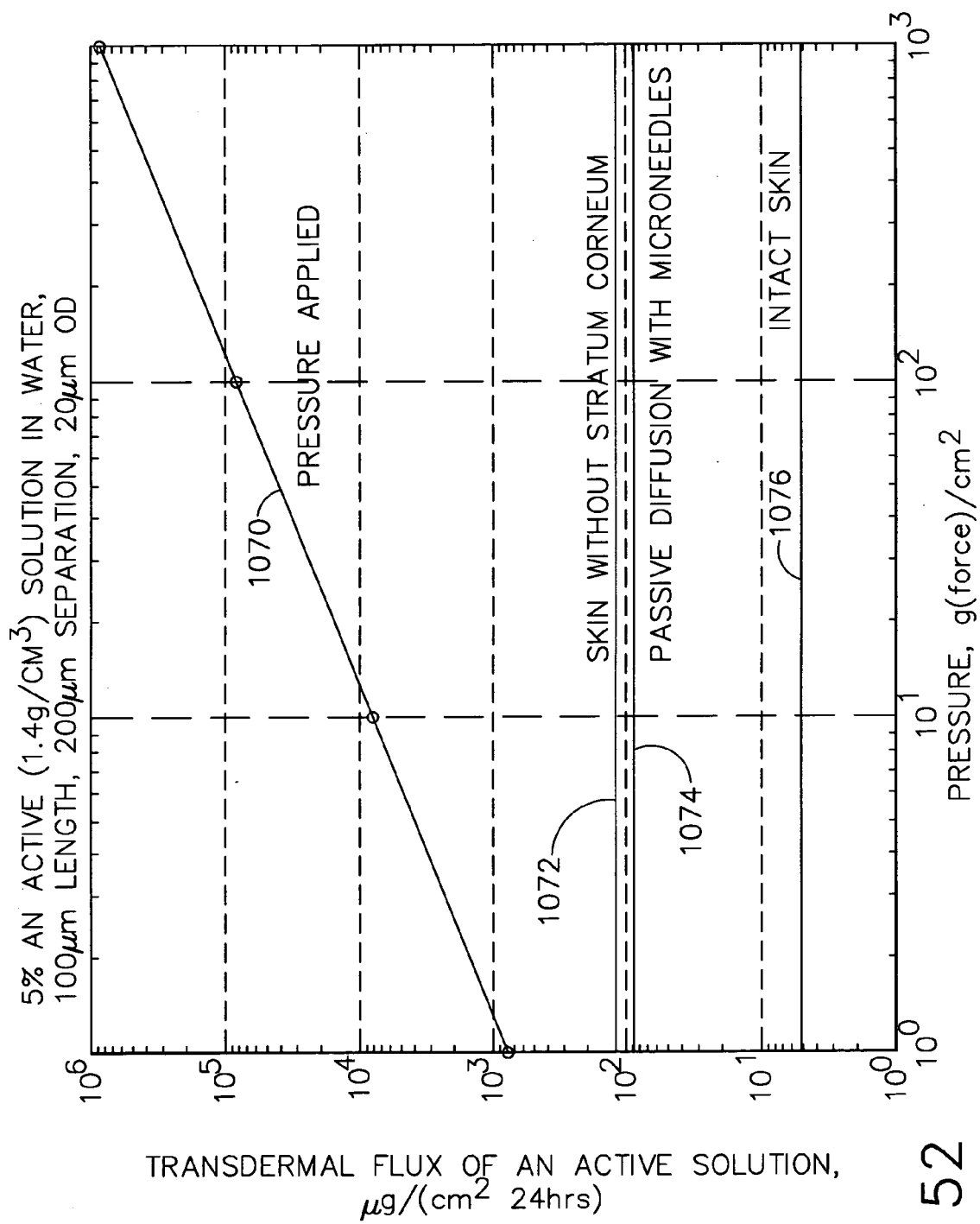
FIG. 52 is a graph showing the effect of applied pressure of a fluid versus transdermal flux for a particular microneedle array.

FIG. 52 is another graph representing information regarding passive diffusion of fluids using microneedles as compared to the use of microneedles under pressure to increase the transdermal flow. The X-axis is in units of pressure, g's per square centimeter. The Y-axis is the transdermal flux of an active solution in micrograms per square centimeter per 24 hours time period, and the values of this chart are for a 5% solution of niacinamide. In addition, the results of this chart were produced using microneedles of 100 microns length, 20 microns outer diameter, and a separation of 200 microns.

For intact skin, the lowest horizontal line at 1076 indicates a relatively low transdermal flux of the solution to the skin. If the stratum corneum of the skin is removed, this transdermal flux greatly increases to the higher horizontal line at 1072. Another horizontal line at 1074 indicates the transdermal flux rate using microneedles under passive diffusion.

If pressure is applied, then the flow rate changes as the pressure changes. This is indicated by the sloped line 1070. As can be seen, if the pressure is increased by three orders of magnitude, then the flow rate of the transdermal flux also increases by approximately three orders of magnitude.

Based upon the above information, it is preferred that the outer diameter of circular microneedles (without "sharp" edges) be in the range of 20–100 microns, more preferably about 20–50 microns. In addition, it is preferred that the height (or length) of the microneedles for use with interstitial fluids be in the range of 50–200 microns, more preferably about 100–150 microns; for use with other biological fluids, the preferred length is in the range of 200 microns–3 mm, and more preferably in the range of 200–400 microns. Finally, it is preferred that the separation between microneedles in the array be in the range of 100–300 microns, more preferably about 100–200 microns. Of course, dimensions outside the above-listed ranges will still be somewhat useful, even for microneedle lengths and separation distances as small as 50 microns, or as large as 1000 microns.

For hollow circular microneedles having edges (e.g., see microneedle 800 in FIG. 32), it is preferred that the outer diameter be in the range of 20–100 microns, and more preferably in the range of 20–50 microns. For use with interstitial fluids the length will preferably be in the range of 50–200 microns, more preferably in the range of 80–150 microns; for use with other biological fluids, the length will preferably be in the range of 200 microns–3 mm, and more preferably in the range of 200–400 microns. Finally, the separation will preferably be in the range of 100–300 microns, more preferably in the range of 100–200 microns.

For solid microneedles of the star-shaped design depicted on FIGS. 35 and 36, it is preferred that the radius of one of the spokes or edged blades (e.g., blade 910), as indicated by the radius 950 on FIG. 36, be preferably in the range of 10–50 microns, and more preferably in the range of 10–15 microns. The length of the solid microneedles will preferably fall in the range of 50–200 microns for use with interstitial fluids, and more preferably in the range of 80–150 microns; for use with other biological fluids, the length will preferably be in the range of 200 microns–3 mm, and more preferably in the range of 200–400 microns. The separation distance will preferably fall in the range of 100–300 microns, and more preferably in the range of 100–200 microns.

Figure 53A:
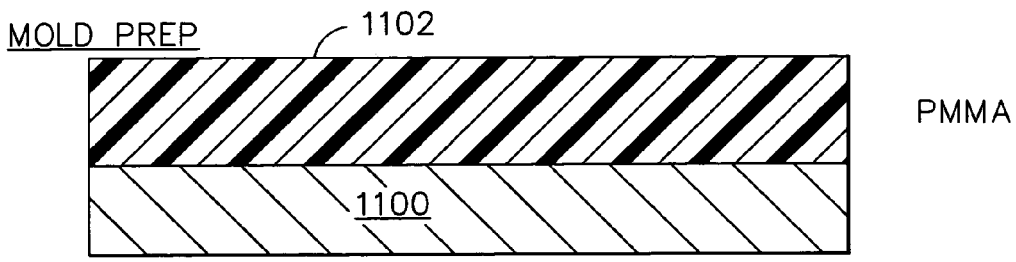
FIGS. 53A–53E are elevational views in cross-section illustrating steps for preparing a mold for a micromolding procedure to create hollow circular microneedles.

FIGS. 53A–53E illustrate the steps for preparing a mold to make hollow microneedles, according to the principles of the present invention. The first step is depicted in FIG. 53A, in which a substrate 1100 is provided with a top layer of positive photoresist material at 1102. The substrate can be spin coated, or an adhesive can be used to attach the photoresist 1102 to the substrate 1100. The substrate can consist of silicon, silicon-dioxide, plastic, metal, or other suitable compounds. The photoresist material will preferably comprise poly(methylmethacrylate), also known as "PMMA," although other suitable compounds could be used, such as polyoxymethylene (POM), polyalkensulfone (PAS), polymethacrylimide (PMI), and poly(lactide-co-glycolide) (PLG).

Figure 53B:
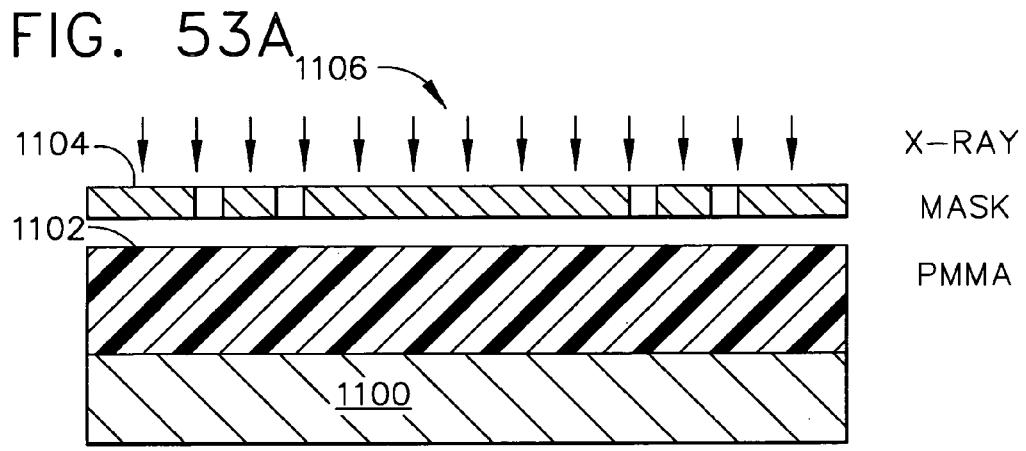

In FIG. 53B, a mask at 1104 is placed over the photoresist layer 1102, and electromagnetic energy is directed through the mask from a light source, in which the light energy moves in the direction as indicated at 1106 on FIG. 53B. The mask 1004 preferably is made of gold metal, and in this instance, the electromagnetic energy comprises x-rays. It will be understood that many different types of photoresist procedures or the like could be used without departing from the principles of the present invention, and for example, high energy nuclear particles might be substituted for electromagnetic energy in some processes.

Figure 53C:
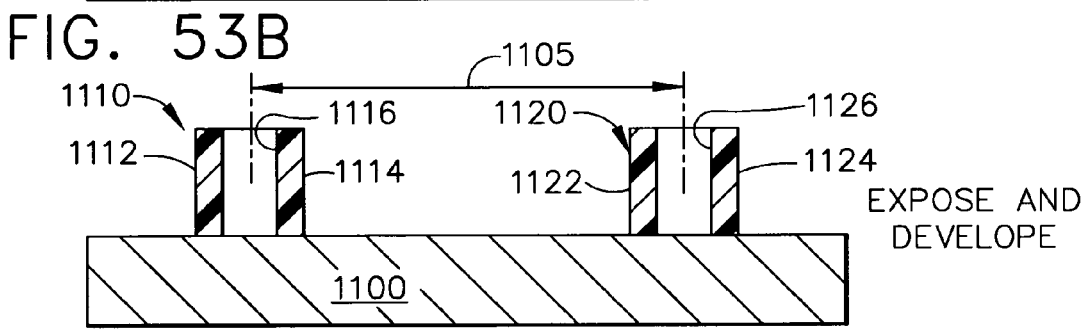

FIG. 53C represents an expose and develop step, in which a chemical compound is used to etch away the portions of the PMMA material that were not protected by the mask 1104 in the prior step at FIG. 53B. On FIG. 53C, the three-dimensional microneedle shapes begins to become apparent. A pair of hollow microneedle forms are illustrated in FIG. 53C at 1110 and 1120. In cross-section, the microneedle form 1110 shows a first wall at 1112, a second wall at 1114, and a hollow area or hole at 1116. Similarly, the microneedle form 1120 comprises a first wall at 1122, a second wall at 1124, and hollow area or hole at 1126.

Both microneedle forms 1110 and 1120 will be of the appropriate length and outer diameter to produce microneedle arrays as recommended hereinabove. The separation between microneedles is depicted by the dimension 1105, and this also will preferably be of a distance as recommended hereinabove.

Figure 53D:
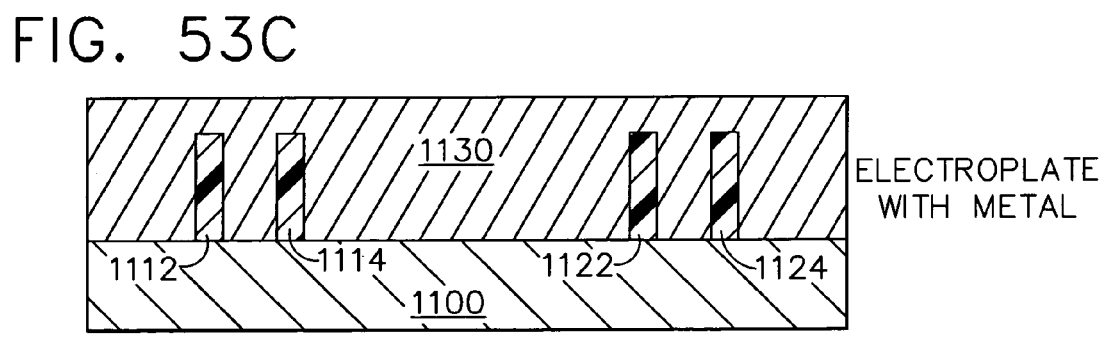

FIG. 53D is a step where the microneedle forms are electroplated with metal. In the preferred embodiment, this metal at 1130 will comprise nickel. As an optional intermediate step, the substrate 1100 and microneedle forms at 1112, 1114, 1122, and 1124 (which in combination comprise two circular or cylindrical microneedle forms) can be chemically coated to aid in later release before the electroplating takes place.

Figure 53E:
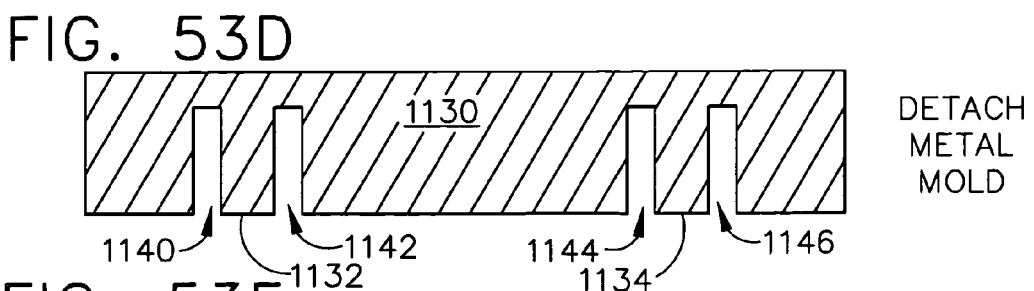

After the nickel electroplating has achieved the appropriate thickness, the step of detaching this metal form takes place in the step illustrated on FIG. 53E. A "reverse contour" mold will now exist, as generally depicted by the reference numeral 1130. Instead of a hollow area or hole, a cylindrical projection now appears at 1132 and 1134 in the metal mold. Similarly, instead of cylindrical or nearly cylindrical projections at 1112, 1114, and 1122, 1124 (as seen on FIGS. 53C and 53D), there are now hollow cylindrical shapes formed at 1140–1142, and 1144–1146, which represent the areas where the microneedle cylindrical walls will form.

Figure 54A:
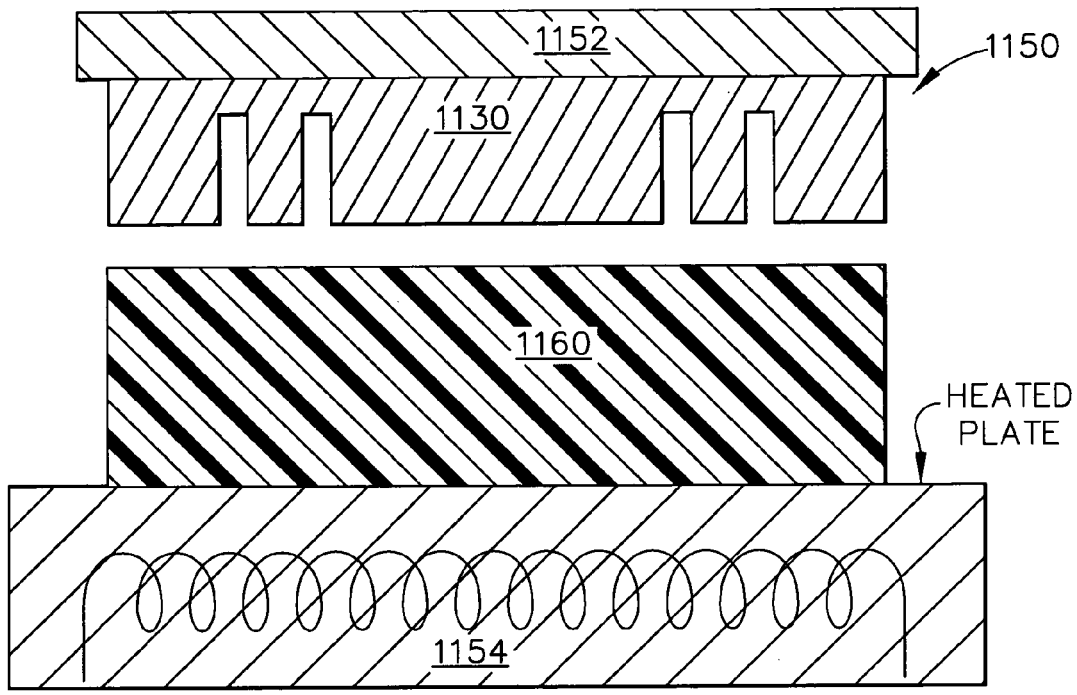
FIGS. 54A–54F are elevational views in cross-section of process steps for a microembossing procedure to create hollow microneedles, as well as micromachining and laser burning steps to create hollow chambers and through-holes in the bottom of the substrate structure.
Figure 54B:
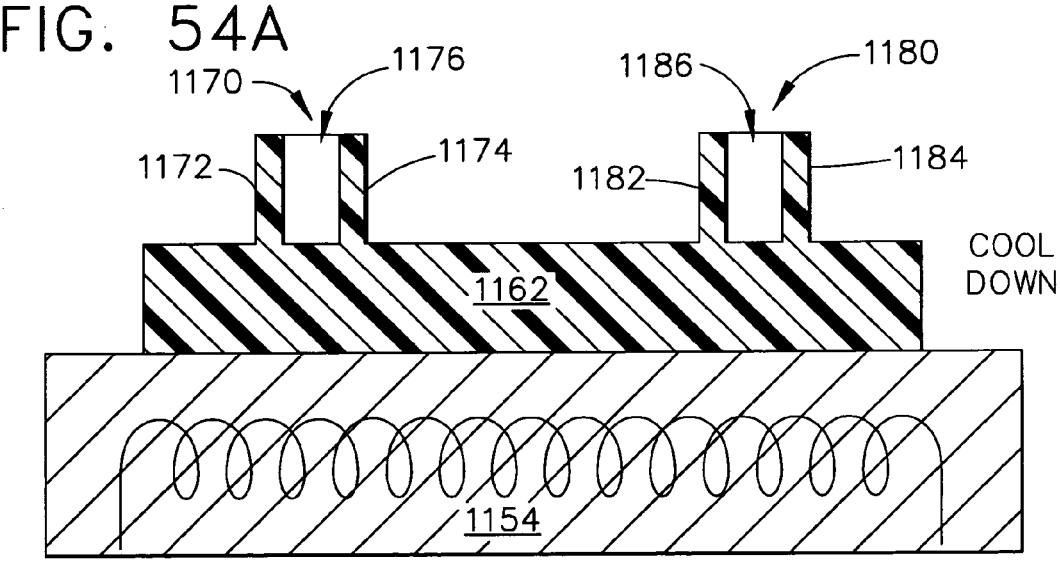
Figure 54C:
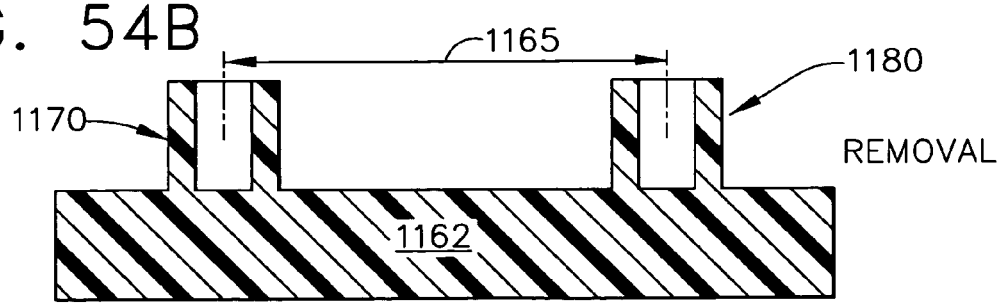

FIGS. 54A–54C depict the steps of microembossing to form molded microneedles that are hollow, as constructed according to the principles of the present invention. The metal microneedle mold at 1130 is attached to a moveable press ram 1152, to form a structure that will be impressed against a polymer or other plastic material. This moveable structure is indicated by the reference numeral 1150. The polymer or other type of plastic material at 1160 is placed on the surface of a heated plate 1154. The microneedle material preferably will comprise a biocompatible polymer material, although other materials could be used including polycarbon, or even PMMA.

The heated plate 1154 provides sufficient thermal energy to raise the temperature of the biocompatible polymer material at 1160 until it becomes readily deformable. In other words, the polymer material is placed into its "plastic" stage by raising its temperature substantially to its elastic working temperature. The moveable press assembly 1150 is now pressed down toward the heated plate 1154 and against the biocompatible polymer material 1160. It is preferred to accomplish this task within a vacuum to preserve the biocompatibility and sterilization characteristics of the future microneedles.

A cool-down stage is next, as depicted by the final result in FIG. 54B. The heated plate 1154 now becomes a cooling plate, and the biocompatible polymer material is cooled to the point where it becomes solid and will not readily deform. The moveable press ram assembly 1150 is now raised, thereby leaving behind a microneedle array having a substrate at 1162. In the illustrated embodiment of FIG. 54B, there are two hollow microneedles at 1170 and 1180, not yet having through-holes in the substrate 1162. The microneedle at 1170 is depicted in cross-section as having a first wall 1172 and a second wall 1174, which are generally cylindrical in shape. These walls surround a hollow area or hole at 1176. Similarly, microneedle 1180 shows a cross-section of a pair of walls at 1182 and 1184, containing a cylindrical hollow area at 1186.

After the cool-down stage, the microneedle array is removed from the plate 1154, thereby leaving behind the structure as illustrated at FIG. 54C. The microneedle separation is indicated at the dimension 1165. This dimension is equal to the dimension 1105 depicted on FIG. 53C.

It will be understood that other types of plastic forming processes can be used than embossing. In fact, virtually all types of molding or micromolding processes can be utilized. Embossing is one subset of these types of moldings, and injection molding is a second subset, which was described hereinabove for other microneedle shapes.

The above structure depicted in FIG. 54C could be used as the "final" product for certain uses with skin. This structure consists of substrate 1162 and two hollow microneedles 1170 and 1180, in which the hollow cavities 1176 and 1186 each form a small cup-like volume that does not protrude completely through the substrate 1162. This structure could be used for drug delivery by filling the cup-like hollow cavities 1176 and 1186 with a drug active that can slowly leach out into biological systems.

Figure 54D:
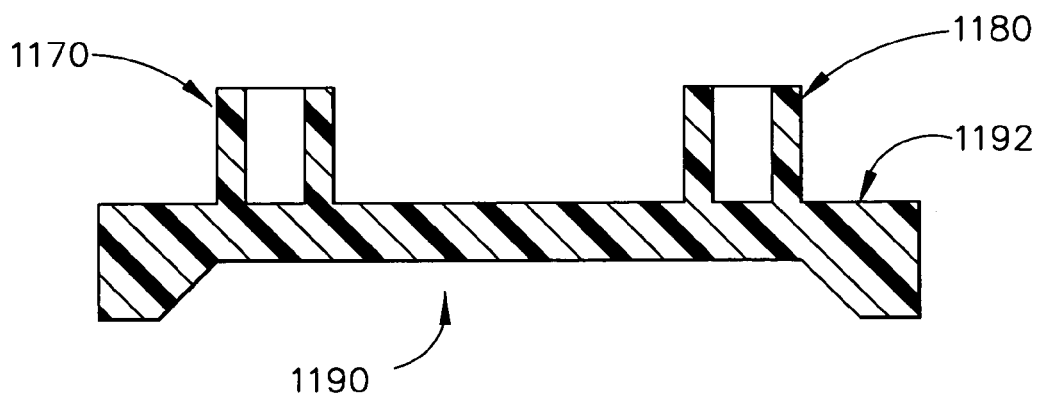
Figure 54E:
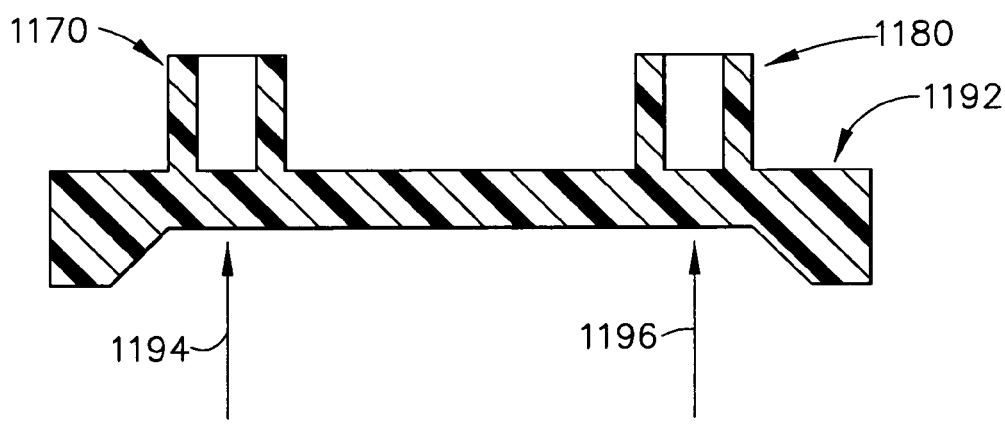
Figure 54F:
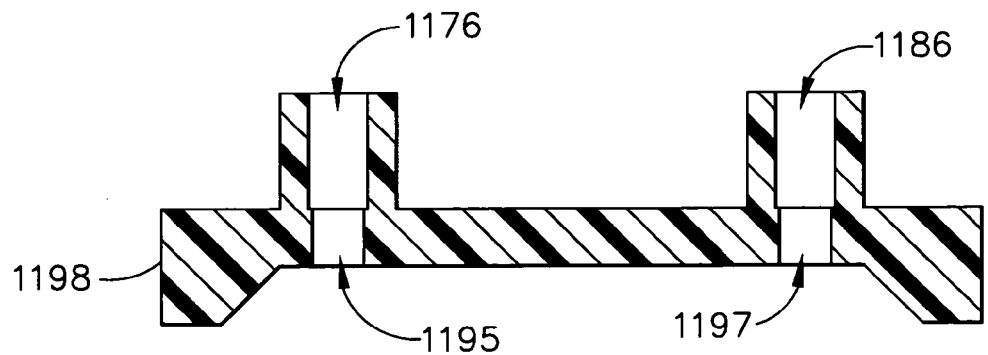

FIGS. 54D–54F illustrate various methods of forming chambers beneath the microneedle array, and forming through-holes. In FIG. 54D, a hollow chamber at 1190 is formed on the opposite side of the substrate, thereby forming a microneedle array structure 1192 that contains hollow microneedles 1170 and 1180, and a chamber that can hold some type of fluid. This chamber can be formed by micromachining, or perhaps by an oxygen plasma etching process. Other methodologies could be used without departing from the principles of the present invention.

In FIG. 54E, a laser light source is used to finish the "drilling" process to make through-holes that are concentric or otherwise centered along the hollow microneedles 1170 and 1180. On FIG. 54E, a laser light source is used to burn away some of the substrate material along the lines at 1194 and 1196. The final result is shown at FIG. 54F, in which a final microneedle array 1198 is illustrated showing through-holes from the chamber 1190 to the top of the microneedles, in which the microneedle openings 1176 and 1186 are aligned with the laser light burned holes at 1195 and 1197, respectively.

FIGS. 55A–55F illustrate an alternative methodology for constructing hollow plastic microneedles. Starting with a laminate material at 1200 and a biocompatible polymer at 1202, these materials are joined along a planar surface at the line 1204 on FIG. 55A. This joining can be performed by an adhesive process, or other temporary mechanical means.

Figure 55A:
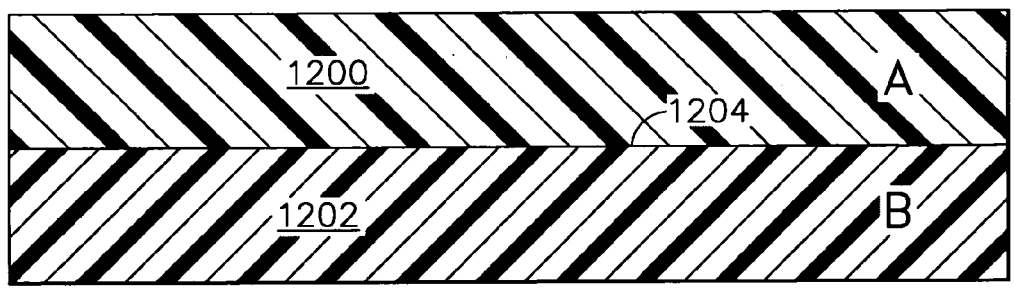
FIGS. 55A–55F are elevational views in cross-section of further process steps for creating hollow microneedles.
Figure 55B:
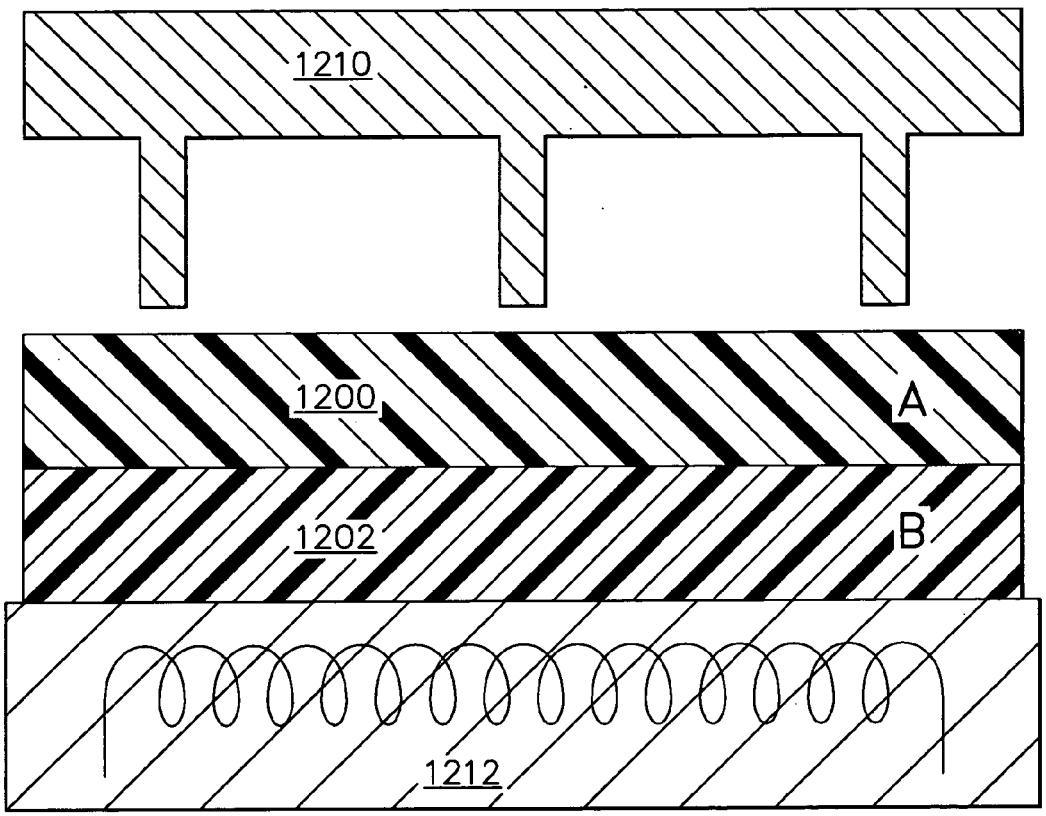
Figure 55C:
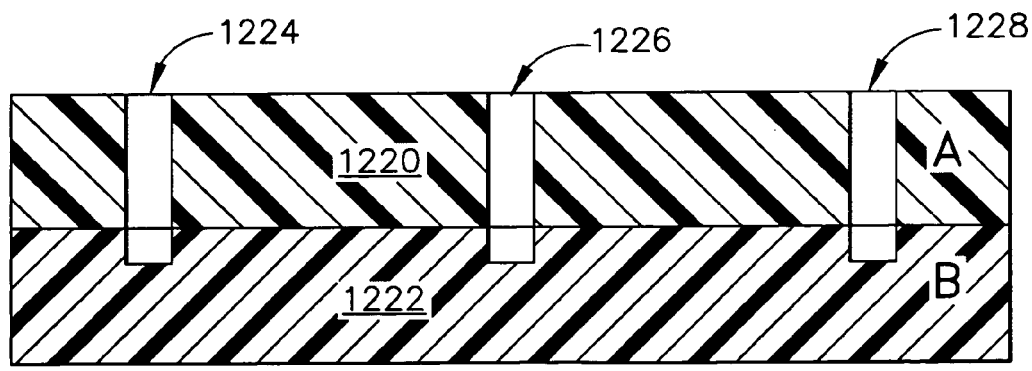

A mold 1210 is now provided, which preferably will be made of a metallic or other suitable material. In FIG. 55B, the biocompatible polymers are placed on a heated plate 1212, and the mold 1210 is placed upon a moveable press ram. After the mold has been pressed into the biocompatible polymers, the ram press is removed and the material is cooled, thereby arriving at a structure illustrated in FIG. 55C in which holes 1224, 1226, and 1228 are formed all the way through the upper layer, now designated as 1220. These holes also continue part-way into the lower layer at 1222.

Figure 55D:
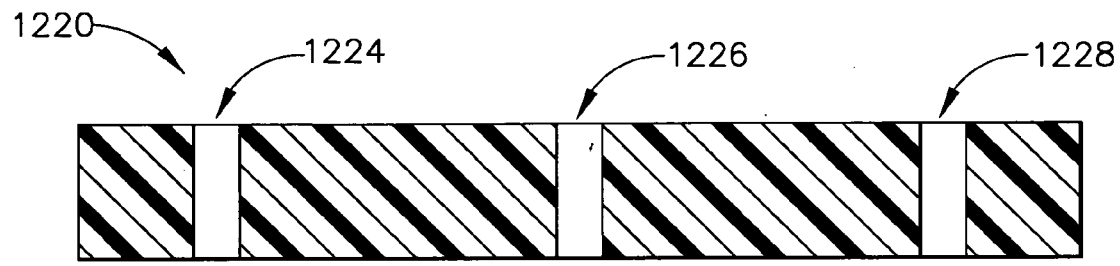
Figure 55E:
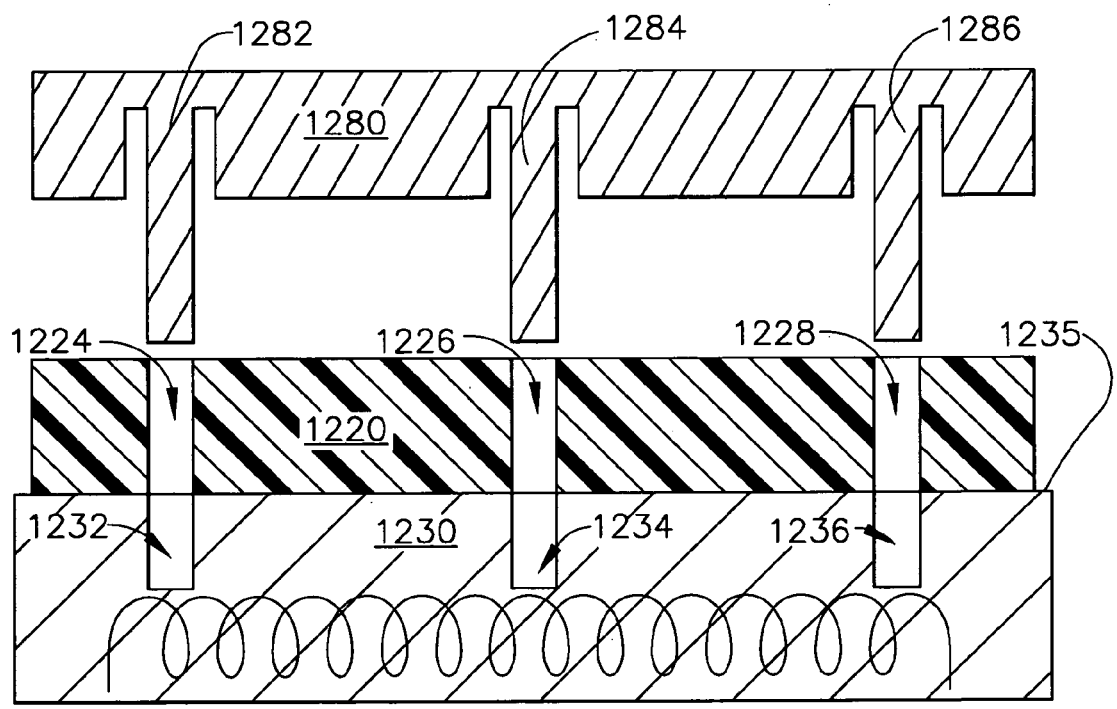

The laminate materials that were earlier glued together are now detached from one another. This now provides a film structure 1220 that has the through-holes 1224, 1226, and 1228, and is illustrated in FIG. 55D. This film layer 1220 is now placed upon a heated plate 1230. A mold structure 1280 is now provided and will be pressed against film layer 1220 after the film layer 1220 has been heated to its plastic stage. On FIG. 55E, the cylindrical projections 1282, 1284, and 1286 are used to create the through-holes for three hollow microneedles.

In an alternative configuration, the cylindrical projections 1282, 1284, and 1286 can be somewhat shortened so that they rest against the planar top surface of the heated plate 1230, i.e., along the horizontal (on FIG. 55E) line 1235. The heated plate 1230, in this alternative configuration, would be substantially flat along its top surface at 1235, such that the openings 1232, 1234, and 1236 would be filled.

Figure 55F:
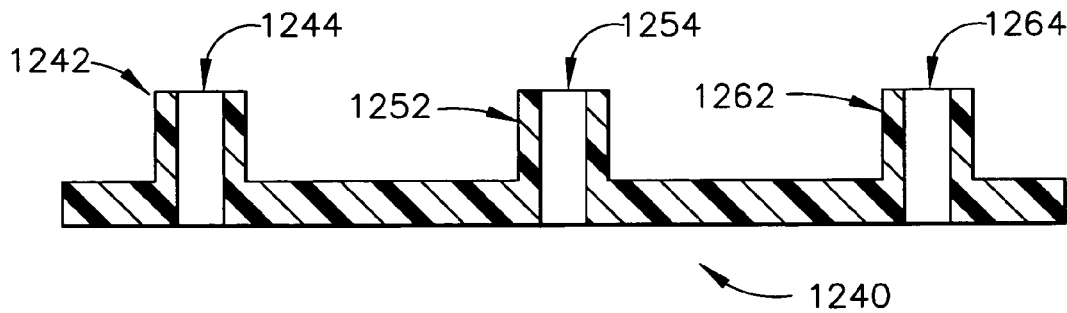

After the pressing process has occurred and the material 1220 is cooled (by plate 1230) to the point where it becomes solidified, the mold 1280 is removed and a new structure at 1240 is formed and removed from the plate 1230. This is illustrated in FIG. 55F. This new structure 1240 represents a microneedle array having three hollow cylindrical microneedles at 1242, 1252, and 1262. These microneedles have hollow through-holes as illustrated at 1244, 1254, and 1264, respectively.

Figure 56A:
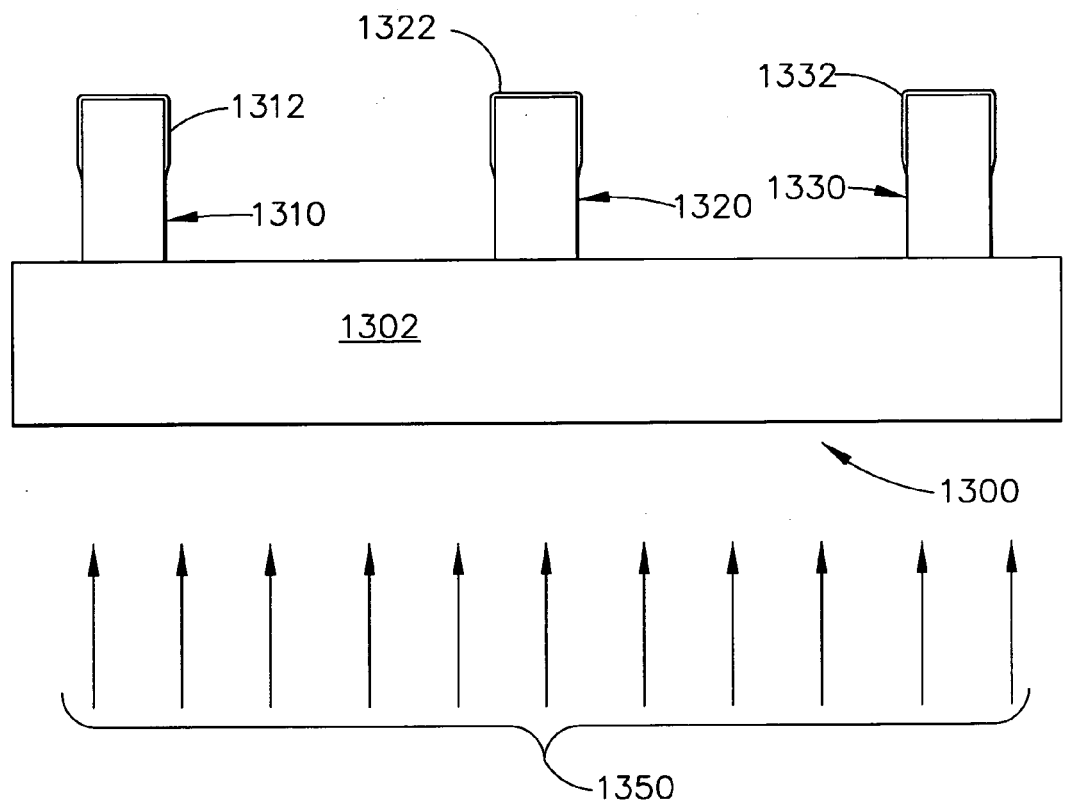
FIGS. 56A–56B are an elevational views in cross-section of microneedle arrays that have sensing capabilities using optical devices or chemical coatings.

Another use for the microneedles of the present invention is to include a sensing capability by some type of optical means with a plastic microneedle array structure that is constructed of a substantially transparent material. This could be used with both hollow and solid microneedles, although it is preferred that solid microneedles be used to prevent contamination of the light source mechanism that is being utilized for this sensing capability. In FIG. 56, a microneedle array structure 1300 is depicted as having a substrate 1302, and three microneedles at 1310, 1320, and 1330. The upper areas of these microneedles near their tips are coated with a chemical material that aids in detecting a chemical or other biological process. This chemical coating is indicated on the three microneedles at 1312, 1322, and 1332.

Once the microneedle array 1300 has been placed into the skin, a light source is used to provide electromagnetic energy in the direction indicated by the arrows 1350. It is preferred that the light source be some type of laser source, so that the electromagnetic energy is collimated. The chemical coating at 1312, 1322, and 1332 will be of a type that will either change color or change its light passing characteristics when in contact with the target fluid or biological materials. In this methodology, the laser light that is reflected back toward the optical energy source will either be reduced in intensity, as compared to before any chemical changes were noted at the ends of the microneedles, or will have a color variation.

Another use for this configuration is to provide optical energy directly into portions of skin that can be directly affected or stimulated by certain frequencies of light. In this instance, the laser light may directly provide either optical or thermal energy into skin tissue, or could provide a methodology for transferring such energy into muscle tissue at certain locations in an animal body.

Alternatively, the sensors can be integrated with the microneedle array by layering the sensor components on the face of the device containing the protrusions that will perforate the skin. One or more layers can be used depending upon the complexity of the detection process. Simple conductivity measurements for analytes like sodium ions can be made with only one conductive layer of a biocompatible material, such as the layer 1312 on FIG. 56A, or a layer 1372 on FIG. 56B.

Figure 56B:
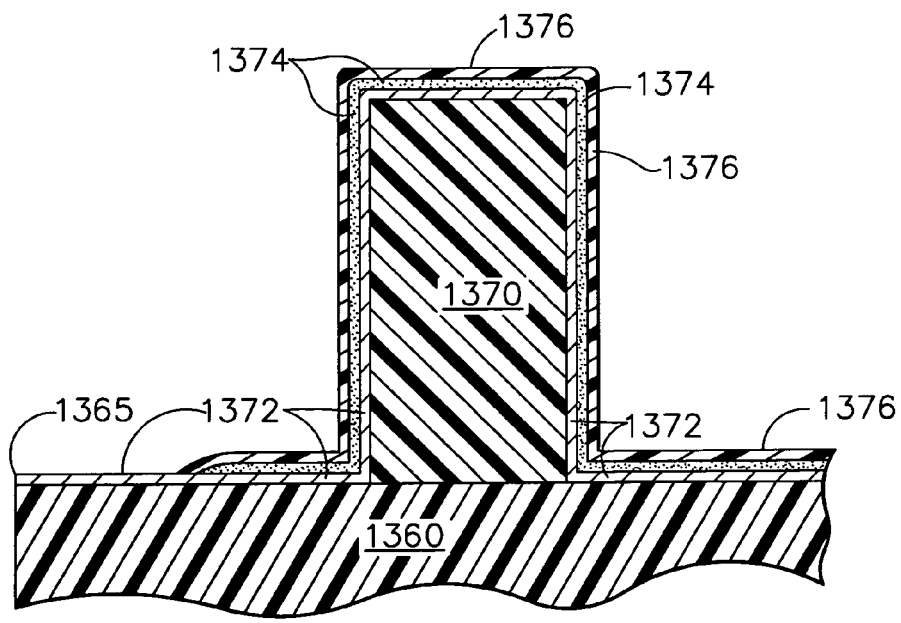

More complex analyses (e.g., glucose) are accomplished by using several layers of sensing materials. To prepare an enzyme electrode, a biocompatible prepolymer doped with an enzyme, an enzyme modified with a polymerizable group, or an enzyme modified with a group that can be tethered or adsorbed to the electroconductive surface is coated on top of the electrically conductive polymer and is polymerized using a curing agent or an energy source such as light, or heat as necessary. This is illustrated in FIG. 56B where the coating constitutes an enzyme layer that is depicted at 1374. The electrically conductive layer is depicted at 1372. A single microneedle structure 1370 is illustrated in FIG. 56B as a longitudinal element protruding from a substrate 1360, however, it will be understood that many such longitudinal elements can be constructed on the substrate 1360 to create a microneedle array (similar to, e.g., the microneedles 1310, 1320, and 1330 on FIG. 56A).

The enzyme film can also be coated with additional layers of biocompatible polymers (as depicted at 1376) that can be employed to protect the sensor components from leaching, reactions with biological entities, or to regulate the access of analytes to the enzyme layer. As depicted in FIG. 56B, the electrically conductive layer 1372, enzyme layer 1374, and "top" polymer layer 1376 are deposited on virtually the entire surface of the microneedle array, except for an portion at the end of the substrate structure, as generally depicted by the reference numeral 1365. The side walls of a microneedle array comprising multiple microneedle devices such as the microneedle structure 1370 are not completely coated with the enzyme layer 1374 or second polymer layer 1376, because those areas will be used for electrical contact with an electrochemical analysis circuit. Therefore, only the electrically conductive layer 1372 is deposited throughout the upper surface of the substrate 1360, including the portions near the left (on FIG. 56B) hand end, at the numeral 1365.

These sensor component layers 1372, 1374, 1376 can be deposited on microneedles (e.g., microneedle 1370) by dipping the microneedle devices in the appropriate chemical reagents, spin-coating techniques, electro deposition, stamping, deposition of dry powders, and similar processes known by those skillful in the art. The left-end portion near 1365 is preferably masked during the deposition procedures for the enzyme layer or second polymer layer, thereby leaving exposed the electrically conductive layer 1372 in this region.

The first conductive layer 1372 deposited on the microneedles can consist of many available materials; metals are preferred and include: Au, Cr, Ti, Pt, Ag, Cu. Conductive polymer mixtures such as 7,7,8,8-tetracyanoquinodimethane with tetrathiafulvalene or N-methylphenazinium can also be used. Furthermore, conductive polymers such as polyacetilene, polythiophene, polyparaphenylene, and polyphenylene vinylene and polyaniline can be used.

The enzyme coating can be entrapped in any one of the following polymers or copolymer mixtures in the second layer at 1374: glutaraldehyde, poly(ethylene glycol) diclycidy ether and poly[(1-vinylimidazole) osmium (4,4'dimethyl bipryidine)$_2$Cl], poly N-methylpyrrole, poly [(vinyl pyridine) Os(bipyridine)$_2$Cl], cyclodextrin polymers, and gelatin.

The outer biocompatible protection layer at 1376 can include: silicones, fluorinated-ethylene propylene, nafion, cellulose, poly(vinylpyridine) acetate, aziridine, polyurethanes, epoxies, fluorocarbons, acrylics, parylene, and polyimides.

Another use for this configuration is to provide electrical energy directly into portions of skin that can be directly affected or stimulated by a small electrical current. In this instance, the electricity is conducted via the conductive layer 1372. If it is desirable to provide electrical current directly at the tips of the microneedles, then the enzyme layer 1374 and protective polymer layer 1376 can be eliminated from the manufacturing process, leaving only the electrically conductive layer 1372 covering the entire substrate 1360 and microneedle structure at 1370. In this manner, electrical energy may be directly provided into skin tissue, or could ultimately be transferred into muscle tissue at certain locations in an animal body.

FIGS. 57A and 57B illustrate a refinement of the embossing process that was earlier described in relation to FIGS. 54A–54C. In FIG. 57A, the microneedle substrate at 1400 has been deformed by a metal (or other type of material) mold at 1410. A single hollow microneedle structure is being formed in FIG. 57A, as indicated by the cross-section cylindrical wall at 1402 and 1404. As the substrate material 1400 is cooled, shear forces are generated during the demolding procedure which occurs when the mold 1410 is removed from the upper surface of the substrate 1400. These shear forces will mainly occur along the inner surfaces of the walls 1402 and 1404, which indicate the inner diameter of the hollow microneedle near its tip.

The amount of shear forces can be controlled by the cool-down temperature and timing as to when the mold 1410 is released. If the shear force is maintained at a sufficient magnitude, the final structure will not have a perfectly flat surface along the top of the microneedle, but instead will have a shape similar to that of the microneedle 1420 depicted in FIG. 57B. In this microneedle 1420, the upper surface of the microneedle has sharp points at 1422 and 1424, and a rather arcuate shape along two of its semi-circular edges at 1426. This shape also can be parabolic or elliptical in nature, and the important aspect of this shape is to provide sharper edges at the points 1422 and 1424. This is an alternative methodology for forming hollow circular microneedles that can more easily penetrate the stratum corneum of skin, and may not require the edged blades of the microneedle structures depicted in FIG. 32.

The star-shaped solid microneedle structures can also be created using a molding process similar to that depicted in FIGS. 53A–53E, and 54A–54C. Of course, the solid microneedles will not require through-holes that are in alignment with the center of each microneedle, but will instead require through-holes in the substrate material at locations that are substantially proximal to the pair of blade structures near the top surface of the substrate.

It will be understood that all types of molding or casting procedures could be utilized in conjunction with the present invention, so long as these molding procedures can be utilized to create the very small structures required by the microneedles of the present invention. Furthermore, semiconductor fabrication techniques can be used to create the structures illustrated on FIGS. 32–36, using processes that were described hereinabove in reference to FIGS. 18–22. Certainly fluid reservoirs can be constructed for use with the microneedle structures of FIGS. 32–36, and furthermore various methods of use can be utilized with these microneedle structures, such as electrophoresis or ultrasound.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. An integral structure comprising a base element and plurality of microneedles formed thereon, said microneedles suitable for penetrating the stratum corneum layer of skin, wherein said base element has a first side and a second side;

said plurality of microneedles comprising a plurality of projections disposed on said outer surface of said microneedles and which extend from the second side of said base element along longitudinal axes, in a longitudinal direction from a proximal end towards a distal end, and exhibiting at least one angle with respect to said base element; and said plurality of projections being spaced apart from one another at a substantially predetermined separation distance, and said plurality of projections having a substantially uniform length, wherein:

said substantially predetermined separation distance is within a range of 50–1000 microns, and said substantially uniform length is within a range of 50–3000 microns, wherein said microneedles have at least one elongate sharp edge that enhances penetration of said microneedles through the stratum corneum layer of skin, wherein said elongate sharp edge is oriented in the longitudinal direction and extends entirely from said proximal end of said microneedle to said distal end of said microneedle.

\* \* \* \* \*